US010350095B2

(12) United States Patent
Fish

(10) Patent No.: US 10,350,095 B2
(45) Date of Patent: Jul. 16, 2019

(54) PROSTHETIC VASCULAR VALVE AND METHODS ASSOCIATED THEREWITH

(71) Applicant: INCUBAR LLC, Broomfield, CO (US)

(72) Inventor: R. David Fish, Houston, TX (US)

(73) Assignee: Incubar, LLC, Broomfield, CO (US)

( * ) Notice: Subject to any disclaimer, the term of this patent is extended or adjusted under 35 U.S.C. 154(b) by 0 days.

(21) Appl. No.: 16/104,821

(22) Filed: Aug. 17, 2018

(65) Prior Publication Data

US 2019/0053927 A1 Feb. 21, 2019

Related U.S. Application Data

(60) Provisional application No. 62/547,021, filed on Aug. 17, 2017.

(51) Int. Cl.
| *A61F 2/00* | (2006.01) |
| *A61F 2/90* | (2013.01) |
| *A61F 2/95* | (2013.01) |
| *A61F 2/848* | (2013.01) |
| *A61F 2/24* | (2006.01) |

(52) U.S. Cl.
CPC .............. *A61F 2/90* (2013.01); *A61F 2/0095* (2013.01); *A61F 2/2427* (2013.01); *A61F 2/2475* (2013.01); *A61F 2/848* (2013.01); *A61F 2/95* (2013.01); *A61F 2002/8483* (2013.01); *A61F 2210/0004* (2013.01); *A61F 2210/0014* (2013.01); *A61F 2220/0075* (2013.01); *A61F 2230/0069* (2013.01); *A61F 2240/001* (2013.01)

(58) Field of Classification Search
CPC .......... A61F 2/0095; A61F 2/848; A61F 2/90; A61F 2/95; A61F 2002/8483; A61F 2210/0004; A61F 2210/0014; A61F 2220/0075; A61F 2230/0069; A61F 2240/001

See application file for complete search history.

(56) References Cited

U.S. PATENT DOCUMENTS

| 3,878,565 | A | 4/1975 | Sauvage |
| 3,945,052 | A | 3/1976 | Liebig |
| 4,164,045 | A | 8/1979 | Bokros et al. |
| 4,545,082 | A | 10/1985 | Hood |
| 4,759,758 | A | 7/1988 | Gabbay |

(Continued)

FOREIGN PATENT DOCUMENTS

WO 2002087467 A2 11/2002

OTHER PUBLICATIONS

International Search Report and Written Opinion issued in PCT/US2018/000325 dated Jan. 24, 2019, 11 pages.

*Primary Examiner* — Jocelin C Tanner

(74) *Attorney, Agent, or Firm* — Faegre Baker Daniels LLP

(57) ABSTRACT

A prosthetic vascular valve includes one or more continuous loops of frame material or one or more strands of material that do not form a continuous loop. The frame includes a plurality of longitudinal portions, wherein a membrane is attached to at least one of the longitudinal portions, and wherein the membrane is configured to open and close. During implantation, the frame engages the inner surface of the vein wall and is biased against the vein wall to remain stationary. In use, blood flows from an upstream end to a downstream end, wherein the membrane mitigates regurgitation of the blood as the blood is conveyed through the subject vein.

7 Claims, 30 Drawing Sheets

(56) References Cited

U.S. PATENT DOCUMENTS

| | | |
|---|---|---|
| 4,851,001 A | 7/1989 | Taheri |
| 4,892,539 A | 1/1990 | Koch |
| 5,282,847 A | 2/1994 | Trescony et al. |
| 5,383,927 A | 1/1995 | De Goicoechea et al. |
| 5,522,881 A | 6/1996 | Lentz |
| 5,609,598 A | 3/1997 | Laufer et al. |
| 5,769,780 A | 6/1998 | Hata et al. |
| 5,840,081 A | 11/1998 | Andersen et al. |
| 5,855,601 A | 1/1999 | Bessler et al. |
| 6,126,686 A | 10/2000 | Badylak et al. |
| 6,241,763 B1 | 6/2001 | Drasler et al. |
| 6,287,335 B1 | 9/2001 | Drasler et al. |
| 6,299,637 B1 | 10/2001 | Shaolian et al. |
| 6,358,275 B1 | 3/2002 | McIlroy et al. |
| 6,358,284 B1 | 3/2002 | Fearnot et al. |
| 6,432,712 B1 | 8/2002 | Wolfinbarger, Jr. |
| 6,458,153 B1 | 10/2002 | Bailey et al. |
| 6,494,909 B2 | 12/2002 | Greenhalgh |
| 6,503,272 B2 | 1/2003 | Duerig et al. |
| 6,585,761 B2 | 7/2003 | Taheri |
| 6,652,578 B2 | 11/2003 | Bailey et al. |
| 6,951,571 B1 | 10/2005 | Srivastava |
| 6,986,735 B2 | 1/2006 | Abraham et al. |
| 7,153,324 B2 | 12/2006 | Case et al. |
| 7,189,259 B2 | 3/2007 | Simionescu et al. |
| 7,214,242 B2 | 5/2007 | Abraham et al. |
| 7,261,732 B2 | 8/2007 | Justino |
| 7,503,928 B2 | 3/2009 | Case et al. |
| 7,524,330 B2 | 4/2009 | Berreklouw |
| 7,563,277 B2 | 7/2009 | Case et al. |
| 7,582,110 B2 | 9/2009 | Case et al. |
| 7,585,321 B2 | 9/2009 | Cribier |
| 7,604,661 B2 | 10/2009 | Pavcnik et al. |
| 7,648,676 B2 | 1/2010 | Mills et al. |
| 7,670,368 B2 | 3/2010 | Hill et al. |
| 7,744,642 B2 | 6/2010 | Rittgers et al. |
| 7,780,722 B2 | 8/2010 | Thielen et al. |
| 8,303,649 B2 | 11/2012 | Agnew et al. |
| 8,308,797 B2 | 11/2012 | Paniagua et al. |
| 8,361,144 B2 | 1/2013 | Fish et al. |
| 8,366,761 B2 | 2/2013 | Paul et al. |
| 9,333,075 B2 | 5/2016 | Biadillah et al. |
| 9,421,096 B2 | 8/2016 | Case et al. |
| 9,737,400 B2 | 8/2017 | Fish et al. |
| 2002/0055772 A1 | 5/2002 | McGuckin et al. |
| 2002/0079286 A1* | 6/2002 | Haynes .............. A61F 2/0095 215/276 |
| 2002/0099439 A1 | 7/2002 | Schwartz et al. |
| 2002/0177894 A1 | 11/2002 | Acosta et al. |
| 2003/0055492 A1 | 3/2003 | Shaolian et al. |
| 2003/0130727 A1 | 7/2003 | Drasler et al. |
| 2003/0212454 A1* | 11/2003 | Scott .................. A61F 2/2412 623/2.14 |
| 2004/0024452 A1 | 2/2004 | Kruse et al. |
| 2005/0137676 A1* | 6/2005 | Richardson .......... A61F 2/2418 623/1.11 |
| 2005/0137682 A1 | 6/2005 | Justino |
| 2006/0089708 A1 | 4/2006 | Osse et al. |
| 2006/0190074 A1 | 8/2006 | Hill et al. |
| 2006/0259137 A1 | 11/2006 | Artof et al. |
| 2007/0027525 A1 | 2/2007 | Ben-Muvhar |
| 2007/0050014 A1 | 3/2007 | Johnson |
| 2008/0046071 A1 | 2/2008 | Pavcnik |
| 2008/0154356 A1 | 6/2008 | Obermiller et al. |
| 2008/0177381 A1 | 7/2008 | Navia et al. |
| 2008/0183280 A1 | 7/2008 | Agnew et al. |
| 2008/0200977 A1 | 8/2008 | Paul et al. |
| 2009/0062907 A1 | 3/2009 | Quijano et al. |
| 2009/0187241 A1 | 7/2009 | Melsheimer |
| 2009/0248149 A1 | 10/2009 | Gabbay |
| 2009/0254175 A1 | 10/2009 | Quijano et al. |
| 2010/0234878 A1 | 9/2010 | Hruska et al. |
| 2010/0256749 A1 | 10/2010 | Tran et al. |
| 2011/0295363 A1* | 12/2011 | Girard ................ A61F 2/2412 623/1.26 |
| 2011/0300625 A1 | 12/2011 | Paniagua et al. |
| 2011/0301700 A1* | 12/2011 | Fish ..................... A61F 2/0095 623/2.11 |
| 2012/0078343 A1 | 3/2012 | Fish |
| 2012/0078356 A1* | 3/2012 | Fish ..................... A61F 2/2418 623/2.17 |
| 2012/0158128 A1* | 6/2012 | Gautam ............... A61F 2/0095 623/2.11 |
| 2013/0190862 A1* | 7/2013 | Pintor .................. A61F 2/2403 623/2.18 |
| 2014/0114402 A1* | 4/2014 | Ahlberg .............. A61F 2/2418 623/2.11 |
| 2016/0324639 A1* | 11/2016 | Nguyen .............. A61F 2/2409 |
| 2017/0165067 A1* | 6/2017 | Barajas-Torres ...... A61F 2/2415 |

* cited by examiner

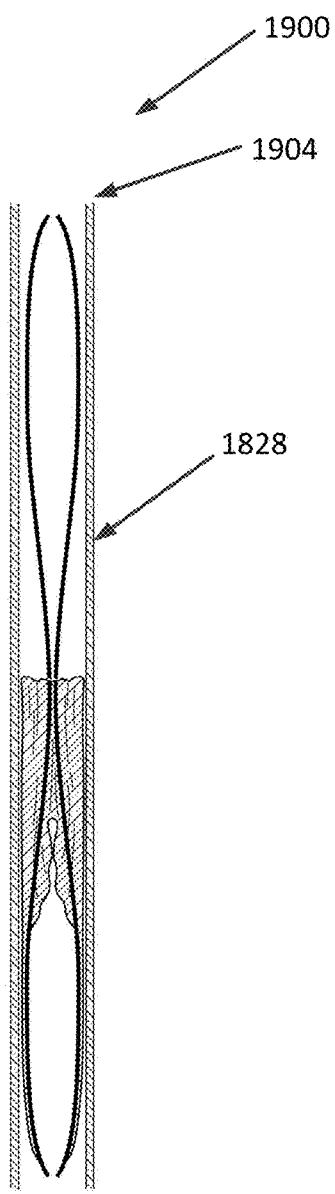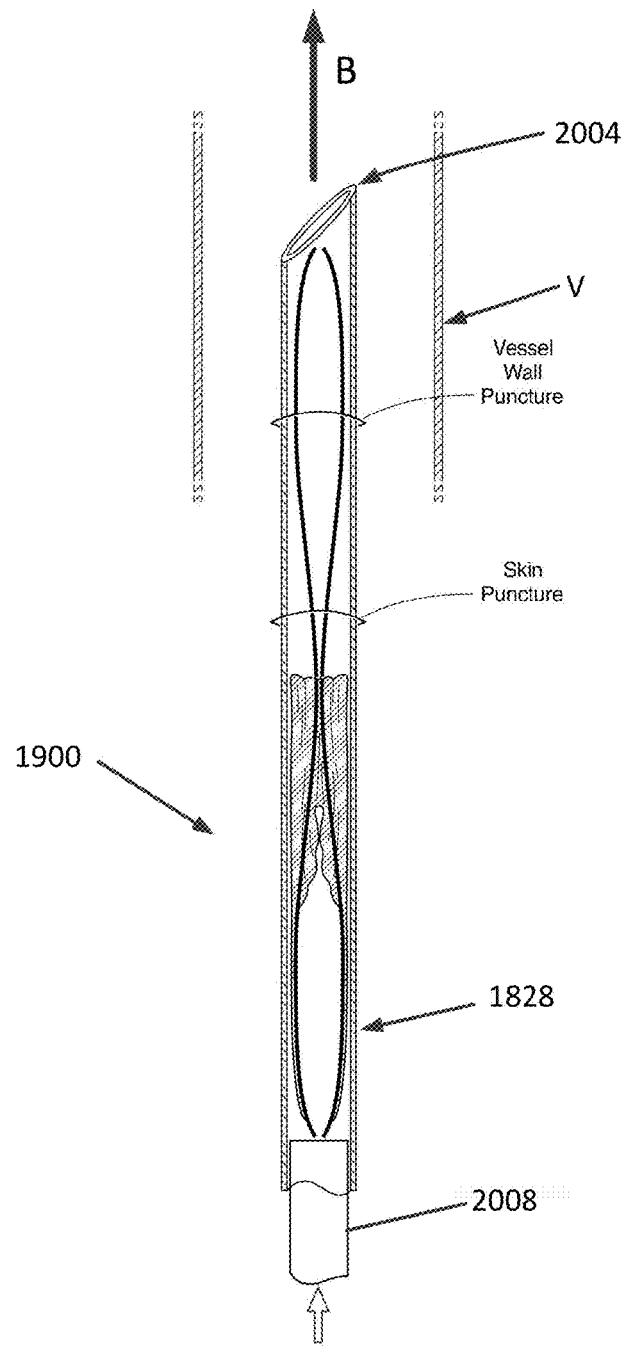
FIG. 19
FIG. 20

PROSTHETIC VASCULAR VALVE AND METHODS ASSOCIATED THEREWITH

RELATED APPLICATION

The present application claims the benefit of U.S. Provisional Patent Application No. 62/547,021 filed on Aug. 17, 2017, the content of which is incorporated herein by reference in its entirety.

FIELD

The one or more inventions described herein are directed to medical implants, and more particularly, to prosthetic vascular valves, including prosthetic venous valves, and methods related thereto.

BACKGROUND

Venous insufficiency includes a range of conditions. As background, veins function to return blood to the central circulation and to the heart, and therefore, veins carry the blood from the farthest extremities of the body. In most cases, because veins are post-capillary, meaning the veins follow the capillaries and the antegrade circulation of the blood, the veins are at a very low pressure relative to the arterial pressure. Accordingly, the hydrodynamic forces available to return the blood to the central circulation and to the heart are low. In human physiology there are mechanisms in the circulation of the extremities to promote the return flow of venous blood to the central circulation.

Among these naturally occurring anatomical mechanisms notably in the extremities are valves distributed along the veins that act to prevent regurgitation of blood flow progressing toward the central veins. This is especially important in the lower extremities where most clinical problems are manifest because the lower extremities are hydrostatically substantially lower than the heart. The circulatory system in the lower extremities when in a dependent position must, nonetheless, convey blood back up to the central circulation against the hydrostatic pressure. Also essential, the leg muscle action of upright posture and ambulation acts to compress the veins of the deep vein system of the lower extremities and propel venous blood centrally. Further, communicating veins, also valved, conduct blood from the superficial veins into the deep veins so that muscle action serves to promote lower extremity vein blood flow generally.

In certain disease states chronic conditions can lead to compression of proximal veins and retarded return blood flow in the lower extremities, resulting in congestion of their venous systems and chronically elevated pressures for which they are not adapted. Over time, this leads to dilation of the veins that in turn causes failure of coaptation of the venous valves resulting in more congestion and swelling. This vicious cycle can progress to failure of a multiplicity of vein valves including those of the communicating veins and marked symptomatic dilation of the superficial veins. When the veins become dilated enough, all of the valves can become incompetent and in severe cases the entire function of moving blood back against the hydrostatic force can fail.

Veins are prone to this because they are thin-walled, being a low pressure vessel adapted to function at the often superficial level of a viscus or body part. This vulnerability increases with age and adverse loading conditions associated with certain functional and disease conditions. Among these are the effects of obesity and sedentary behavior that result in compression of the central veins along the posterior aspect of the pelvic bowl. That course joins the principal veins of the thorax and inferior vena cava to return blood to the heart. The weight of the abdominal contents, especially in sitting posture, can compress the veins of the pelvis, and aggravated by obesity and sedentary behavior, result in increased vein pressures in the lower extremities. As the vein pressures rise, the increase in pressure causes dilation of the veins and incompetence of their valves. In sum, as the veins dilate and the valves become incompetent, there is no way of restoring the normal caliber and architecture of the veins. As a result, the manifestations of the diseases that proceed from venous insufficiency become progressive and severe.

By way of example, complications thereafter can include lymphedema, which is partly related to the destruction of the lymphatic system that can cause the patient to become prone to infection with accompanying discomfort, and even destruction of the tissue may ensue.

Function of the lymphatic vessel system is also essential to the maintenance of fluid homeostasis in the soft tissues, including those of the lower extremities, and this function is directly influenced by the state of venous blood flow and pressure. In normal circulatory processes there is some movement of fluid from the post-capillary veins and collecting veins into the soft tissues. The contents of that fluid contains some degree of protein and formed elements of the blood (including cells). Such compositions in small quantities and in small flow can be absorbed by the lymphatics, which carry the fluid out of the tissue back into the central circulation through the lymph system. However, with chronic and excessive elevation of the vein pressure the high material content of the transudated fluid can overload the capacity of the lymphatic vessels causing them to become clogged and degraded. Destruction of portions of the lymphatic system increases the burden of what the remainder of the lymphatics have to carry, which is a degenerative cycle for the lymphatic system alone. Indeed, if the collective regional function of the lymphatics is sufficiently compromised, the patient can develop permanent retention of fluid in the tissue. Moreover, since the lymph system is also part of the means by which the immune system acts in the soft tissues, then a patient can develop a tendency to infection and damage to the tissue by virtue of congestion. Therefore, the impacts of venous insufficiency are not simply a matter of cosmetic appearance and/or discomfort, but the function of the venous system in the lower extremities is an important part of the patient's health and well-being.

Therapies to address venous insufficiency have been limited due, at least in part, to the structure of the venous system in the lower extremities. More particularly, in the lower extremities the human anatomy includes a superficial vein system and deep vein system. The deep vein system runs in the central muscle compartments of the lower extremity including the calf and thigh, such that muscle action squeezes the vein and propels the blood upward against hydrostatic pressure. Even so, if the deep veins lose their valves, for example, as can happen in the case of vein thrombosis, the patient can develop severe fluid congestion of the lower extremity. Apart from the more commonly understood superficial venous disease conditions, when the deep veins fail, there are serious consequences.

For all of the conditions that cause failure of the valves and dilatation of the superficial veins that can produce both pain and cosmetic problems by causing congestion and deformation of the skin, it has become popular to attempt to treat venous insufficiency, at least in the superficial veins.

In general, currently available forms of therapy for venous insufficiency are essentially destructive. By way of example, existing therapies exert tissue lysis effects on the vein with lasers or heat probes. Alternatively, the superficial veins are surgically removed, otherwise known as "vein stripping."

Accordingly, current therapies to address venous insufficiency are limited, and therefore, there is a need for additional therapies to address venous insufficiency. In particular, means are needed to treat venous insufficiency by restoring venous flow and valvular competence rather than by destroying the available superficial veins. Previous designs have suffered from limitations in positional stability causing the implanted valves to lose their position and axial orientation in the vessel and, therefore, all effectiveness in valvular function. This failing is caused by anatomic factors. First, the vein walls can be compliant to the point of laxity, and second, this compliance under hydrostatic cyclic pressure loading then causes the diameter of the vessel to change dramatically with subject posture and activity. Thus, a design is needed that can maintain contact with the inner surface of the vessel and retain its axial orientation under variable hydrostatic loads.

In other disease conditions the veins of an organ or body region may themselves be of normal configuration and native function, but the circulatory pressure loads exerted upon them may be markedly elevated due to congestive conditions in the heart or obstruction of the central veins. In such conditions, such as superior vena cava syndrome or severe tricuspid valve regurgitation, a device to treat the condition would be desirable.

SUMMARY

It is to be understood that the one or more present inventions include a variety of different versions or embodiments, and this Summary is not meant to be limiting or all-inclusive. This Summary provides some general descriptions of some but not necessarily all of the embodiments. In addition, this Summary may also include some more specific descriptions of other embodiments.

To maintain axial orientation , the inventive devices employ a frame design with a high aspect ratio, being relatively long in relation to its diameter. In at least some embodiments, portions of the frame thus extend axially well beyond the operating membrane portion to provide stabilizing structures that exert radially outward force and contact on the vessel wall at a distance from the membrane portion. This acts by principle of leverage to enforce axial alignment of the device within the vessel with a minimum of force applied to the vessel wall. Further, at least on some embodiments, the shape of the loop or loops of the frame are designed as a curvilinear course along a cylinder such that, by virtue of geometry, the loops maintain wall contact within a generally cylindrical vessel along its full length. To maintain wall contact under dynamic loading, one or more embodiments further employ a frame utilizing a shape-memory material that is also very compliant on radial compression, yet returns to its original shape under maximum hydrostatic distension of the vessel for which it is nominally sized. This achieves sufficient vessel wall contact under dynamic loading and ensures operation of the membrane valve element under the range of conditions imposed by the functional behaviors of the patient. Devices described below can be beneficial for treating venous insufficiency, as well as other conditions, including utilizing vascular valves implanted in regional veins to protect the regional circulation from the high central vein pressures. Apart from veins, arteries and other fluid conduits in the body may also benefit in their function from the implantation of a vascular valve.

Such conduits may also include those that are implanted surgically, whether of native or of prosthetic material, such as an arterio-venous dialysis fistula or a ventriculo-peritoneal shunt used to treat hydrocephalus.

At least some embodiments are directed to a prosthetic vascular valve that possesses different features. Accordingly, in at least one embodiment, a prosthetic vascular valve for use in a blood vessel or vascular conduit, the prosthetic vascular valve comprising: a frame including a loop section having a plurality of loops, the plurality of loops extending in an axial direction of the frame, wherein an outer surface of the plurality of loops is configured to lie on a common cylinder, and wherein each loop of the plurality of loops is a continuous loop; and a membrane attached to the loop section of the frame, the membrane including mobile portions that are configured to move radially inward and radially outward corresponding to closed and open positions of a free edge of the membrane, respectively, wherein the mobile portions of the membrane reside between convergence areas of the plurality of loops.

The prosthetic vascular valve(s) as described herein above, wherein the frame is made of a single piece of cut tubular material.

The prosthetic vascular valve(s) as described herein above, wherein the frame is made of one or more wire pieces.

The prosthetic vascular valve(s) as described herein above, wherein the frame is made of a shape-memory alloy.

The prosthetic vascular valve(s) as described herein above, wherein the shape-memory alloy is nitinol.

The prosthetic vascular valve(s) as described herein above, wherein the frame is made of a bio-absorbable material.

The prosthetic vascular valve(s) as described herein above, wherein the membrane comprises a cross-linked mammalian tissue.

The prosthetic vascular valve(s) as described herein above, wherein the cross-linked mammalian tissue comprises pericardia.

The prosthetic vascular valve(s) as described herein above, wherein the membrane is a single piece of material that does not include any seams and is made from a cylindrical piece of donor tissue that has been treated, shaped and attached to the frame.

The prosthetic vascular valve(s) as described herein above, wherein a frame extension including additional loops is located proximal to the loop section.

The prosthetic vascular valve(s) as described herein above, wherein the frame extension is flared radially outward and has a proximal valve width Wpv that is greater than a valve width Wv at the loop section of the frame.

The prosthetic vascular valve(s) as described herein above, wherein a distal flared portion of the loop section is flared radially outward and comprises a distal valve width Wdv that is greater than a valve width Wv at the loop section of the frame.

In another embodiment, a prosthetic vascular valve for use in a blood vessel or vascular conduit comprises: a frame including a loop section having a first loop and a second loop, wherein the first loop is situated diametrically opposite the second loop, wherein a length of the loop section of the frame is about two to eight times greater than a width of the loop section; and a membrane attached to the first loop and the second loop, the membrane including mobile portions that are configured to move radially inward and radially outward corresponding to closed and open positions of a free edge of the membrane, respectively, wherein the mobile portions of the membrane reside between convergence areas of the first loop and the second loop.

The prosthetic vascular valve(s) as described herein above, wherein an outer surface of the first loop and the second loop is configured to lie on a common cylinder.

The prosthetic vascular valve(s) as described herein above, wherein the frame is made of a single piece of cut tubular material.

The prosthetic vascular valve(s) as described herein above, wherein the frame is made of two wire pieces.

The prosthetic vascular valve(s) as described herein above, wherein the membrane comprises a cross-linked mammalian tissue.

The prosthetic vascular valve(s) as described herein above, wherein the membrane is a single piece of material that does not include any seams and is made from a cylindrical piece of donor tissue that has been treated, shaped and attached to the frame.

In accordance with other embodiments, an assembly is provided, comprising: a prosthetic vascular valve including a frame with a loop section including a plurality of loops and a membrane attached to the loop section, the plurality of loops extending in an axial direction of the frame, wherein an outer surface of the plurality of loops is configured to lie on a common cylinder, the membrane including a free edge that is configured to be moveable from an open position to a closed position, wherein; a delivery system including a delivery device with a plunger, wherein the delivery device is sized to hold the prosthetic vascular valve; and a closed sterile package containing the delivery system and the prosthetic vascular valve.

The assembly as described herein above, wherein the plurality of loops of the loop section includes two to six loops.

The assemblies as described herein above, wherein at least two loops of the two to six loops of material include continuous loops.

The assemblies as described herein above, wherein the prosthetic vascular valve resides within the delivery device.

The assemblies as described herein above, wherein the membrane of the prosthetic vascular valve is residing within a liquid.

The assemblies as described herein above, wherein the membrane of the prosthetic vascular valve is not residing within a liquid.

The assemblies as described herein above, wherein the membrane does not exhibit any detectable glutaraldehyde or other fixative.

In yet another embodiment, a prosthetic vascular valve comprises: a plurality of frame members, wherein each frame member of the plurality of frame members includes a proximal end and a distal end, wherein each frame member of the plurality of frame members includes a first longitudinal branch and a second longitudinal branch, and wherein for each frame member of the plurality of frame members: a first series of circumferential branch separation distances between the first longitudinal branch and the second longitudinal branch generally increase in a distal longitudinal direction away from the proximal end and toward a first longitudinally intermediate location; and a second series of circumferential branch separation distances between the first longitudinal branch and the second longitudinal branch generally decrease in the distal longitudinal direction away from a second longitudinally intermediate location and toward the distal end; and a membrane attached to the plurality of frame members to form a plurality of membrane leaflets, wherein the plurality of membrane leaflets are configured such that upon closure of the plurality of membrane leaflets, a seal is formed from coaptation of the plurality of membrane leaflets.

The prosthetic vascular valve(s) as described herein above, wherein each frame member of the plurality of frame members is a continuous loop.

The prosthetic vascular valve(s) as described herein above, wherein at least one frame member of the plurality of frame members is not a continuous loop.

The prosthetic vascular valve(s) as described herein above, wherein the at least one frame member of the plurality of frame members comprises a strand with a first end and a second end.

The prosthetic vascular valve(s) as described herein above, wherein at least a portion of the membrane is woven on to the at least one frame member of the plurality of frame members.

The prosthetic vascular valve(s) as described herein above, wherein at least one of a plurality of longitudinally oriented strand convergence areas and/or intrastrand convergence areas subdivides each frame member of the plurality of frame members into a first longitudinal portion and a second longitudinal portion, and wherein the at least one of the plurality of longitudinally oriented strand convergence areas and/or intrastrand convergence areas corresponds to at least one of the first longitudinally intermediate location and the second longitudinally intermediate location.

The prosthetic vascular valve(s) as described herein above, wherein the first longitudinal portion is located on an upstream side of plurality of frame members, and wherein most of the plurality of the membrane leaflets are attached to the first longitudinal portion.

The prosthetic vascular valve(s) as described herein above, wherein the first longitudinal portion is located on a downstream side of the plurality of frame members, and wherein most of the plurality of the membrane leaflets are attached to the first longitudinal portion.

The prosthetic vascular valve(s) as described herein above, wherein at least one of the proximal end and the distal end of each frame member of the plurality of frame members includes a region of smaller curvature.

The prosthetic vascular valve(s) as described herein above, wherein the region of smaller curvature is an eyelet.

The prosthetic vascular valve(s) as described herein above, wherein each frame member of the plurality of frame members includes one or more eyelets angled radially inward.

The prosthetic vascular valve(s) as described herein above, wherein each frame member of the plurality of frame members includes one or more eyelets angled radially outward.

The prosthetic vascular valve(s) as described herein above, wherein each frame member of the plurality of frame members is made of a single strand of wire.

The prosthetic vascular valve(s) as described herein above, wherein the single strand of wire includes a joint.

The prosthetic vascular valve(s) as described herein above, wherein the single strand of wire does not include a joint.

The prosthetic vascular valve(s) as described herein above, wherein the plurality of frame members are made of nitinol.

The prosthetic vascular valve(s) as described herein above, wherein the plurality of frame members are made of a bio-absorbable material.

In another embodiment, a prosthetic vascular valve comprises: a frame including a loop section with one or more continuous loops of material, wherein at least one of a plurality of longitudinally oriented loop convergence areas or intraloop convergence areas subdivides the one or more continuous loops into a first longitudinal portion and a second longitudinal portion; and a membrane material interconnected to the frame, wherein the membrane material includes a plurality of moveable portions forming a plurality of valve leaflets; wherein upon closure, the plurality of valve leaflets are configured to coapt along a radial alignment coincident with at least one of the plurality of loop convergence areas or intraloop convergence areas.

The prosthetic vascular valve(s) as described herein above, wherein a loop section length of the loop section of the frame is about two to eight times greater than a width of the loop section when no incident radially directed force is acting on the frame.

The prosthetic vascular valve(s) as described herein above, wherein the one or more continuous loops of material includes a continuous loop of material cut from a tube of material.

The prosthetic vascular valve(s) as described herein above, wherein the one or more continuous loops of material includes at least two pieces of wire joined together to form a continuous loop.

The prosthetic vascular valve(s) as described herein above, wherein the one or more continuous loops of material is only a single continuous loop of material.

The prosthetic vascular valve(s) as described herein above, wherein the frame includes a strand of frame material that is not a continuous loop, and wherein the strand includes a first end and a second end.

The prosthetic vascular valve(s) as described herein above, wherein at least a portion of the membrane is woven onto the frame.

The prosthetic vascular valve(s) as described herein above, wherein membrane material is not present on the second longitudinal portions of the frame.

The prosthetic vascular valve(s) as described herein above, wherein a longitudinal end of each first longitudinal portion and a longitudinal end of each second longitudinal portion includes a region of smaller curvature.

The prosthetic vascular valve(s) as described herein above, wherein the region of smaller curvature is an eyelet.

The prosthetic vascular valve(s) as described herein above, wherein membrane material interconnected to the frame does not extend to a longitudinal end of each eyelet.

The prosthetic vascular valve(s) as described herein above, wherein the frame includes one or more eyelets angled radially inward.

The prosthetic vascular valve(s) as described herein above, wherein the frame includes one or more eyelets angled radially outward.

The prosthetic vascular valve(s) as described herein above, wherein the one or more loops are made of a single strand of wire.

The prosthetic vascular valve(s) as described herein above, wherein the single strand of wire includes a joint.

The prosthetic vascular valve(s) as described herein above, wherein the single strand of wire does not include a joint.

The prosthetic vascular valve(s) as described herein above, wherein the frame is made of nitinol.

The prosthetic vascular valve(s) as described herein above, wherein the frame is made of a bio-absorbable material.

In another embodiment, a prosthetic vascular valve comprises: a frame including a first frame member including a first longitudinal portion and a second longitudinal portion, and a second frame member at least partially facing the first frame member, the second frame member including a first longitudinal portion and a second longitudinal portion; a first membrane interconnected to the first longitudinal portion, the first membrane including a first free edge, the first free edge moveable from an open position to a closed position; and a second membrane interconnected to the second loop portion, the second membrane including a second free edge, the second free edge moveable from an open position to a closed position; wherein at least a portion of the first membrane apposes at least a portion of the second membrane when the first membrane is in the closed position and the second membrane is in the closed position.

The prosthetic vascular valve(s) as described herein above, wherein the first and second frame members each form a continuous loop.

The prosthetic vascular valve(s) as described herein above, wherein the first frame member forms a continuous loop and the second frame member does not form a continuous loop.

The prosthetic vascular valve(s) as described herein above, wherein neither the first frame member nor the second frame member form a continuous loop.

The prosthetic vascular valve(s) as described herein above, wherein at least a portion of the membrane is woven onto at least one of the second frame member.

The prosthetic vascular valve(s) as described herein above, wherein membrane material is not present on the second longitudinal portions of the frame.

The prosthetic vascular valve(s) as described herein above, wherein a proximal end of the first and second frame members and a distal end of the first and second frame members each include an eyelet.

The prosthetic vascular valve(s) as described herein above, wherein membrane material interconnected to the first and second frame members does not extend to a longitudinal end of each eyelet.

The prosthetic vascular valve(s) as described herein above, wherein a distal end of each of the first and second frame members includes an eyelet.

The prosthetic vascular valve(s) as described herein above, wherein the eyelets are angled radially inward.

The prosthetic vascular valve(s) as described herein above, wherein the eyelets include a pointed tip.

The prosthetic vascular valve(s) as described herein above, wherein the pointed tip is angled radially outward.

The prosthetic vascular valve(s) as described herein above, wherein the first and second frame members are made of nitinol.

The prosthetic vascular valve(s) as described herein above, wherein the first and second frame members are made of bio-absorbable material.

In another embodiment, a prosthetic vascular valve comprises: a frame that is collapsible and expandable, the frame including a multi-lobe upstream frame portion, wherein the frame forming the multi-lobe upstream frame portion includes at least one opening such that the frame does not form a closed loop, and a downstream frame portion connected to the multi-lobe upstream frame portion; and a membrane attached to the multi-lobe frame such that the multi-lobe frame is woven through the membrane, the membrane including a free edge configured to be moveable from an open position to a closed position, wherein at least a first portion of the membrane is configured to appose at least a second portion of the membrane when the free edge is in the closed position.

The prosthetic vascular valve(s) as described herein above, wherein the multi-lobe upstream frame portion includes two lobes.

The prosthetic vascular valve(s) as described herein above, wherein the multi-lobe upstream frame portion includes three lobes.

The prosthetic vascular valve(s) as described herein above, wherein membrane material is not present on the downstream frame portion.

The prosthetic vascular valve(s) as described herein above, wherein at least one lobe of the multi-lobe upstream frame portion includes an eyelet.

The prosthetic vascular valve(s) as described herein above, wherein the membrane material does not extend to a longitudinal end of each eyelet.

The prosthetic vascular valve(s) as described herein above, wherein at least one eyelet located at a distal end of the frame includes a pointed tip.

The prosthetic vascular valve(s) as described herein above, wherein the pointed tip is angled radially outward.

The prosthetic vascular valve(s) as described herein above, wherein frame is made of nitinol.

The prosthetic vascular valve(s) as described herein above, wherein the frame is made of bio-absorbable material.

In another embodiment, a prosthetic vascular valve comprises: a frame including only a single strand of material formed into a four-lobe structure, the four-lobe structure including a pair of upstream portions and a pair of downstream portions, wherein the pair of upstream portions are offset circumferentially relative to the pair of downstream portions; and a membrane material interconnected to the frame, wherein the membrane material includes a moveable portion configured for forming a membrane closure.

The prosthetic vascular valve(s) as described herein above, wherein the single strand of material forms a single continuous loop.

The prosthetic vascular valve(s) as described herein above, wherein the membrane material is not present on the pair of downstream portions of the frame.

The prosthetic vascular valve(s) as described herein above, wherein a proximal end of each upstream portion of the pair of upstream portions and a distal end of each downstream portion of the pair of downstream portions includes an eyelet.

The prosthetic vascular valve(s) as described herein above, wherein membrane material interconnected to the frame does not extend to a longitudinal end of each eyelet.

The prosthetic vascular valve(s) as described herein above, wherein the frame includes one or more eyelets angled radially inward.

The prosthetic vascular valve(s) as described herein above, wherein the frame includes one or more eyelets angled radially outward.

The prosthetic vascular valve(s) as described herein above, wherein the frame is made of nitinol.

The prosthetic vascular valve(s) as described herein above, wherein the frame is made of a bio-absorbable material.

In another embodiment, a prosthetic vascular valve comprises: a frame including a first strand, wherein a first strand proximal end includes a first opening, and wherein a first strand distal end includes a first narrowing eyelet, and a second strand, wherein a second strand proximal end includes a second opening, and wherein a second strand distal end includes a second narrowing eyelet; and a membrane interconnected to the first strand and the second strand, the membrane including a free edge that is configured to be moveable from an open position to a closed position, wherein the membrane is woven onto the first strand and the second strand.

The prosthetic vascular valve(s) as described herein above, wherein the frame further includes a third strand, and wherein a third strand proximal end includes a third opening, and wherein a third strand distal end includes a third narrowing eyelet.

The prosthetic vascular valve(s) as described herein above, wherein the free edge of the membrane is positioned longitudinally at an upstream portion of the frame.

The prosthetic vascular valve(s) as described herein above, wherein the free edge of the membrane is positioned longitudinally within an interior of, that is, between the proximal end and the distal end of the frame.

The prosthetic vascular valve(s) as described herein above, wherein the free edge of the membrane is positioned at a downstream portion of the frame.

The prosthetic vascular valve(s) as described herein above, wherein the membrane is formed of a single piece of material.

The prosthetic vascular valve(s) as described herein above, wherein the first narrowing eyelet and the second narrowing eyelet are angled radially inward.

The prosthetic vascular valve(s) as described herein above, wherein at least one of the first narrowing eyelet and the second narrowing eyelet include a pointed tip.

The prosthetic vascular valve(s) as described herein above, wherein the first narrowing eyelet and the second narrowing eyelet each include a pointed tip.

The prosthetic vascular valve(s) as described herein above, wherein at least one of the pointed tips of the first narrowing eyelet and the second narrowing eyelet are angled radially outward and are configured to act as a retention barb.

The prosthetic vascular valve(s) as described herein above, wherein the membrane is a single piece of material that does not include any seams and is made from a cylindrical piece of donor tissue that has been treated, shaped and attached to the frame.

The prosthetic vascular valve(s) as described herein above, wherein the frame is made of nitinol.

The prosthetic vascular valve(s) as described herein above, wherein the frame is made of bio-absorbable material.

A device for implantation in the vein of a patient with multiple valves is also described, the device comprising: a first frame segment including a first frame and a first membrane valve attached to the first frame; and a second frame segment linked by a linkage to the first frame segment, the second frame segment including a second frame and a second membrane valve attached to the second frame.

The device(s) as described herein above, wherein the linkage comprises at least a strand of wire, wherein the strand of wire interconnects a distal end of the first frame segment to a proximal end of the second frame segment.

The device(s) as described herein above, wherein at least one the first frame and the second frame include one or more continuous loops.

The device(s) as described herein above, wherein at least one of the first frame and the second frame include a strand of material with a joint.

The device(s) as described herein above, wherein at least one of the first frame and the second frame include a strand of material without a joint.

The device(s) as described herein above, wherein the first membrane valve includes a moveable free edge located along a downstream portion of the first frame.

The device(s) as described herein above, wherein the first membrane valve includes a moveable free edge located between the proximal tip and distal tip of the first frame.

The device(s) as described herein above, wherein at least one of the first and second frames are made of nitinol.

The device(s) as described herein above, wherein at least one of the first and second frames are made of bio-absorbable material.

A method of making a prosthetic vascular valve is also described, the method comprising: forming frame that is collapsible and expandable; and weaving at least a portion of a membrane on to the frame by causing a first end of the frame to pass through at least two openings within the membrane; wherein the membrane includes a free edge that is configured to be moveable from an open position to a closed position.

The method(s) as described herein above, wherein the frame includes at least two strands, wherein at least one strand of the at least two strands includes the first end and a second end.

The method(s) as described herein above, wherein the frame includes at least two strands, wherein the second strand includes a first end and a second end.

The method(s) as described herein above, wherein the frame includes at least three strands, wherein the third strand includes a first end and a second end.

The method(s) as described herein above, wherein the frame includes at least one eyelet located at a distal end of the frame.

The method(s) as described herein above, wherein the at least one eyelet includes a pointed tip.

The method(s) as described herein above, further comprising the step of causing the pointed tip to be angled radially outward.

The method(s) as described herein above, wherein frame is made of nitinol.

The method(s) as described herein above, wherein the frame is made of bio-absorbable material.

In yet another embodiment, a method of making a prosthetic vascular valve is described, comprising: cutting a frame from a tube of material, wherein the frame is collapsible and expandable, and wherein the frame has a length that is about two to eight times greater than a width of the frame with no incident radially directed force acting on the frame; an attaching a membrane on to the frame; wherein the membrane includes a free edge that is configured to be moveable from an open position to a closed position.

The method(s) as described herein above, wherein the tube is a metal alloy.

The method(s) as described herein above, wherein the metal alloy is nitinol, and the method further includes heat setting the frame in between cutting the frame and attaching the membrane.

The method(s) as described herein above, wherein the frame includes two loops with first and second longitudinal portions, and wherein the membrane is attached to the first longitudinal portions.

The method(s) as described herein above, wherein the two loop portions are interconnected by a loop joining area.

The method(s) as described herein above, wherein the loop joining area is a bridging strut.

Yet a further method of making a prosthetic vascular valve is described, comprising:
manufacturing a frame, wherein the frame is collapsible and expandable, the frame including a loop section having a plurality of loops, the plurality of loops extending in an axial direction of the frame, wherein an outer surface of the plurality of loops is configured to lie on a common cylinder; and attaching a membrane on to the frame; wherein the membrane includes a free edge that is configured to be moveable from an open position to a closed position.

The method(s) as described herein above, wherein the step of manufacturing a frame comprises the step of cutting the frame from a tube of material.

The method(s) as described herein above, wherein the tube of material is a metal alloy.

The method(s) as described herein above, wherein the metal alloy is nitinol.

The method(s) as described herein above, further comprising heat setting the nitinol to a desired configuration.

The method(s) as described herein above, wherein the step of manufacturing a frame comprises the step of forming the frame from two or more pieces of wire.

The method(s) as described herein above, wherein the wire is made of nitinol.

The method(s) as described herein above, further comprising heat setting the nitinol to a desired configuration.

In another embodiment, a method of making a frame for use in manufacturing a prosthetic vascular valve is described, the method comprising: preparing a frame by one of: (a) cutting the frame from a tube of material; or (b) forming the frame from one or more pieces of wire; herein an outer surface of the plurality of loops is configured to lie on a common cylinder, and wherein the frame includes two to six loops, each loop including a first longitudinal portion and a second longitudinal portion, wherein the frame is configured to receive a membrane that includes leaflets moveable from an open position to a closed position.

The method(s) as described herein above, wherein the tube of material and the one or more pieces of wire are made of nitinol.

The method(s) as described herein above, further comprising heat setting the nitinol to a desired shape.

The method(s) as described herein above, wherein the step of heat setting further comprises placing the frame onto a mandrel and adjusting the mandrel to create the desired shape followed by raising the temperature of the frame.

Various embodiments of the one or more present inventions are set forth in the attached figures and in the Detailed Description as provided herein and as embodied by the claims. It should be understood, however, that this Summary does not contain all aspects and embodiments of the one or more present inventions, is not meant to be limiting or restrictive in any manner, and that the inventions as disclosed herein are understood by those of ordinary skill in the art to encompass obvious improvements and modifications thereto.

Additional advantages of the one or more present inventions will become readily apparent from the following discussion, particularly when taken together with the accompanying drawings.

BRIEF DESCRIPTION OF THE DRAWINGS

To assist with clarifying the advantages and features of the one or more present inventions, a more particular description of the one or more present inventions is rendered by reference to specific embodiments thereof which are illustrated in the appended drawings. It should be appreciated that these drawings depict only typical embodiments of the one or more present inventions and are therefore not to be considered limiting in scope. Embodiments of the one or more present inventions are described and explained with additional specificity and detail through the use of the accompanying drawings in which:

FIG. 19 is an embodiment of a delivery device and a prosthetic vascular valve loaded within the delivery device;

FIG. 20 is an embodiment of a delivery system being used to deploy a prosthetic valve into a vein or other fluid carrying vessel;

The drawings are not necessarily drawn to scale.

DETAILED DESCRIPTION

One or more embodiments of the one or more present inventions are directed to an implantable device comprising a prosthetic vascular valve for addressing venous insufficiency and/or other fluid related issues in the vasculature. Such devices facilitate improved blood flow for the patient, at least within a portion of the immediate vicinity of the implanted device. Where medically indicated, multiple prosthetic vascular valves may be implanted along a length of a patient's vein.

Figure 1:
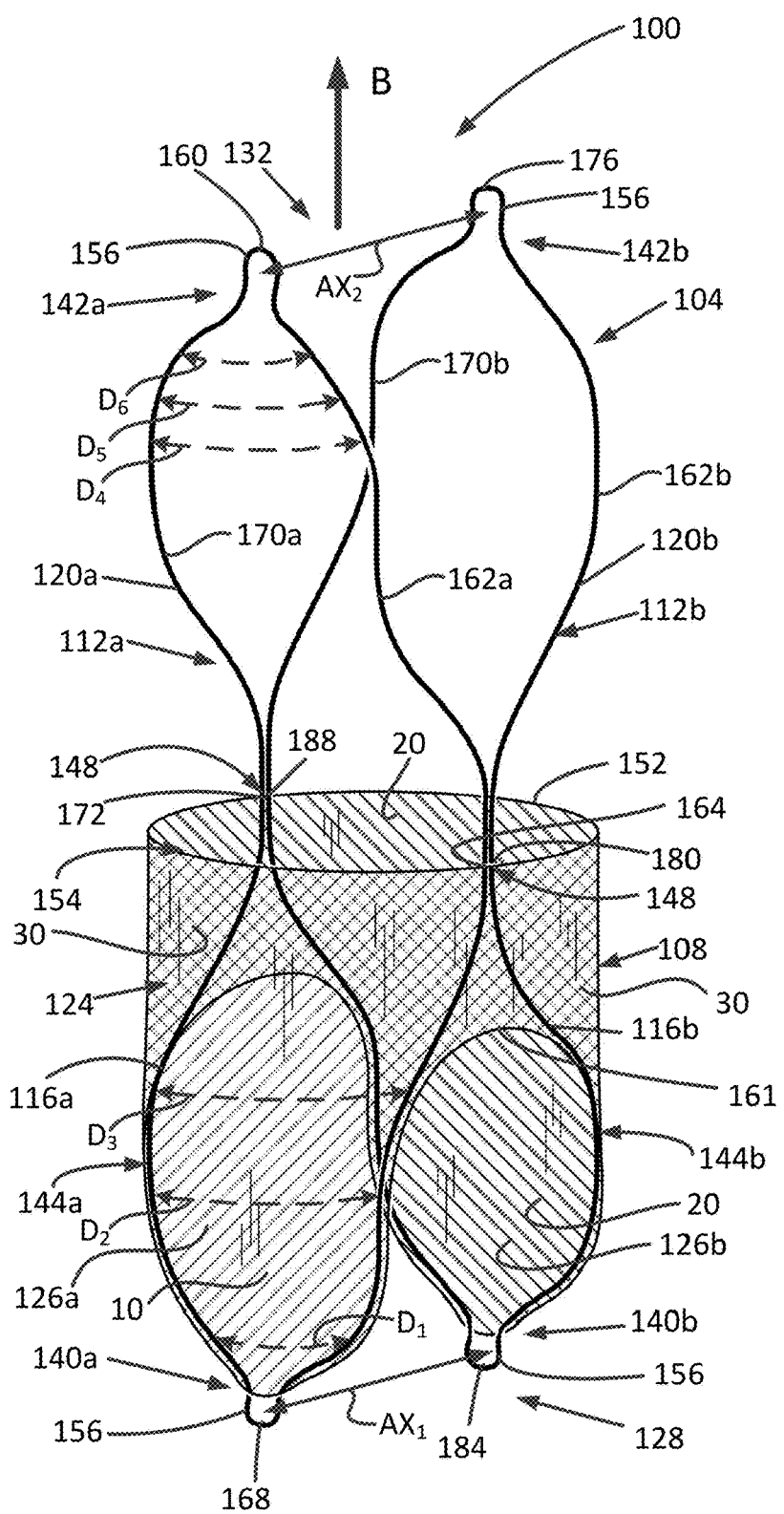
FIG. 1 is a side perspective view of an embodiment of a prosthetic vascular valve.

Referring now to FIG. 1, in at least one embodiment a prosthetic vascular valve 100 includes a wire structure or frame 104 and a dynamic liquid barrier 108 attached to the frame 104. The frame 104 includes a plurality of loops, such as two loops 112a and 112b, wherein first loop 112a is situated directly opposite to second loop 112b. Indeed, it can be seen in FIG. 1 that an axis $AX_1$ through the proximal end of the first and second loops 112a, 112b is substantially in parallel alignment with an axis $AX_2$ at the distal end of the first and second loops 112a, 112b.

For the example embodiment illustrated in FIG. 1, the first loop 112a and the second loop 112b each include a first longitudinal portion 116a, 116b and a second longitudinal portion 120a, 120b, respectively. The first longitudinal portions 116a, 116b are each operatively associated with the dynamic liquid barrier 108 that, preferably, may take the form of a membrane 124. As described in more detail below, other embodiments include different membrane configurations, such as valve configurations wherein the membrane is attached to the distal portions of the frame.

As described in detail below, the membrane is a suitable material that can serve to form a valve that can open and close. By way of example, the membrane may be a treated tissue, such as cross-linked mammalian membrane tissue, to include pericardia from a mammal. When viewed from the side, the treated tissue is mostly transparent. Accordingly, when attached to a frame a person can easily see the frame through the treated tissue. Therefore, the figures presented herein illustrate the membrane with slight shading because the membrane is only slightly opaque. For the figures presented herein that include a membrane 124, the shading has been coordinated to reflect the view as perceived by the person reviewing the drawings. More particularly, the figures illustrate the membrane outer surface 10 facing the viewer, the membrane inner surface 20 facing the viewer, and multiple layers of membrane 30 overlapped in projection (that is, a first layer of membrane with a second layer behind the first layer). Such shading is consistently used for the drawings provided herein to provide the reader with a better visual understanding of the membrane attached to the frame. Here, it is noted that the membrane 124 shown in FIG. 1 resides radially exterior to the frame 104. However, the prosthetic vascular valve 100 could be made with the membrane positioned on the interior of the frame 104.

Figure 2:
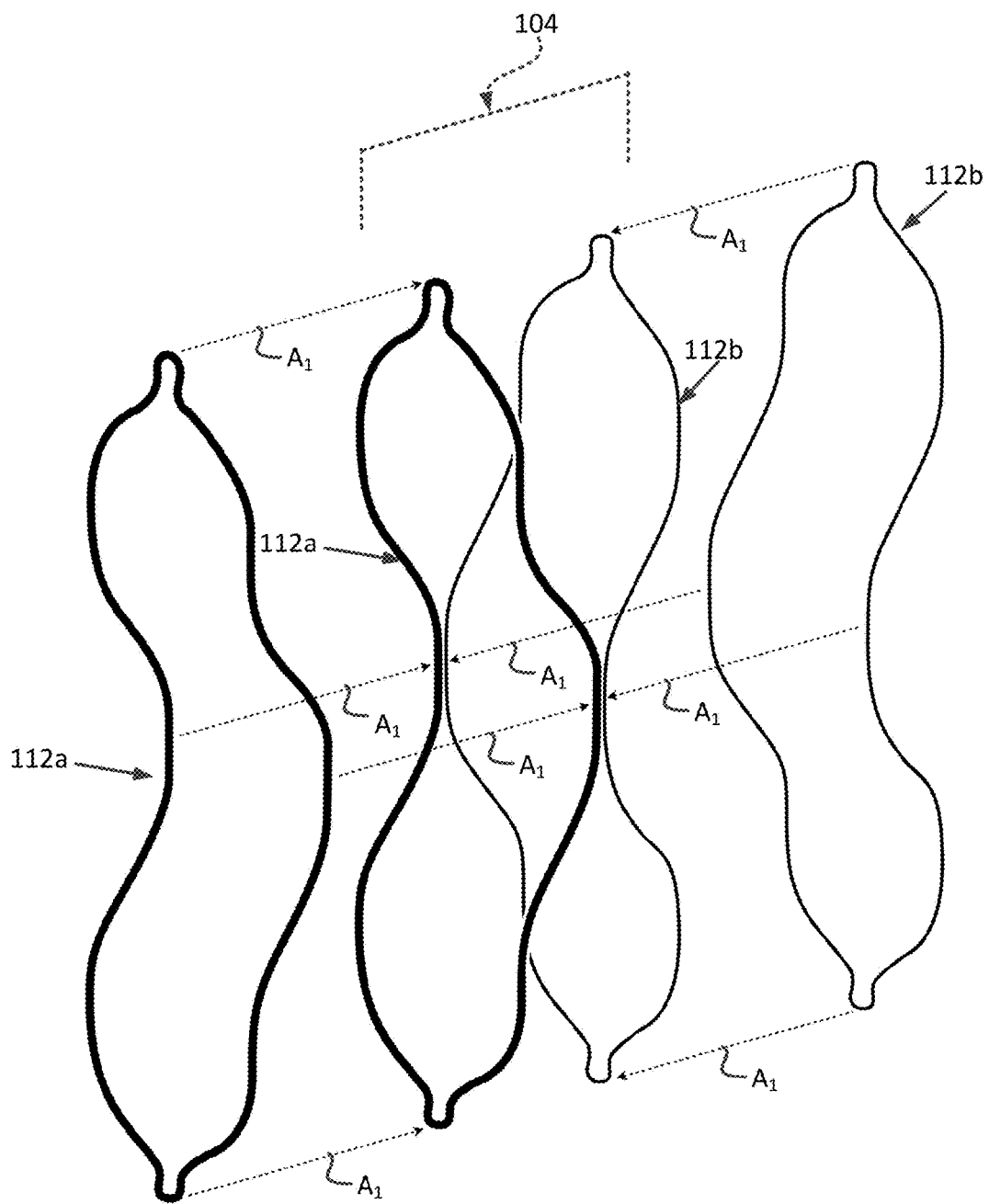
FIG. 2 is a perspective exploded view of the frame members forming the frame of the prosthetic vascular valve illustrated in FIG. 1.

Referring now to FIG. 2, the elements of frame 104 are depicted in an exploded view and an assembled view. More particularly, first loop 112*a* (in bold line weight) is shown on the left-most side of FIG. 2, with second loop 112*b* (in regular line weight) shown on the right-most side of FIG. 2. When physically brought together, such as is indicated by the dashed arrows $A_1$, the first and second loops 112*a*, 112*b* of the frame 104 can be seen in the positions they possess to form the frame 104 (without the membrane 124 attached to the frame 104).

Referring now to FIG. 3, again the elements of frame 104 are depicted in exploded view and an assembled view. The first loop 112*a* is shown on the left-most side of FIG. 3, with second loop 112*b* shown on the right-most side of FIG. 3. When brought together, again as is indicated by the dashed arrows $A_1$, and with the addition of the membrane 124, the elements of the prosthetic vascular valve 100 are seen as assembled, omitting any sutures and/or fasteners. As those skilled in the art will appreciate, the membrane 124 is attached to the first and second loops 112*a*, 112*b*, such as by suturing or other means. The center portion of FIG. 3 thus illustrates the prosthetic vascular valve 100 as shown in FIG. 1.

Figure 4:
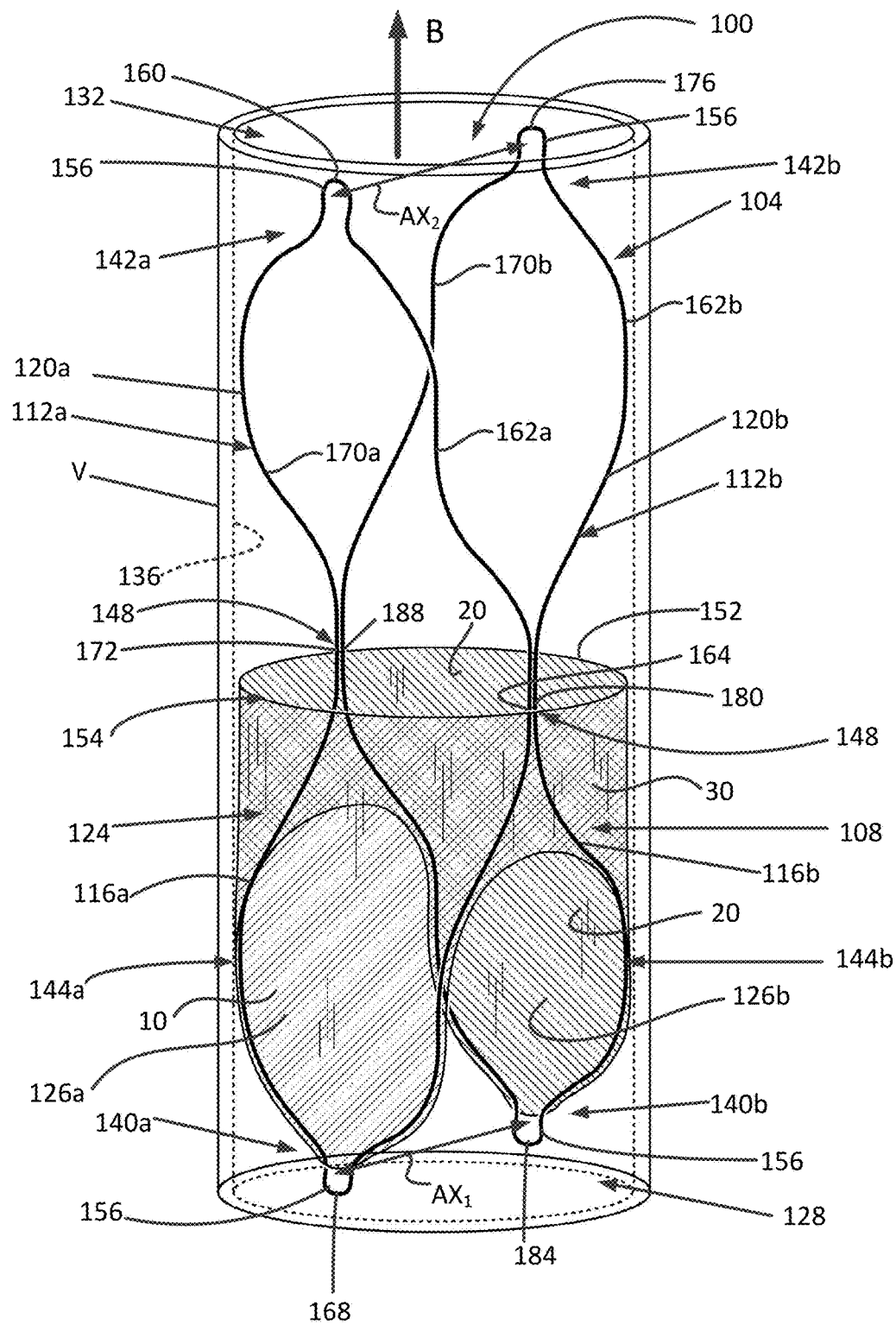
FIG. 4 is a side perspective view of the open prosthetic vascular valve of FIG. 1, wherein the prosthetic vascular valve is situated within a section of a vein and the membrane is open.

Referring now to FIGS. 1 and 4, each of the first loop 112*a* and the second loop 112*b* of the frame 104 generally extend longitudinally from the proximal end 128 (the upstream end) to the distal end 132 (the downstream end, where the direction of blood flow B is illustrated) of the prosthetic vascular valve 100 and form a continuous loop. The structure of each of the first loop 112*a* and the second loop 112*b* thereby provide a smooth and curving transition along the longitudinal length of the prosthetic vascular valve 100. As a result of its shape, the frame 104 provides a structure for holding portions of the membrane 124 attached to the first longitudinal portions 116*a*, 116*b* against the inner surface 136 of the vein V, thereby limiting or mitigating paraprosthetic leakage around the prosthetic vascular valve 100. In addition, in at least some embodiments at least some of the second longitudinal portions 120*a*, 120*b* of the frame 104, and more preferably most of the second longitudinal portions 120*a*, 120*b* are configured to contact the inner surface 136 of the vein V to further assist in holding the prosthetic vascular valve 100 in place within the vein V. Accordingly, in at least some embodiments, most of the frame 104 is configured to contact the inner surface 136 of the vein V and/or cause portions of the membrane 124 to contact the inner surface 136 of the vein V once the prosthetic vascular valve is deployed in the vein V. As those skilled in the art will appreciate, this assists in maintaining the position of the prosthetic vascular valve 104 in the vein V.

Still referring to FIGS. 1 and 4, the first and second loops 112*a*, 112*b* are arranged such that neighboring portions of each of the first and second loops 112*a*, 112*b* reside adjacent each other at regions or positions along each of the first and second loops 112*a*, 112*b* referred to herein as a loop convergence area 148. That is, the loop convergence areas 148 of each of the first and second loops 112*a*, 112*b* are locations where the neighboring frame members converge (where "converge" herein means situated adjacent, substantially adjacent, touching or joined together).

The first longitudinal portions 116*a*, 116*b* of each of the first and second loops 112*a*, 112*b* preferably include longitudinally extensive contact zones or engagement areas 144*a*, 144*b* for engaging the inner surface 136 of the vein V. In at least one embodiment, the engagement areas 144*a*, 144*b* cause the membrane 124 to contact or reside substantially adjacent to the neighboring portion of the inner surface 136 of the vein V. In at least one embodiment the entire extent of each frame loop is configured so that the radially outer surface will contact the inner surface of the blood vessel. Such contact aids in mitigating regurgitation flow around the valve 100 by limiting or preventing leakage along the inner surface 136 of vein V radially adjacent the first longitudinal portions 116*a*, 116*b*. The engagement areas 144*a*, 144*b* preferably extend longitudinally along the first longitudinal portions 116*a*, 116*b* because the geometry of the first longitudinal portions 116*a*, 116*b* away from proximal tips 140*a*, 140*b* and the toward the loop convergence areas 148 maintains the first longitudinal portions 116*a*, 116*b* and/or the membrane 124 attached thereto in contact with the inner surface 136 of the vein V. In at least one embodiment, the shape of the loops 112*a* and 112*b* are designed as a curvilinear course along a cylinder such that by virtue of geometry, the frame 104 maintains wall contact within a generally cylindrical vessel, such as a vein, along the full length of the prosthetic vascular valve 100.

For at least the embodiment depicted in FIGS. 1 and 4, the loop convergence areas 148 may constitute a longitudinal limit of the membrane 124. However, this is optional, because although not required, some membrane could be attached to the second longitudinal portions 120*a*, 120*b*. That is, it will be appreciated that although a functioning valve formed of membrane is attached to the first longitudinal portions 116*a*, 116*b*, additional membrane material could also be attached to the second longitudinal portions 120*a*, 120*b*. By way of example, although not shown in the figures, one or more portions of membrane could be attached to one or both of the second longitudinal portions 120*a*, 120*b* at a point that is spaced apart from the free edge 152 of the membrane 124 depicted in FIG. 1. For the embodiment shown in FIG. 1 with the membrane 124 ending at the loop convergence areas 148, such shape at the loop convergence areas 148 permits the free edge 152 of the membrane 124 to generally align, such that membrane material near the free edge 152 thereby forms a seal because of coaptation of the membrane material of adjacent leaflets, thus limiting the flow through the prosthetic vascular valve 100 when the valve is closed.

Figure 5:
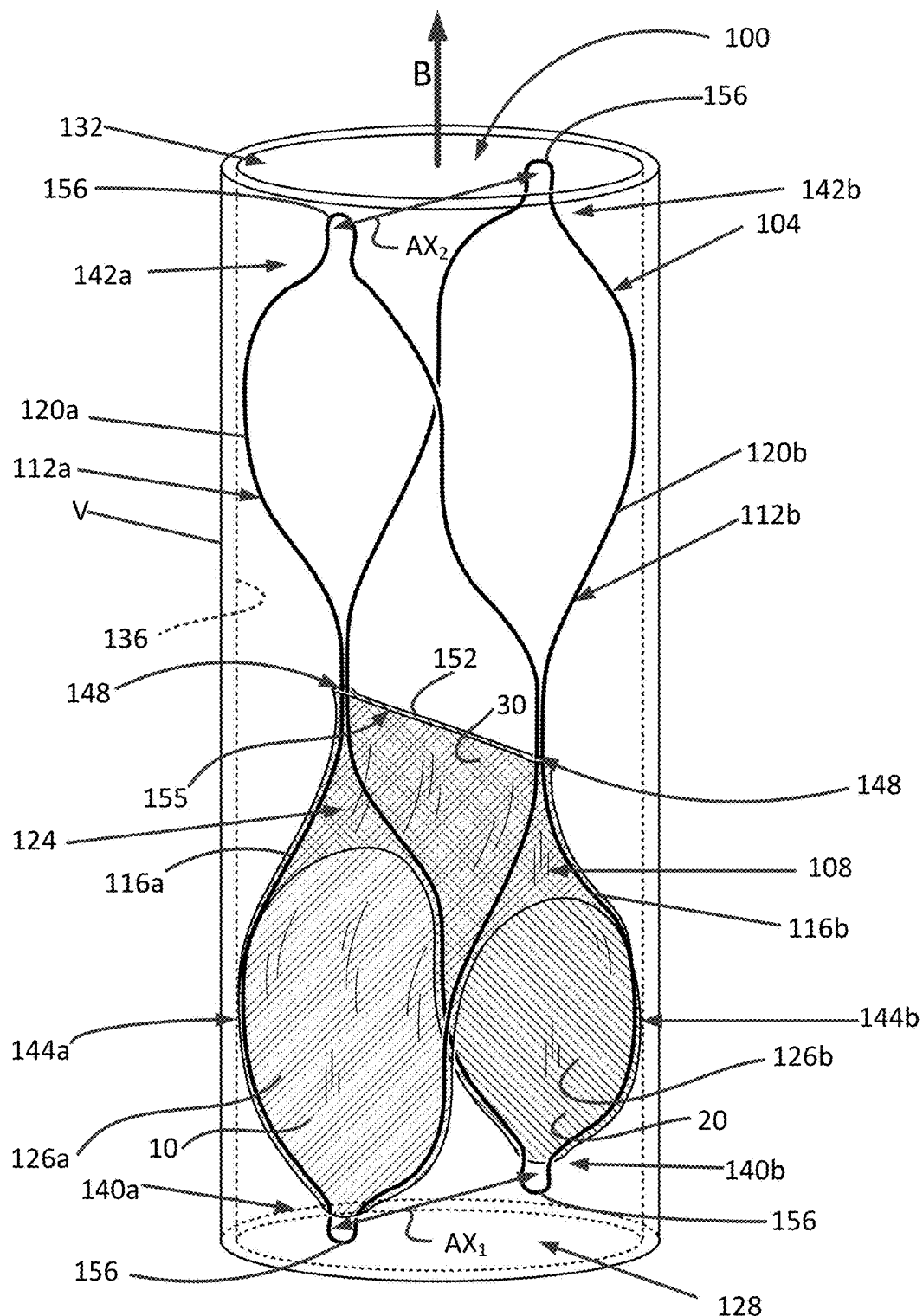
FIG. 5 is a side perspective view of the prosthetic vascular valve shown in FIG. 1 with the membrane closed.

As best seen in FIG. 1, prosthetic vascular valve 100 is configured to allow the free edge 152 of the membrane 124 to move from a first radially outward and open position 154, which allows blood flow through the prosthetic vascular valve 100, to a radially interior or closed position 155, as best seen in FIG. 5. When the free edge 152 of the membrane 124 is in the closed position 155, the prosthetic vascular valve 100 mitigates or prevents regurgitation. The free edge 152 of the membrane 124, therefore, cycles from an open position 154 to a closed position 155, thereby allowing blood to advance through the prosthetic vascular valve 100 in the open position 154, but limits or prevents regurgitation of blood when the free edge 152 of the membrane moves to the closed position 155. As those skilled in the art will appreciate, the membrane 124 acts in two different ways to limit or prevent regurgitation of blood when in the closed position 155: (1) the membrane contacts the inner surface 136 of the vein V, thus forming a seal to mitigate retrograde flow along the inner surface 136 of the vein V; and (2) the leaflets of the membrane 124 adjacent the free edge 152 are generally in a position of coaptation between the location of loop convergence areas 148 forming a seal along the diameter of the vein V, thereby limiting or preventing blood from flowing back through the prosthetic vascular valve 100. The membrane may be configured in ways that advantageously affect the manner, extent and shape of the coaptation, that is, the contact areas of the free edges of the leaflet domains of the membrane. For example, the circumference of the free edge of the membrane may exceed that of the outer frame surface so as to increase the radially inward projected length of the leaflet in closing and thereby increase the contacting areas of each leaflet to the others. In at least one other embodiment the free edge of each leaflet is shaped in a curve such as a parabola or in straight sections so as to increase the coapting contact area preferentially at the central coaptation point.

In at least one embodiment, the membrane 124 includes an arcuate-shaped proximal edge 161 located proximal to, and spaced apart from the loop convergence areas 148. More particularly, in order to prevent or limit retrograde flow back through a prosthetic vascular valve 100, the membrane material 124 preferably extends along some longitudinal length of the prosthetic vascular valve 100. The arcuate-shaped proximal edge 161 limits the amount of forward flowing vascular liquids that can be impeded or stopped by the proximal edge of the membrane.

Both the first longitudinal portions 116a, 116b and the second longitudinal portions 120a, 120b of the frame 104 accommodate radial compression of the vein V that may occur by external compressive force around the prosthetic vascular valve 100. More particularly, the laterally compressible nature of the frame 104 permits radially inward and outward flexing of the frame 104. By way of example, the frame 104 can compress and deflect to about 5 mm in diameter, and expand to about 20 mm in diameter, and during both compression and expansion the frame can maintain contact with the inner surface 136 of the vein V, thereby providing a stable structure within the vein that is not traveling longitudinally or shifting to become crosswise within the vein. As those skilled in the art will appreciate, valves can be manufactured to a variety of sizes to accommodate the vasculature to be treated. More particularly, although one example is described above wherein the frame can compress and deflect to about 5 mm in diameter, and expand to about 20 mm in diameter, larger or small valves can be manufactured, stored, and be readily available to accommodate a patient's needs. The prosthetic vascular valve 100, as well as the other prosthetic vascular valves for vascular conduits described in this disclosure, can be sized to have a diameter of between about 5 mm to about 50 mm in an unloaded and uncompressed state. In use, the prosthetic vascular valve 100 can be chosen to function with a compressed diameter of between about 3 mm to about 40 mm. Thus, the prosthetic vascular valve 100 can then accommodate radially inward and outward flexing. As those skilled in the art will appreciate, the functional diameter range for a given prosthetic vascular valve would depend upon the target implantation site and the diameter of the vein to be treated.

As noted above, the loop convergence areas 148 may constitute the closest proximity between the first and second loops 112a, 112b. The first and second loops 112a, 112b may, optionally, be joined at the loop convergence areas 148 by one or more fasteners, such as a wire ring or suture that loops around each loop convergence area 148. By way of example, a first wire ring (not shown) may be located around both the first and second loops 112a, 112b at a first loop convergence area 148 and a second wire ring (not shown) may be located around both the first and second loops 112a, 112b at a second loop convergence area 148 at a position that is diametrically opposite the first loop convergence area 148. In addition, the portion of the membrane 124 associated with the first loop 112a may, optionally, be sutured at the loop convergence areas 148 to the membrane 124 associated with the second loop 112b.

Referring still to FIGS. 1-5, the second longitudinal portions 120a, 120b of the first and second loops 112a, 112b may substantially mirror the first longitudinal portions 116a, 116b; however, without the addition of membrane, although some membrane could be attached to the second longitudinal portions 120a, 120b provided a working valve is provided at the first longitudinal portions 116a, 116b. Accordingly, in at least some embodiments, and as discussed in detail below, the second longitudinal portions 120a, 120b contact the inner surface 136 of the vein V to provide a structure with a radially outward force for stabilizing the prosthetic vascular valve 100 against the adjacent inner surface 136 of the vein V.

Figure 18:
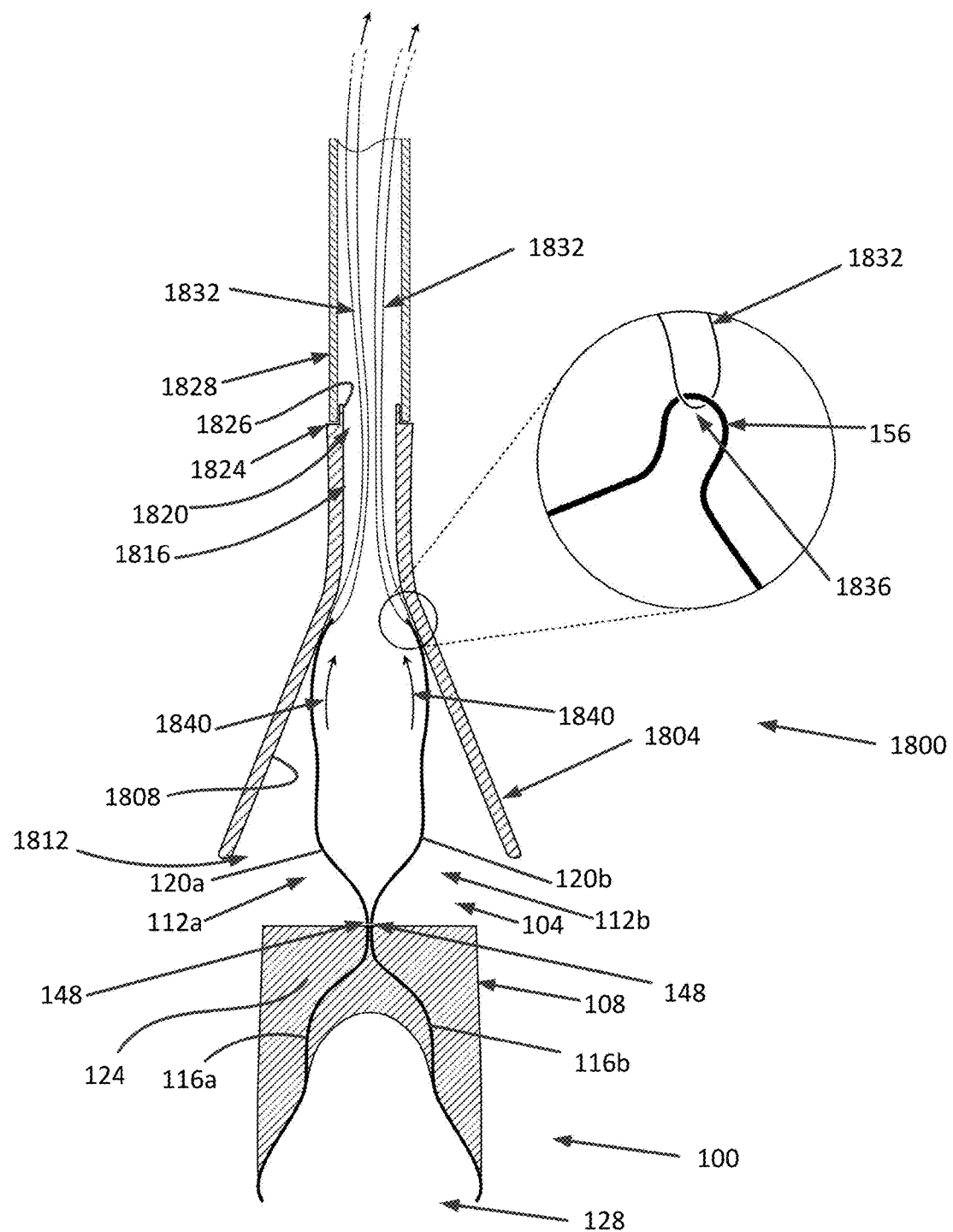
FIG. 18 is a view of a device shown in longitudinal cross section used to load a prosthetic vascular valve (shown in side elevation view) into a delivery device.

As best seen in FIGS. 1, 4 and 5, in at least one embodiment the proximal tips 140a, 140b and distal tips 142a, 142b may include a narrow extension of loop material forming an eyelet 156, as shown and described herein. It is to be understood that the term "eyelet" as used herein is a narrow extension of loop material located at a longitudinal end of a loop or strand. In at least some embodiments, and as best seen in FIG. 18 and discussed in further detail below, an eyelet 156 may be shaped to receive a hook or line for providing tension to the prosthetic vascular valve 100, thereby allowing the prosthetic vascular valve 100 to be loaded into a needle or delivery catheter for deployment and implantation in a vein of a patient. Since a hook or line may be passed through the eyelets 156 during loading the prosthetic vascular valve 100 into a needle or delivery catheter, preferably the membrane lobes 126a and 126b of the membrane 124 do not extend to the ends of the eyelets 156; however, if the eyelets are not intending to be used to receive a hook or a line to assist with loading the prosthetic vascular valve into a needle or delivery catheter, then membrane material can extend to the longitudinal end of such a loop, including an eyelet 156, if present. In general, and in particular to the case wherein loops 112a and 112b are constituted of shape memory alloy, eyelets 156 are set in the shape setting process of the loop material and provide necessary strain relief to permit the sharp reversal in the course of the material, facilitating radial compression with reduced force and insertion of the device into a delivery catheter without fracturing.

Figure 3:
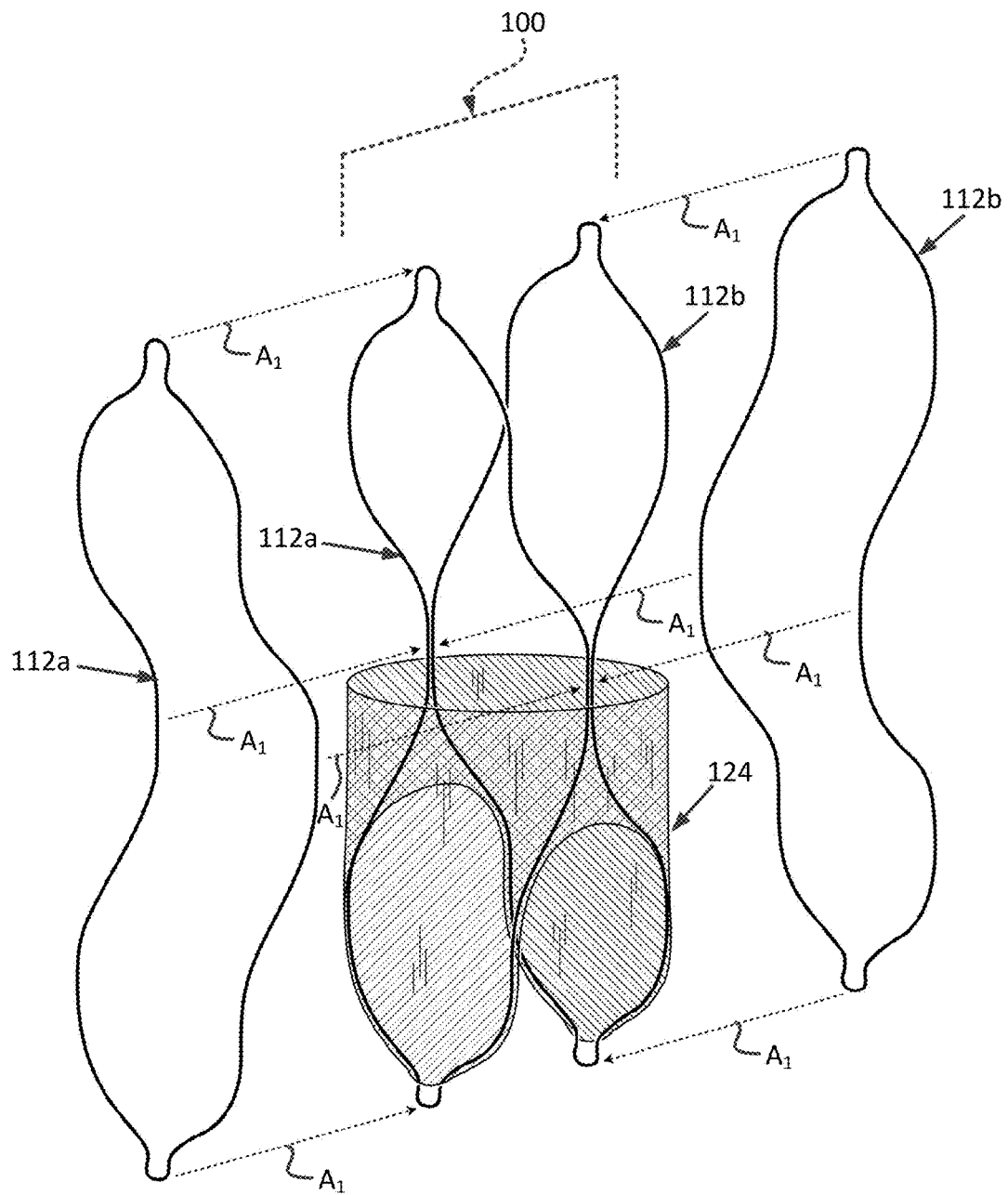
FIG. 3 is an additional perspective exploded view of the frame members and membrane forming the prosthetic vascular valve illustrated in FIG. 1.
Figure 6:
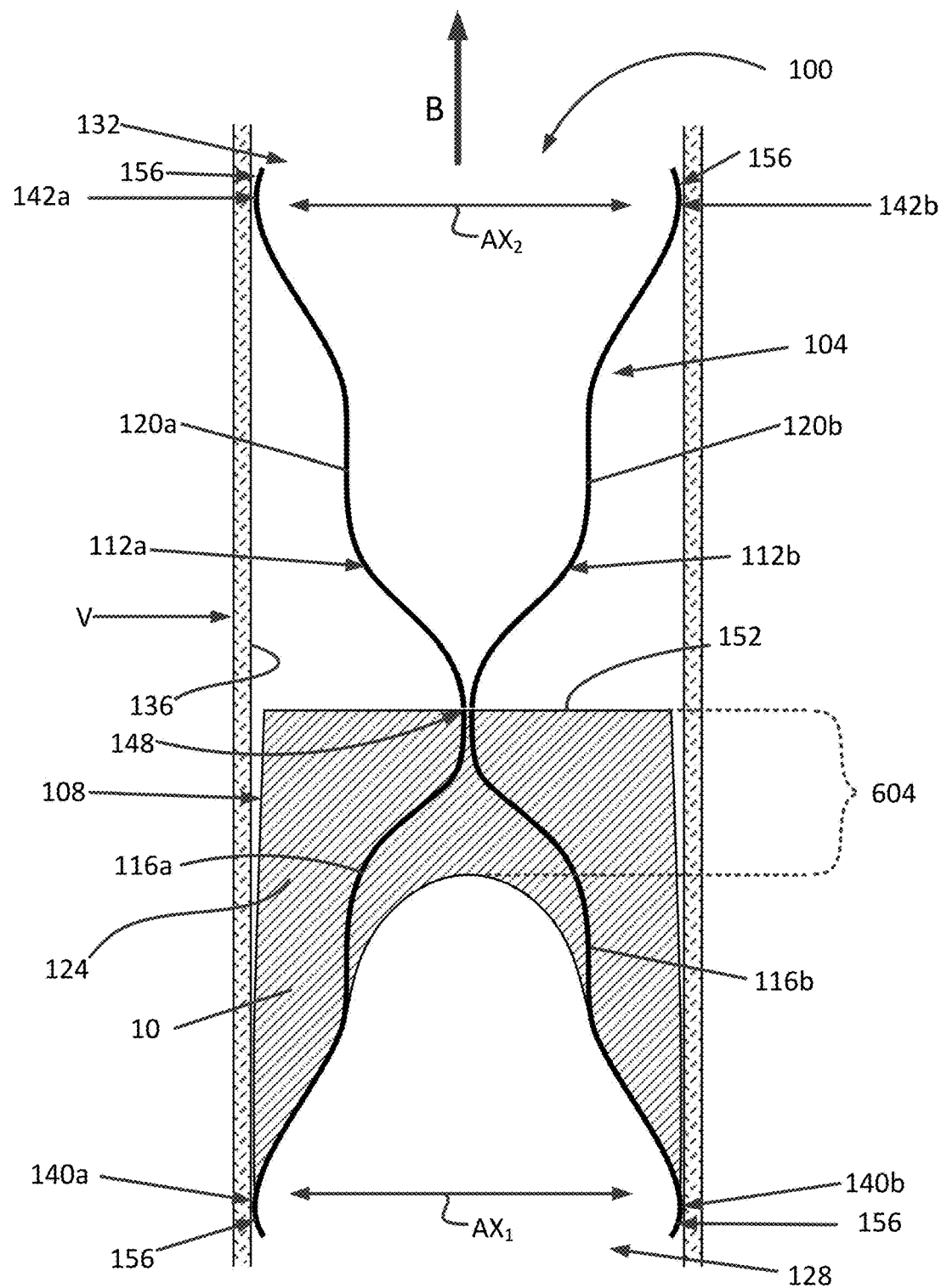
FIG. 6 is a longitudinal side elevation view of the device shown in FIG. 1.

As best seen in the longitudinally-oriented cross-sectional view of FIG. 6, the membrane 124 may include a cylindrically-shaped portion or a substantially cylindrically-shaped portion 604 that is continuous with membrane lobes 126a, 126b that are attached to the first longitudinal portions 116a, 116b, respectively, of the first loop 112a and the second loop 112b of the frame 104. Alternatively, the dynamic liquid barrier 108 may be attached in multiple pieces to the first longitudinal portions 116a, 116b of the frame 104. More particularly, a first piece of membrane may be attached to first longitudinal portion 116a and a second piece of membrane may be attached to the first longitudinal portion 116b. In yet a further alternative, multiple pieces of membrane material may be connected to collectively form a liquid barrier that operates as a valve that opens and closes. The membrane 124 with its coapting leaflets that are continuous with the membrane lobes 126a, 126b mitigates regurgitation of blood flow both through and radially adjacent to the prosthetic vascular valve 100. The downstream edge 152 of the coapting leaflet membrane may be configured with a circular edge as shown in FIGS. 1, 3 and 4, or as other polygonal or curvilinear forms. For example, each mobile leaflet portion of the membrane layer may extend axially from the center of its free edge in the shape of an isosceles triangle or a parabola so as to increase the axial coaptation length when the leaflets meet centrally in the closed operating position.

Still referring to FIG. 6, as noted above, the first and second loops 112a, 112b each include a proximal tip 140a, 140b, respectively, and a distal tip 142a, 142b, respectively. In at least one embodiment, and as best seen in FIG. 6, both the proximal tips 140a, 140b and the distal tips 142a, 142b of the frame 104 may be slightly angled radially interior to, and away from, the inner surface 136 of the vein V when in place. Advantageously, this assists with positioning the prosthetic vascular valve 100 upon deployment, because the inward curving tips aid in compression of the vascular valve into the delivery catheter.

In at least one embodiment, and for ease of construction, each of the first and second loops 112a and 112b may be substantially the same size, and as described above, the first longitudinal portions 116a, 116b may be the mirror image of the second longitudinal portions 120a, 120b. Alternatively, in accordance with at least one embodiment, the first longitudinal portions 116a, 116b may be longer in longitudinal length than the second longitudinal portions 120a, 120b. In a further alternative, and in accordance with at least one embodiment, the first longitudinal portions 116a, 116b may be shorter in longitudinal length than the second longitudinal portions 120a, 120b.

In at least one embodiment, the first longitudinal portions 116a, 116b and the second longitudinal portions 120a, 120b, respectively, are both substantially aligned to face one another and with substantially parallel axes $AX_1$ and $AX_2$ passing through the eyelets 156 of each first longitudinal portions 116a, 116b and the second longitudinal portions 120a, 120b.

Upon deployment in the vein V of a patient, each of the prosthetic vascular valves disclosed herein are stationary or substantially stationary in the longitudinal direction of the vein within which they are deployed (although the dynamic liquid barrier 108 attached to the frame 104, such as a membrane 124, opens and closes). More particularly, the prosthetic vascular valves remain stationary or substantially stationary in the vein V where deployed, such as by contacting the inner surface 136 of the vein V such that the frame 104 (and/or the membrane attached to the frame) frictionally engages the inner surface 136 of the vein V, thereby holding the prosthetic vascular valve in place. That is, the frame 104 is sized to be biased radially outward to cause the frame to contact the inner surface 136 of the vein V with sufficient force so as to maintain the position of the prosthetic vascular valve within the vein V. Alternatively, or in addition to being biased radially outward, the prosthetic vascular valves may engage the vein V using one or more barbs or similar structures forming part of the frame 104 or otherwise attached to the frame 104 (such as a barb welded to the frame 104) that frictionally contact and/or at least partially penetrate the inner surface 136 of the vein V and/or at least a portion of the wall of the vein V, thereby holding the prosthetic vascular valve in place. Alternatively yet, the prosthetic vascular valves may be tacked into position, such as by suturing during placement, to hold the prosthetic vascular valves in place within the vein V.

Figure 7:
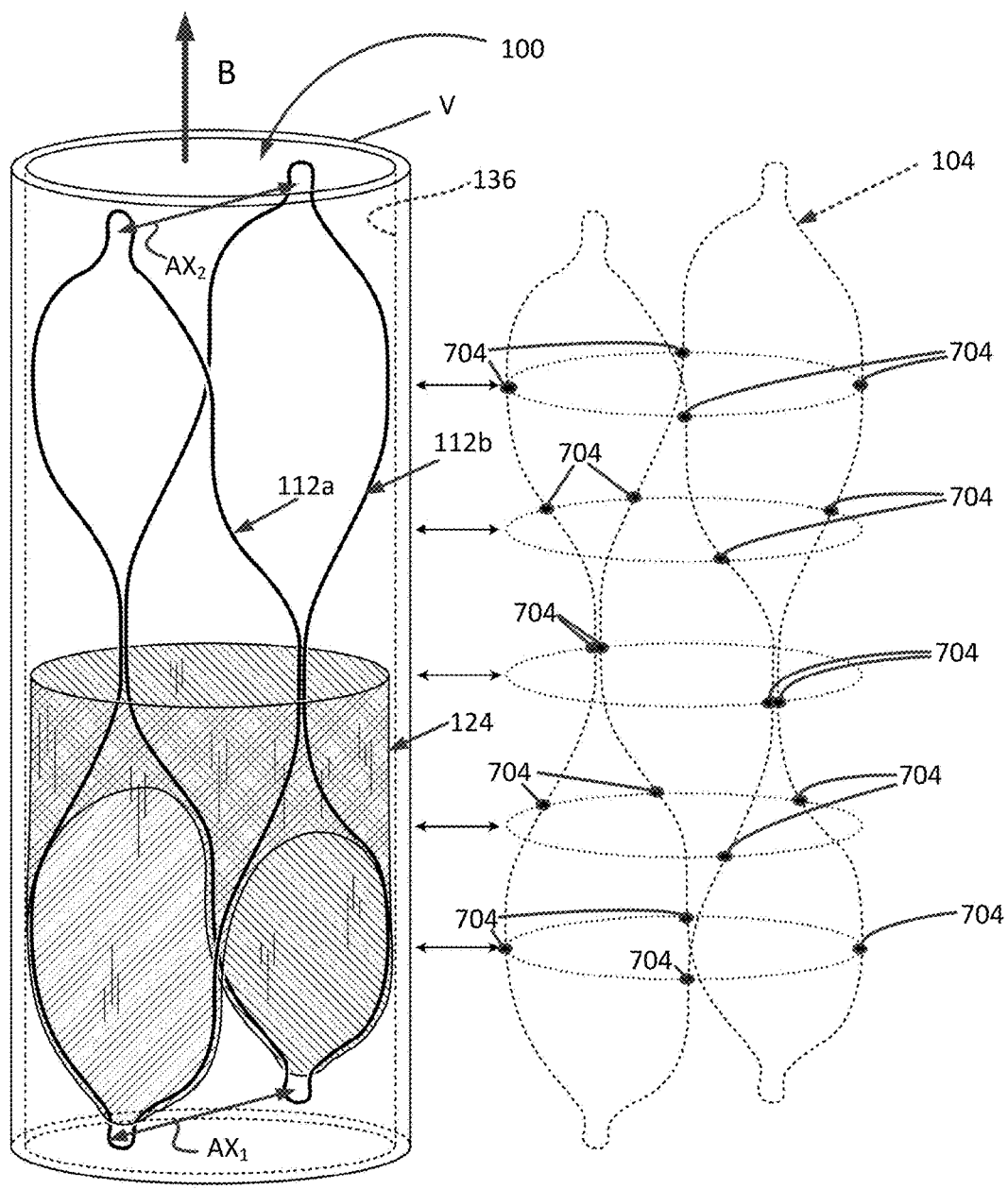
FIG. 7 is a side perspective view of the prosthetic vascular valve shown in FIG. 1, together with a rendering of a series of horizontal planes (relative to the orientation of the sheet) that pass through the prosthetic vascular valve.

With reference now to FIG. 7, it can be seen that the outline of the frame 104 extends along portions of the inner surface 136 of the vein V. Indeed, most of the length of the frame is both biased radially outward and is shaped to contact the inner surface 136 of the vein V, such that the frame 104 serves to anchor the prosthetic vascular valve within the vein V. As shown in FIG. 7, the prosthetic vascular valve 100 within vein V is shown on the left side, with the right side of the drawing depicting the frame 104 with five planar rings situated along the longitudinal length of the frame 104, wherein each planar ring is simply a graphical representation of a plane through the prosthetic vascular valve 100 each coincidentally intersecting both the frame members and the cylindrical inner surface 136 of the containing vessel V at contact points 704, thereby demonstrating that the frame members are in contact with the inner surface 136 of vein V, and that the loops 112a and 112b are shaped so that an outer surface of the loops 112a and 112b lies on a common cylinder. Multiple additional planes may be drawn showing similar disposition of contact points. Accordingly, it can be seen that the frame 104 contacts the inner surface 136 of the vein V along a majority of the longitudinal length of the frame 104, such as along greater than 50% of the longitudinal length of the frame, and more preferably greater than along 60% of the longitudinal length of the frame, and more preferably yet greater than along 70% of the longitudinal length of the frame, and still more preferably greater than along 75% of the longitudinal length of the frame, and still more preferably yet greater than along 80% of the longitudinal length of the frame, and even more preferably greater than along 85% of the longitudinal length of the frame, and still even more preferably greater than along 90% of the longitudinal length of the frame.

Referring again to FIG. 6, a side elevation view of prosthetic vascular valve 100 as shown in FIG. 4 is illustrated. As can be seen at the proximal end and distal end of the frame 104, the eyelets 156, if present, may be radially inwardly oriented. However, in at least one embodiment, the remaining portions of the frame (or substantial portions of the frame) between the eyelet 156 at the distal end and the eyelet 156 at the proximal end may be in contact (or membrane material attached thereto may be in contact) with the inner surface 136 of the vein V. That is, the frame 104 may contact different annular portions of the inner surface 136 of the vein V along the longitudinal length of the first loop 112a. Accordingly, and with reference again to FIG. 4, considering the first loop 112a, a distal end location 160 can be considered a first angular location of first loop 112a and can be assigned to a position of zero degrees (as referenced around a circumference of the vein V). A first longitudinally intermediate location 164 along the first loop 112a corresponds to a second angular location that is angularly offset approximately 90 degrees from the first angular location. The proximal end location 168 of the first loop 112a can be considered a third angular location, wherein the third angular location corresponds angularly again to the position of zero degrees. Accordingly, along the longitudinal length of a first side or first longitudinal branch 162a of the first loop 112a, the first loop 112a extends angularly from zero degrees to 90 degrees and back again to zero degrees. Still considering the first loop 112a, along a second side or second longitudinal branch 170a of the first loop 112a, a second longitudinally intermediate location 172 corresponds to a fourth angular location that is angularly offset approximately 90 degrees from the third angular location, such that the second longitudinally intermediate location 172 is angularly offset approximately 180 degrees from the first longitudinally intermediate location 164. The first loop 112a further extends longitudinally from the second longitudinally intermediate location 172 distally back to the distal end location 160. Accordingly, the first loop 112a extends angularly 180 degrees along its longitudinal length from the distal end location 160 to the proximal end location 168 along a first side or first longitudinal branch 162a, and back to the distal end location 160 along a second side or second longitudinal branch 170a of the first loop 112a. At least in some embodiments, the first loop 112a (or membrane material associated with the first loop 112a) contacts the inner surface 136 of the vein V along a majority of the first loop 112a.

With regard to the second loop 112b, in at least one embodiment, a majority of the frame (or substantial portions of the frame) between the eyelet 156 at the distal end and the eyelet 156 at the proximal end may be in contact (or membrane material attached thereto may be in contact) with the inner surface 136 of the vein V. That is, as with the first loop 112a, the second loop 112b of the frame 104 may contact different annular portions of the inner surface 136 of the vein V along the longitudinal length of the second loop 112b. More particularly, considering the second loop 112b, a distal end location 176 can be considered a first angular location of second loop 112b and can be assigned to an initial position of 180 degrees and directly opposite the initial position of the first loop 112a (as referenced around a circumference of the vein V). A first longitudinally intermediate location 180 along the second loop 112b corresponds to a second angular location that is angularly offset approximately 90 degrees from the first angular location of the second loop 112b. The proximal end location 184 of the second loop 112b can be considered a third angular location, wherein the third angular location corresponds angularly again to the initial position of 180 degrees. The proximal end location 184 of the second loop 112b is directly opposite the proximal end location 168 of the first loop 112a. Accordingly, along the longitudinal length of a first side or first longitudinal branch 162b of the second loop 112b, the second loop 112b extends angularly from 180 degrees to 90 degrees and back again to 180 degrees. Still considering the second loop 112b, along a second side or second longitudinal branch 170b of the second loop 112b, a second longitudinally intermediate location 188 corresponds to a fourth angular location of the second loop 112b that is angularly offset approximately 90 degrees from the third angular location of the second loop 112b, such that the second longitudinally intermediate location 188 is angularly offset approximately 180 degrees from the first longitudinally intermediate location 180 of the second loop 112b. The second loop 112b further extends longitudinally from the second longitudinally intermediate location 188 distally back to the distal end location 176 of the second loop 112b. Accordingly, the second loop 112b extends angularly 180 degrees along its longitudinal length from the distal end location 176 to the proximal end location 184 along a first side or first longitudinal branch 162b, and back to the distal end location 176 along a second side or second longitudinal branch 170b of the second loop 112b. At least in some embodiments, the second loop 112b (or membrane material associated with the second loop 112b) contacts the inner surface 136 of the vein V along a majority of the second loop 112b. For the prosthetic vascular valve 100 shown in FIG. 1, the second loop 112b contacts the interior of vein V opposite the first loop 112a.

Referring again to FIG. 1, six example circumferential branch separation distances $D_1$ through $D_6$ are shown. A circumferential branch separation distance is the distance between the first longitudinal branch and the second longitudinal branch of a given loop. By way of example, the circumferential branch separation distance is the circumferential distance between the first longitudinal branch 162a and the second longitudinal branch 170a of first loop 112a. In general, that is, with the exception of the eyelets 156 at each end of the loop, the circumferential branch separation distances increase between the proximal tip 140a and a longitudinally intermediate location, such as a loop convergence area 148. Thus, for the series of circumferential branch separation distances $D_1$, $D_2$, and $D_3$ shown in FIG. 1, $D_3$ is greater than $D_2$, which is greater than $D_1$. In addition, the circumferential branch separation distances decrease between a longitudinally intermediate location, such as a loop convergence area 148, and the distal tip 142a. Thus, for the series of circumferential branch separation distances $D_4$, $D_5$, and $D_6$ shown in FIG. 1, $D_4$ is greater than $D_5$, which is greater than $D_6$. The foregoing applies to both the first loop 112a and the second loop 112b. Moreover, the increases in the circumferential branch separation distances between the proximal tip and the longitudinally intermediate locations, as well as decreases in the circumferential branch separation distances between the longitudinally intermediate locations and the distal tip, also apply to other embodiments described herein.

Figure 8:
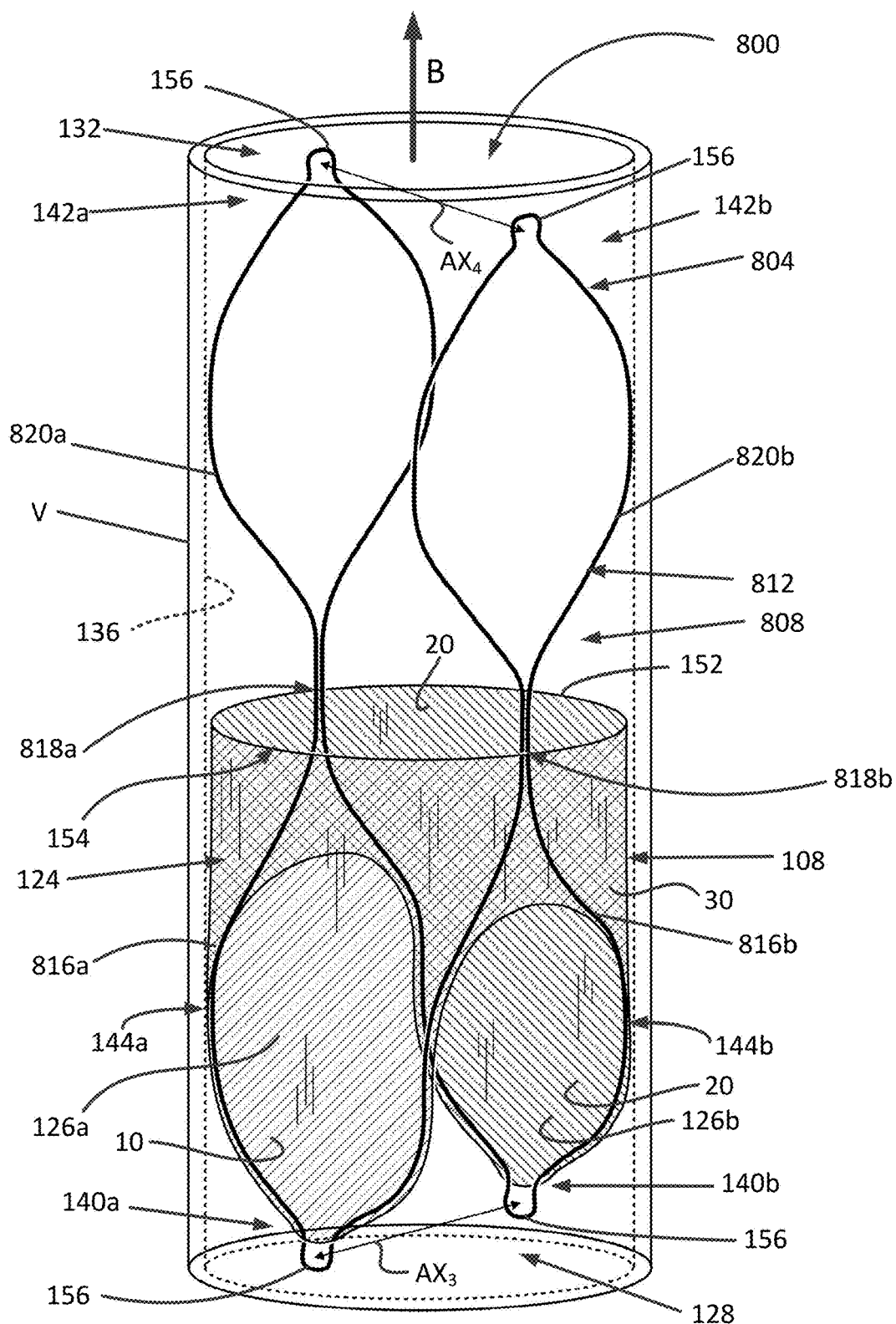
FIG. 8 is another embodiment of a prosthetic vascular valve, wherein the prosthetic vascular valve is shown situated within a section of a vein.

Referring now to FIG. 8, another embodiment of a prosthetic vascular valve 800 is shown. Prosthetic vascular valve 800 includes a frame 804 and a dynamic liquid barrier 108 attached to the frame 804. The frame 804 of the prosthetic vascular valve 800 is a four-lobe structure 808 formed of a single continuous loop 812 of material, such as a wire or tube cutting made of nitinol and formed in the desired shape. As shown in FIG. 8, the four-lobe structure 808 includes a pair of first longitudinal portions 816a, 816b and a pair of second longitudinal portions 820a, 820b. As with prosthetic vascular valve 100, the first longitudinal portions 816a, 816b are each operatively associated with a membrane 124, wherein the membrane 124 mitigates regurgitation of blood flow both through and radially adjacent to the prosthetic vascular valve 800. The prosthetic vascular valve 800 includes two intrastrand or intraloop convergence areas 818a and 818b. The intrastrand or intraloop convergence areas 818a, 818b are locations where two portions of the single continuous loop 812 are situated adjacent one another. In the case of prosthetic vascular valve 800, the intrastrand or intraloop convergence areas 818a and 818b are generally aligned diametrically opposite one another, such that the membrane free edge is also in general alignment with the intrastrand or intraloop convergence areas 818a, 818b when the membrane is closed. For the prosthetic vascular valve 800 shown in FIG. 8, no membrane functioning as a valve is connected to the second longitudinal portions 820a, 820b. However, it will be appreciated that although a functioning valve formed of membrane is attached to the first longitudinal portions 816a, 816b, and that no membrane functioning as a valve is connected to the second longitudinal portions 820a, 820b, nonetheless, additional membrane material could also be attached to the second longitudinal portions 820a, 820b, wherein, by way of example, such membrane may be optionally attached to the second longitudinal portions 820a, 820b to modify the frictional characteristics of the frame 804 contacting the inner surface 136 of the vein V.

Still referring to FIG. 8, as the single continuous loop 812 is traced, it transitions from the proximal end 128 (the upstream end) to the distal end 132 (the downstream end), back to the proximal end 128 and again back to the distal end 132. More particularly, the material forming four-lobe structure 808 extends longitudinally from a first proximal tip 140a to first intrastrand or intraloop convergence area 818a, distally to first distal tip 142a, then proximally back to first loop convergence area 818a, then further proximally to second proximal tip 140b, then distally to second loop convergence area 818b, then further distally to second distal tip 142b and then proximally back to second loop convergence area 818b, and then further proximally back to first proximal tip 140a, thereby forming the single continuous loop 812. As can be seen in FIG. 8, the first longitudinal portions 816a, 816b face one another and the second longitudinal portions 820a, 820b also face one another; however, the first longitudinal portion 816a is offset 90 degrees or about 90 degrees relative to the second longitudinal portion 820a, which is offset 90 degrees or about 90 degrees relative to the first longitudinal portion 816b, which is offset 90 degrees or about 90 degrees relative to the second longitudinal portion 820b, which is offset 90 degrees or about 90 degrees to the first longitudinal portion 816a. Such configuration advantageously provides that a single continuous loop of material can be used, thereby eliminating the need for interconnecting separate loops together to form the structure. Moreover, the outward forces associated with the first longitudinal portions 816a, 816b and the second longitudinal portions 820a, 820b that engage the inner surface 136 of the vein V do so substantially parallel to two orthogonal axes (one axis $AX_3$ through the first longitudinal portions 816a, 816b and a second axis $AX_4$ through the second longitudinal portions 820a, 820b), thereby further stabilizing the four-lobe structure 808 within the vein V. It should be appreciated that the shape of the loop 812 is designed as a curvilinear course along a cylinder such that by virtue of geometry, the frame 804 maintains wall contact within a generally cylindrical vessel, such as a vein, along the full length of the prosthetic vascular valve 800

As with prosthetic vascular valve 100, for prosthetic vascular valve 800 the first longitudinal portions 816a, 816b preferably include contact zones or engagement areas 144a, 144b for engaging the inner surface 136 of the vein V. In at least one embodiment, the engagement areas 144a, 144b cause the membrane 124 to contact or reside substantially adjacent to the neighboring portion of the inner surface 136 of the vein V. Such contact aids in mitigating regurgitation flow around the prosthetic vascular valve 800 by limiting or preventing leakage along the inner surface 136 of vein V radially adjacent the first longitudinal portions 816a, 816b. The engagement areas 144a, 144b extend longitudinally along the first longitudinal portions 816a, 816b because geometry of the first longitudinal portions 816a, 816b flares in the longitudinal direction away from proximal tips 140a, 140b and toward the intrastrand or intraloop convergence areas 818a, 818b of the prosthetic vascular valve 800, wherein the intrastrand or intraloop convergence areas 818a, 818b may constitute the downstream longitudinal limit of the membrane 124. Such shape at the loop convergence areas 818a, 818b permits the free edges 152 of the membrane 124 to form a liquid barrier upon closing of the portions of the membrane 124 situated adjacent the adjacent free edges 152 (that is, membrane material near the free edges 152) that is aligned adjacent one another, thereby forming a seal and limiting flow through the prosthetic vascular valve 800. Material forming the membrane 124 may be sutured at the intrastrand or intraloop convergence areas 818a, 818b. As shown in FIG. 8, the free edges 152 move from a first radially outward and open position 154, which allows blood flow through the prosthetic vascular valve 800, to a radially interior or closed position (similar to that shown in FIG. 5), which mitigates or prevents regurgitation.

Referring still to FIG. 8, as with prosthetic vascular valve 100, for prosthetic vascular valve 800 the proximal tips 140a, 140b and distal tips 142a, 142b may include a narrow extension of loop material or eyelet 156. Each eyelet 156 is shaped to receive a hook or line for providing tension to the valve 800 during crimping, thereby allowing the valve to be loaded into a catheter or tube for deployment and implantation in vein of a patient, such as depicted in FIG. 18.

Figure 9:
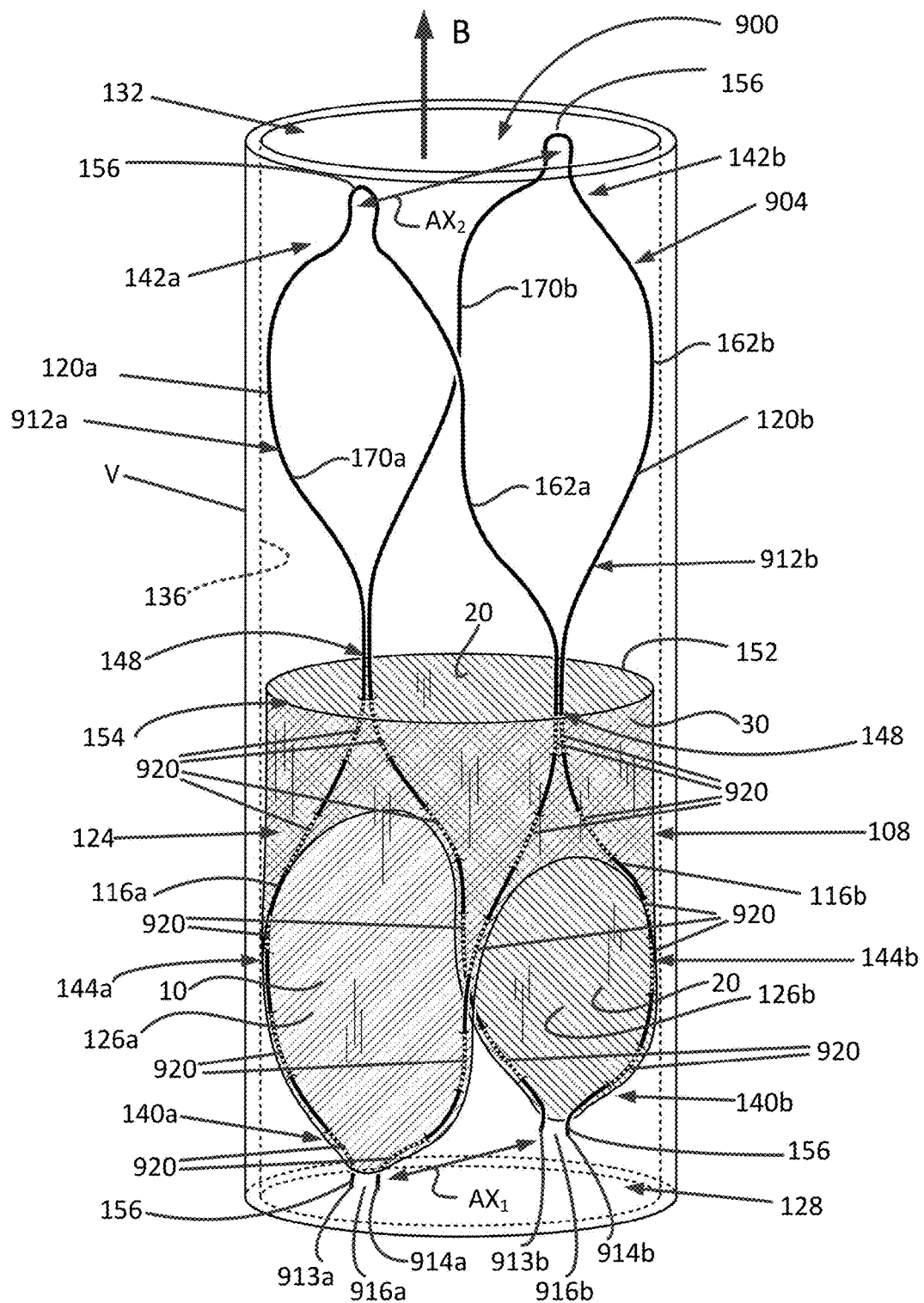
FIG. 9 is yet another embodiment of a prosthetic vascular valve, wherein the prosthetic vascular valve is shown situated within a section of a vein.

Referring now to FIG. 9, in a separate embodiment, a prosthetic vascular valve 900 includes is a frame 904 similar in a variety of aspects to prosthetic vascular valve 100. The frame 904 incorporates a first loop or first frame portion 912a and a second loop or second frame portion 912b; however, at least one of the first and second frame portions 912a, 912b do not form a closed or continuous loop. More particularly, in at least one embodiment, both the first and second frame portions 912a and 912b each include a single strand of material (e.g., a strand of nitinol wire or multiple portions joined to form a single strand), wherein, optionally, the first frame portion 912a includes a first end 913a and a second end 914a, wherein the frame 904 thus includes an opening 916a. In addition, optionally, the second frame portion 912b includes a first end 913b and a second end 914b, wherein a second opening 916b is associated with prosthetic vascular valve 900. The first loop 912a includes a first side or first longitudinal branch 162a and a second side or second longitudinal branch 170a. Similarly, the second loop 912b includes a first side or first longitudinal branch 162b and a second side or second longitudinal branch 170b.

As depicted in FIG. 9, and although it may be positioned elsewhere, in at least one embodiment, the opening 916a in the frame 912a is preferably located at an extension or eyelet 156, such as at the proximal end 128. In addition, if present, although it may be positioned elsewhere, the opening 916b is preferably also located at an extension or eyelet 156, such as at the proximal end 128. In at least one embodiment, openings 916a, 916b, if used, measure between 0.1 mm to 5.0 mm, although it may be dimensioned differently, including each 0.1 mm difference between 0.1 mm and 5.0 mm.

In at least one embodiment, portions of the frame 904 at the openings 916a and 916b may optionally include a blunted or curved terminus (not shown). More particularly, if used, one or more of first ends 913a, 914a, 913b and/or 914b may be blunted or curved, such as curved radially inward relative to the vein wall. Moreover, if a curved terminus is provided, such curved terminus may serve to provide a hook for applying a tensioning force to the associated vascular valve. Accordingly, a filament may be temporarily used to contact the curved terminus and apply a tensile force to the associated vascular valve for facilitating loading of the vascular valve in a catheter, needle or other delivery device.

A discontinuity or opening feature may be combined with the frame 804 depicted in FIG. 8, as well as with other frames shown and described herein, including those discussed below.

Still referring to FIG. 9, and as those skilled in the art will appreciate, the membrane 124 may be interconnected to the frame by sutures and/or other suitable means, to include staples or bonding, and/or the membrane 124 can be threaded or woven directly on to the frame 904 itself. By way of example, slits or holes may be formed in the membrane 124 along portions near the perimeter of the membrane 124 that correspond to the geometry of the frame 904 to which it is to be attached. Thereafter, the frame 904 is then woven through the membrane 124, thereby providing attachment of the membrane 124 to the frame 904. Woven portions 920 of the membrane 124 over the frame 904 are depicted in FIG. 9. Such woven portions 920 may be spaced apart longitudinally along the frame 904, such as along the first longitudinal portions 116a, 116b. As those skilled in the art will appreciate, the membrane may be held in place solely by the frame 904 through tension applied to the membrane 124 by the frame. In one or more other embodiments, in addition to weaving the frame 904 through the membrane to attach the membrane 124 to the frame 904, other additional means of attaching the membrane to the frame may also be employed, such as one or more of sutures, staples or adhesives. By way of example, optionally, one or more sutures may be used, such as at the loop convergence areas 148, to further secure the membrane to the first longitudinal portions 116a, 116b of the frame 904.

Referring now to FIGS. 10-13, in a separate embodiment, a prosthetic vascular valve 1000 is shown that includes a triple-loop frame 1004 and features a three leaflet membrane. More particularly, the triple-loop frame 1004 includes a first loop 1012a, a second loop 1012b and a third loop 1012c. Accordingly, as those skilled in the art will appreciate, a prosthetic vascular valve can include a single loop, such as prosthetic vascular valve 800 as depicted in FIG. 8, and multiple loops, such as prosthetic vascular valve 100 depicted in FIG. 1 and prosthetic vascular valve 1000 depicted in FIG. 10.

Figure 11:
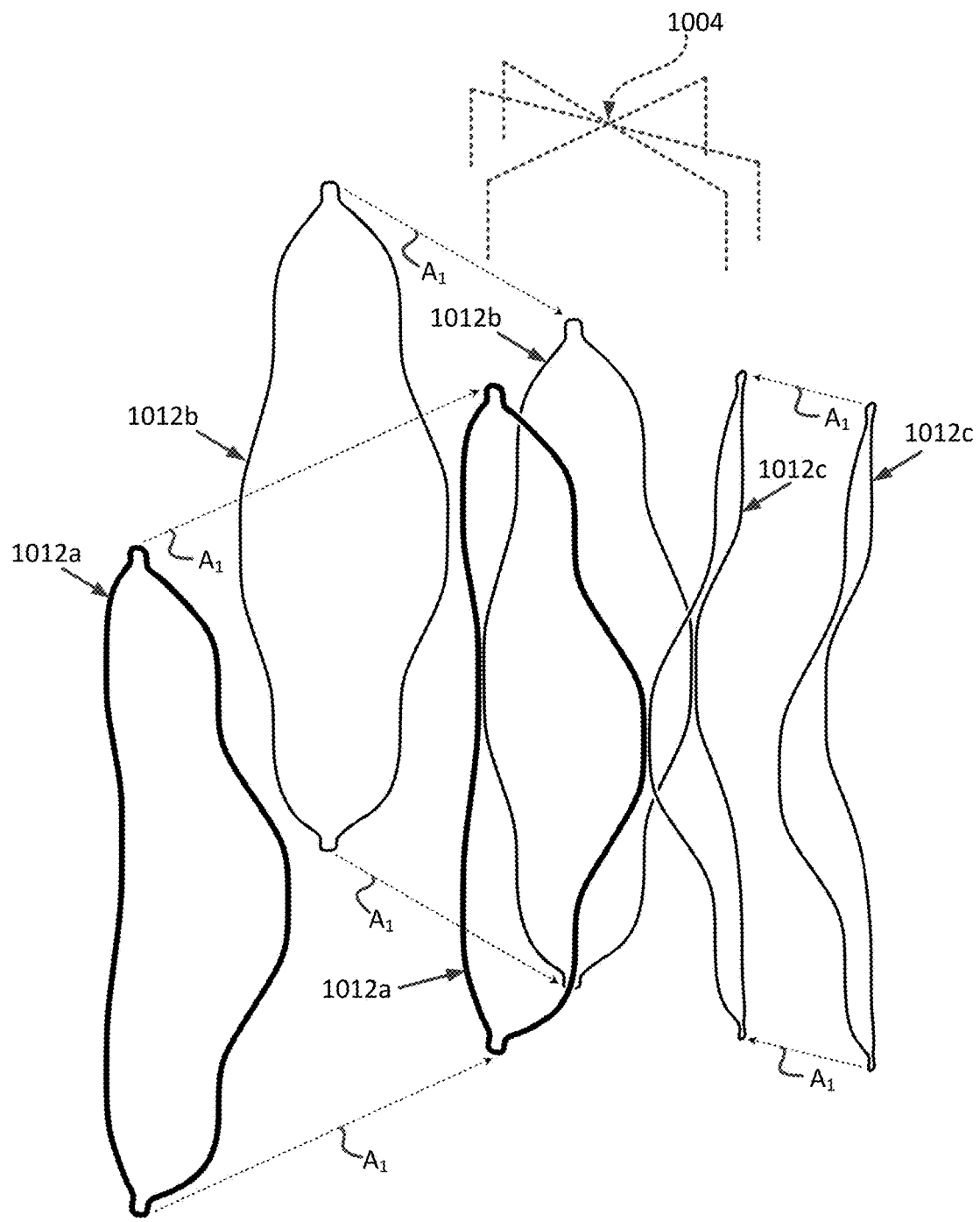
FIG. 11 is a perspective exploded view of the frame members forming the frame of the prosthetic vascular valve illustrated in FIG. 10.

Referring now to FIG. 11, the frame elements of frame 1004 are depicted in an exploded view and an assembled view. More particularly, first loop 1012a (in bold line weight) is shown on the lower-left side of FIG. 11, with second loop 1012b (in regular line weight) shown on the upper-left side of FIG. 11, and third loop 1012c (also in regular line weight) shown on the right-most side of FIG. 11. When physically brought together, such as is indicated by the dashed arrows $A_1$, the first, second and third loops 1012a, 1012b, and 1012c of the frame 1004 can be seen in the positions they possess to form the frame 1004 (without the membrane 124 attached to the frame 1004).

Figure 12:
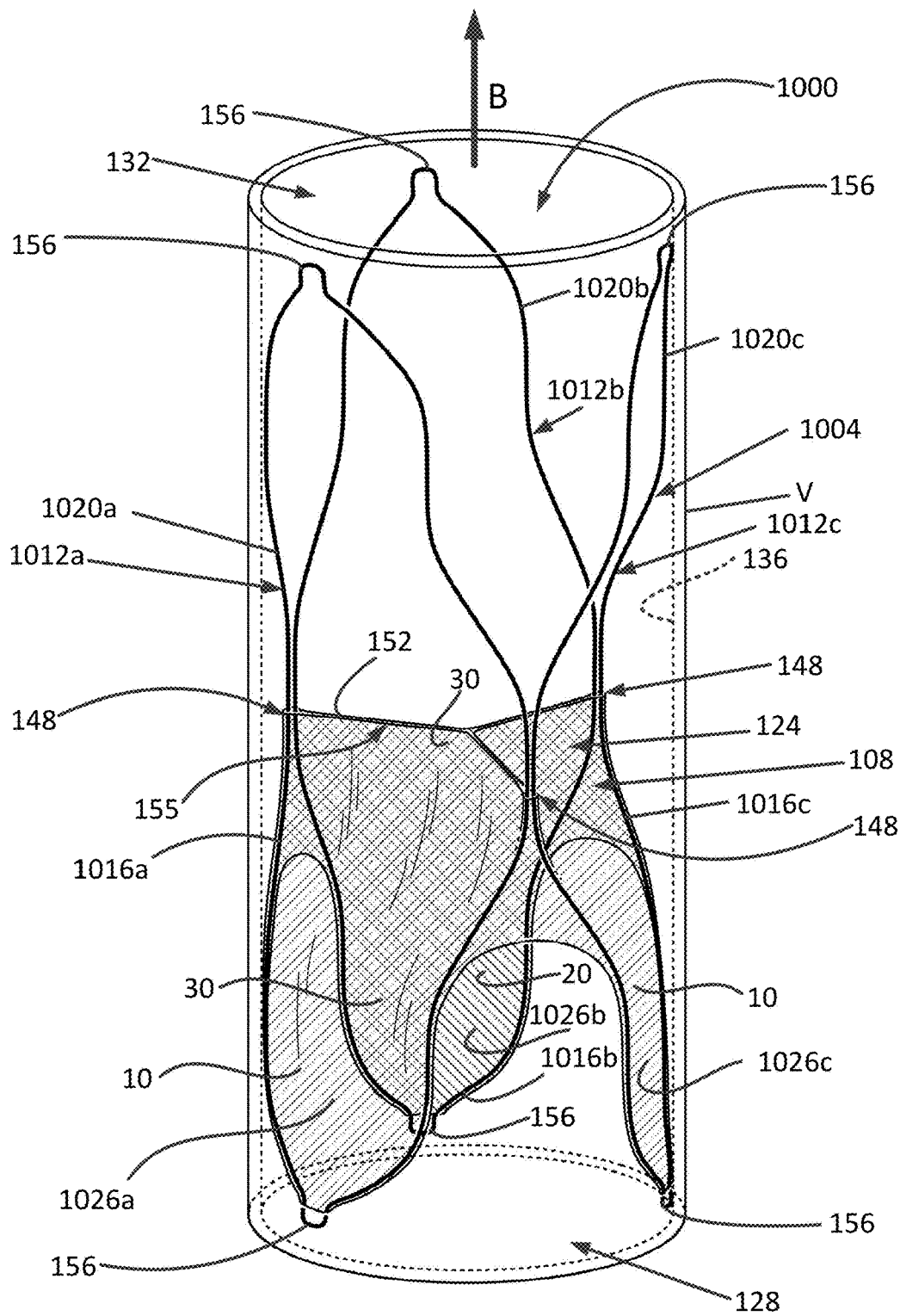
FIG. 12 is a side perspective view of the prosthetic vascular valve shown in FIG. 10 with the membrane closed.

Referring again to FIG. 10, as with frame 104, the first loop 1012a, second loop 1012b and the third loop 1012c each include first longitudinal portions 1016a, 1016b, 1016c and second longitudinal portions 1020a, 1020b, 1020c, respectively. For the device shown in FIG. 10, the first longitudinal portions 1016a, 1016b, 1016c are each operatively associated with the dynamic liquid barrier 108 that, preferably, may take the form of a membrane 124 that is formed into a cylindrically-shaped or substantially cylindrically-shaped structure that includes membrane lobes 1026a, 1026b, 1026c for attachment to the first longitudinal portions 1016a, 1016b, 1016c respectively, of the first loop 1012a, the second loop 1012b and the third loop 1012c of the frame 1004. Alternatively, the dynamic liquid barrier 108 may be attached in multiple pieces to the first longitudinal portions 1016a, 1016b, 1016c of the frame 1004. More particularly, a first piece of membrane (not shown) may be attached to first longitudinal portion 1016a, a second piece of membrane (not shown) may be attached to the first longitudinal portion 1016b, and a third piece of membrane (not shown) may be attached to the first longitudinal portion 1016c. As best seen in FIG. 12, when in the closed position 155, the membrane 124 and its membrane lobes 1026a, 1026b, 1026c mitigate regurgitation and paraprosthetic leakage of blood flow both through and radially adjacent to the prosthetic vascular valve 1000.

Figure 13:
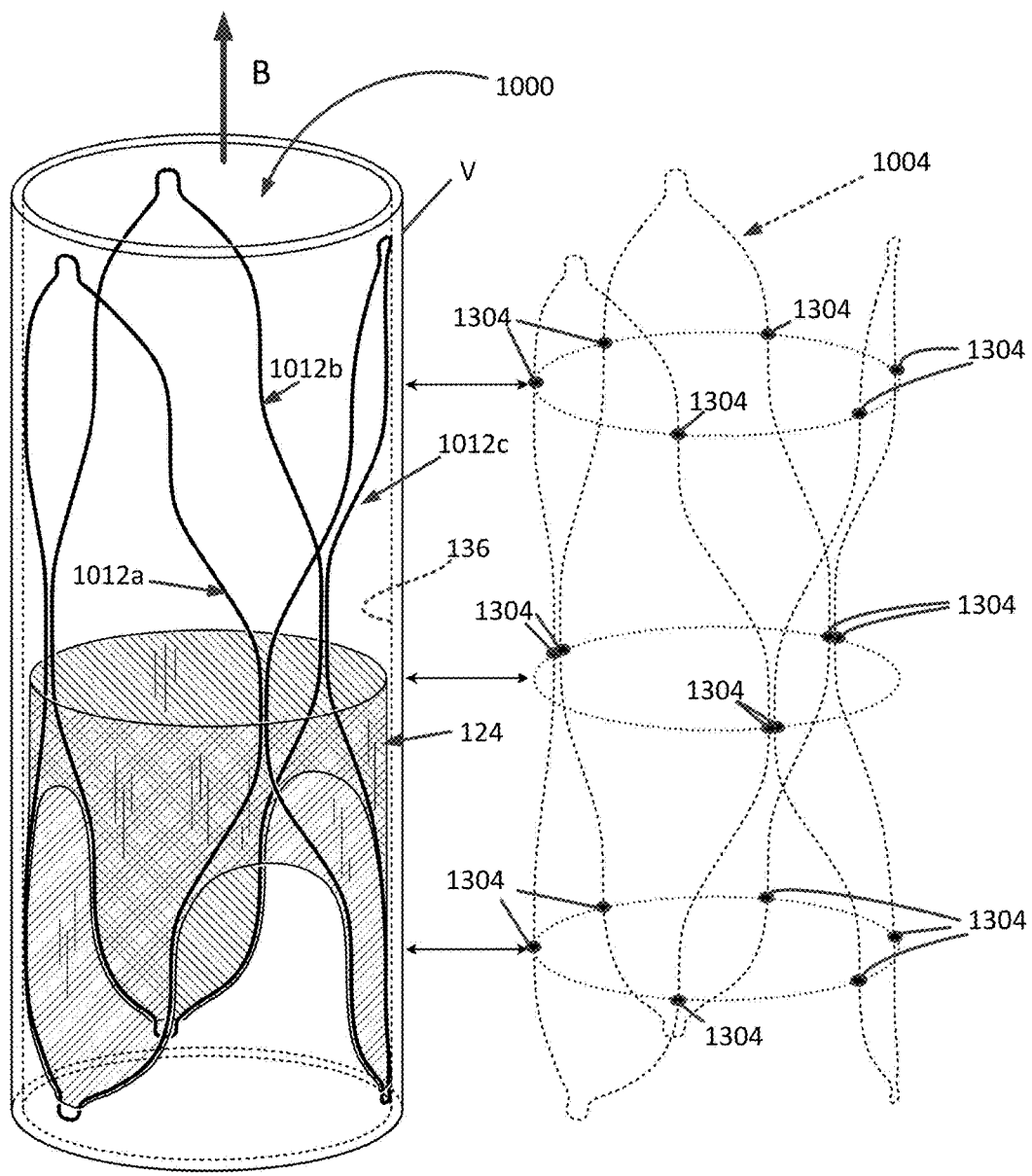
FIG. 13 is a side perspective view of the prosthetic vascular valve shown in FIG. 10, together with a rendering of a series of horizontal planes (relative to the orientation of the sheet) that pass through the prosthetic vascular valve.

With reference now to FIG. 13, prosthetic vascular valve 1000 is shown on the left side, with the right side of the drawing depicting the frame 1004 (dashed lines) with a series of planar rings (also dashed lines) situated along the longitudinal length of the frame 1004, wherein each planar ring is simply a graphical representation of a plane through the prosthetic vascular valve 1000, each coincidentally intersecting both the frame 1004 members and the cylindrical inner surface 136 of the containing vessel V at contact points 1304, demonstrating that the frame 1004 members are in contact with the inner surface 136 of vein V, and that the loops 1012a, 1012b and 1012c are shaped so that an outer surface of the loops 1012a, 1012b and 1012c lies on a common cylinder. Multiple additional planes may be drawn showing similar disposition of contact points. FIG. 13 is provided to emphasize that the frame contacts the inner surface 136 of the vein along most of the length of the prosthetic vascular valve 1000. It should be appreciated that the shape of the loops 1012a, 1012b and 1012c are designed as a curvilinear course along a cylinder such that by virtue of geometry, the frame 1004 maintains wall contact within a generally cylindrical vessel, such as a vein, along the full length of the prosthetic vascular valve 1000. It can be seen that the frame 1004 (or membrane material attached to the frame) contacts the inner surface 136 of the vein V along a majority of the longitudinal length of the frame 1004, such as along greater 50% of the longitudinal length of the frame, and more preferably greater than along 60% of the longitudinal length of the frame, and more preferably yet greater than along 70% of the longitudinal length of the frame, and still more preferably greater than along 75% of the longitudinal length of the frame, and still more preferably yet greater than along 80% of the longitudinal length of the frame, and even more preferably greater than along 85% of the longitudinal length of the frame, and still even more preferably greater than along 90% of the longitudinal length of the frame.

Figure 14:
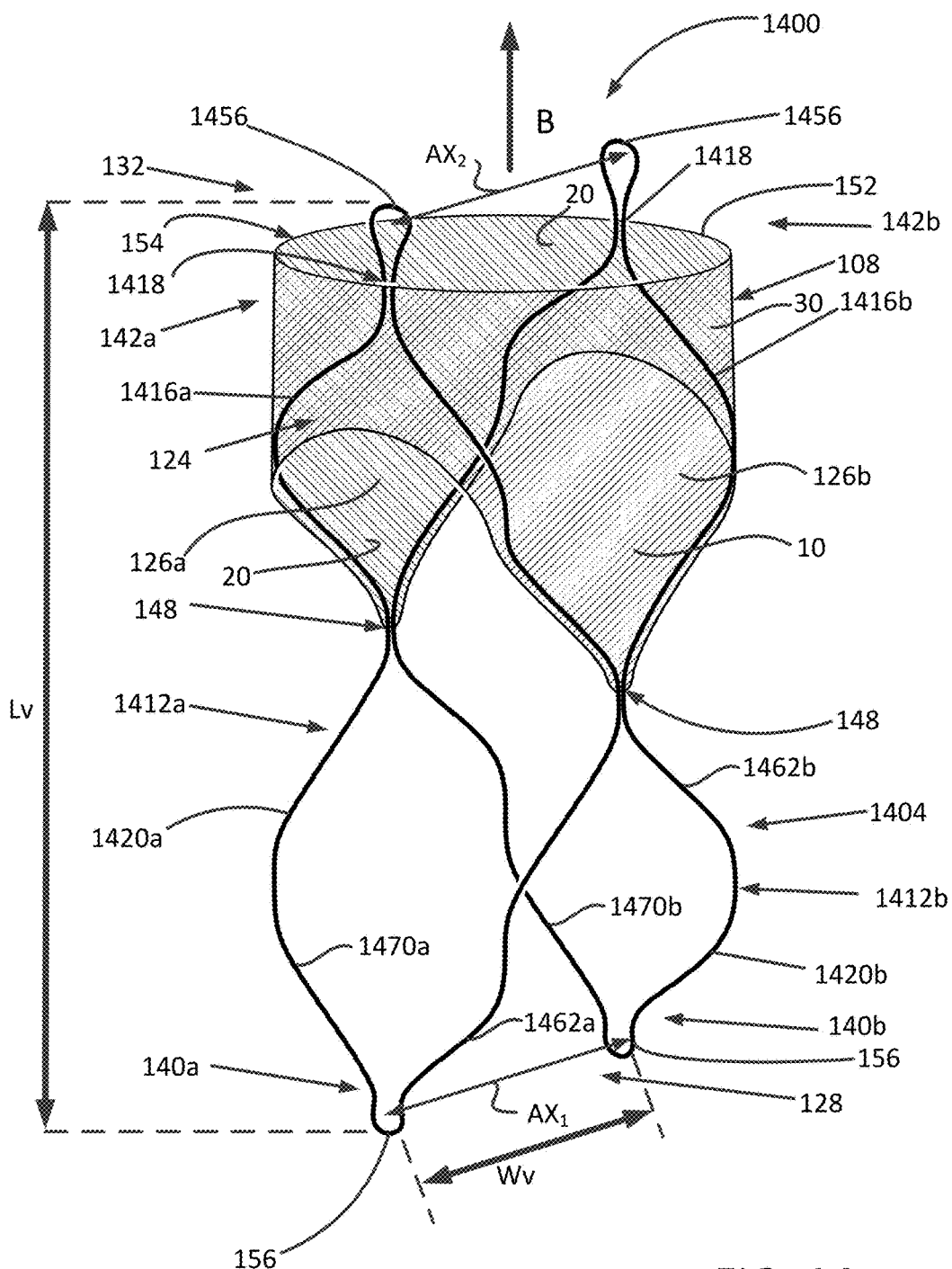
FIG. 14 is another embodiment of a prosthetic vascular valve.

Referring now to FIG. 14, another embodiment of a prosthetic vascular valve is shown. Similar to prosthetic vascular valve 100 with frame 104, prosthetic vascular valve 1400 with frame 1404 includes a plurality of loops, including a first loop 1412a and a second loop 1412b, wherein the first loop 1412a includes a first longitudinal portion 1416a and a second longitudinal portion 1420a, and wherein the second loop 1412b includes a first longitudinal portion 1416b and a second longitudinal portion 1420b. The first loop 1412a includes a first side or first longitudinal branch 1462a and a second side or second longitudinal branch 1470a. Similarly, the second loop 1412b includes a first side or first longitudinal branch 1462b and a second side or second longitudinal branch 1470b. Distal eyelets 1456 are located along the first loop 1412a and second loop 1412b at the distal end 132 of the prosthetic vascular valve 1400. In addition, intrastrand convergence areas 1418a, 1418b are located directly proximal to the distal eyelets 1456. The intrastrand convergence areas 1418a, 1418b are locations where two portions of the same loop are situated adjacent one another. For the prosthetic vascular valve 1400 shown in FIG. 14, the membrane 124 is attached to the first longitudinal portions 1416a, 1416b.

Referring still to FIG. 14, the membrane 124 opens and closes near the distal end 132 of the prosthetic vascular valve 1400 because the frame 1404 and the membrane 124 are configured to position the free end 152 of the membrane 124 near the distal end 132 of the prosthetic vascular valve 1400. That is, prosthetic vascular valve 1400 includes a frame 1404 with a membrane 124, wherein the membrane 124 is located along a downstream portion of the frame 1404. The intrastrand convergence areas 1418a and 1418b are generally aligned diametrically opposite one another, such that the membrane free edge is also in general alignment with the intrastrand convergence areas 1418a, 1418b when the membrane is closed. As those skilled in the art will appreciate, various embodiments of prosthetic vascular valves described herein are directed to devices that possess a membrane to serve as a check valve, wherein the free ends of the membrane that open and close can be situated at different locations along the length of a frame. As can be seen in FIG. 14, prosthetic vascular valve 1400 includes a membrane 124 with free ends 152 located near the distal end 132 of the prosthetic vascular valve 1400. In contrast, as described above, prosthetic vascular valve 100 includes a membrane 124 with free ends 152 located near the loop convergence areas 148 of the frame 104, which are located in the vicinity of a longitudinally intermediate portion of the prosthetic vascular valve 100. In addition, as also described above, prosthetic vascular valve 800 includes a membrane 124 with free ends 152 located near the intrastrand or intraloop convergence areas 818 of the frame 804, which are also located in the vicinity of the longitudinally intermediate portion of the prosthetic vascular valve 800. Accordingly, various embodiments of the prosthetic vascular valves described herein possess a membrane valve having free ends that are situated at different locations along the length of the frame.

As with prosthetic vascular valve 100, 800, and 1000, frame 1404 of prosthetic vascular valve 1400 is elongated to provide stability within the patient's anatomy because most of the length of both the first and second loops 1412a, 1412b is biased to contact an inner surface of the vasculature of the patient, which will thereby mitigate or prevent longitudinal movement of the prosthetic vascular valve 1400 in the direction of blood flow B. It should be appreciated that the shape of the loops 1412a and 1412b are designed as a curvilinear course along a cylinder such that by virtue of geometry, the frame 1404 maintains wall contact within a generally cylindrical vessel, such as a vein, along the full length of the prosthetic vascular valve 1400. Moreover, as with all embodiments of the various prosthetic vascular valves described herein, the overall length of the prosthetic vascular valve 1400 will advantageously mitigate or prevent tumbling of the prosthetic vascular valve 1400 within the vasculature of the patient, because the valve length Lv of the prosthetic vascular valve relative to its valve width Wv (that is, the prosthetic vascular valve diameter) adequately maintains a substantially parallel alignment of the longitudinal axis of the prosthetic vascular valve 1400 with the longitudinal axis of the patient's vasculature. For the various prosthetic vascular valves described herein, the length Lv of the prosthetic vascular valve (that is, the total longitudinal length of the prosthetic vascular valve including both the portions of the frame that include and exclude membrane) is between about 2 to 8 times greater than the valve width Wv (that is, the prosthetic vascular valve diameter).

In a separate embodiment not shown, the prosthetic vascular valve 1400 illustrated in FIG. 14 may further include a functioning membrane valve along its second longitudinal portions 1420a, 1420b. More particularly, frame 1404 of prosthetic vascular valve 1400 may include a membrane 124 along the first longitudinal portions 1416a, 1416b as shown in FIG. 14, as well as a membrane 124 at the second longitudinal portions 1420a, 1420b, wherein both the membrane 124 at the first longitudinal portions 1416a, 1416b and the membrane 124 at the second longitudinal portions 1420a, 1420b can operate as a check valves to mitigate or prevent regurgitation of blood through the vasculature within which it is implanted.

Figure 15:
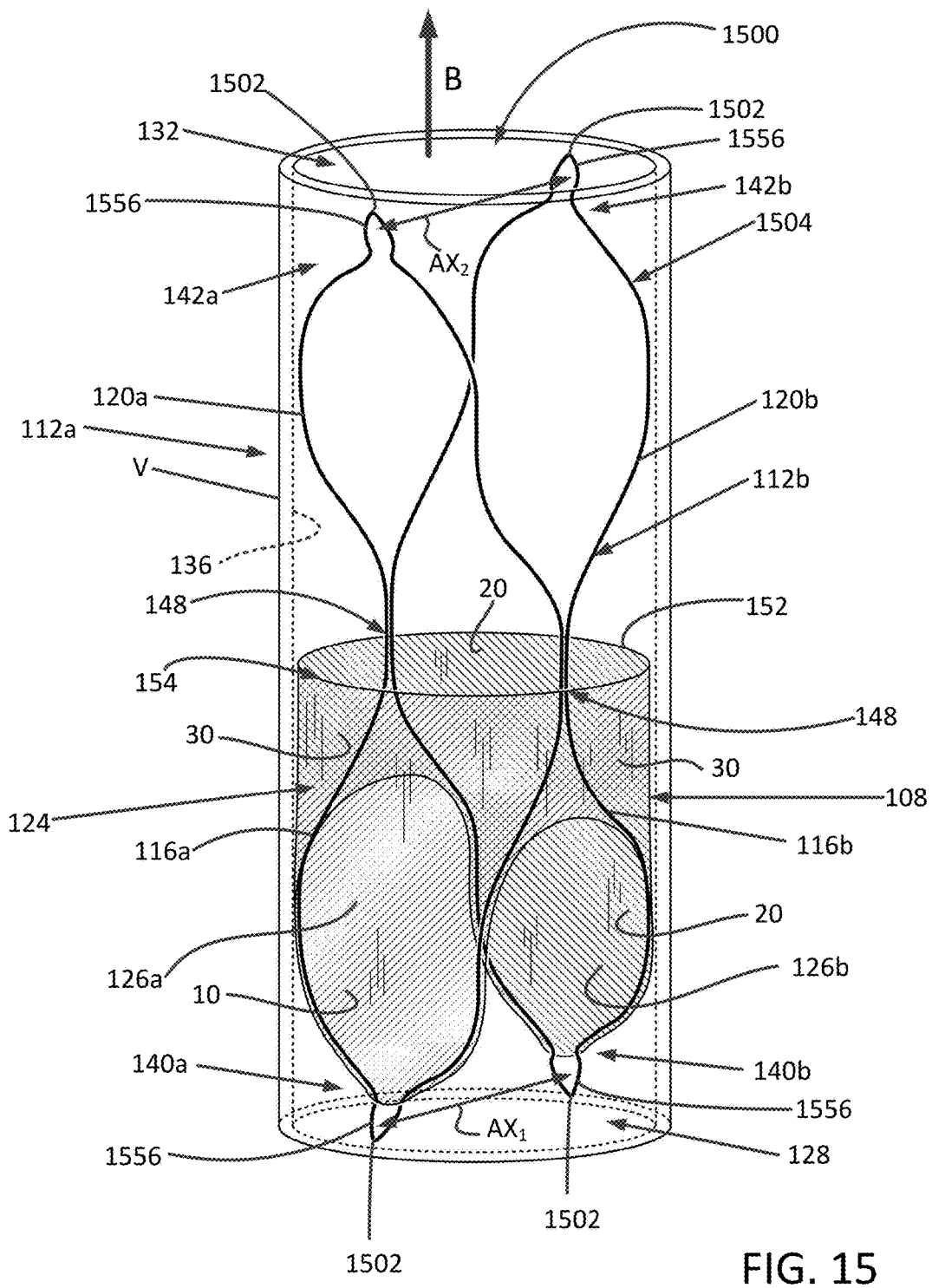
FIG. 15 is another embodiment of a prosthetic vascular valve situated within a section of a vein.
Figure 16:
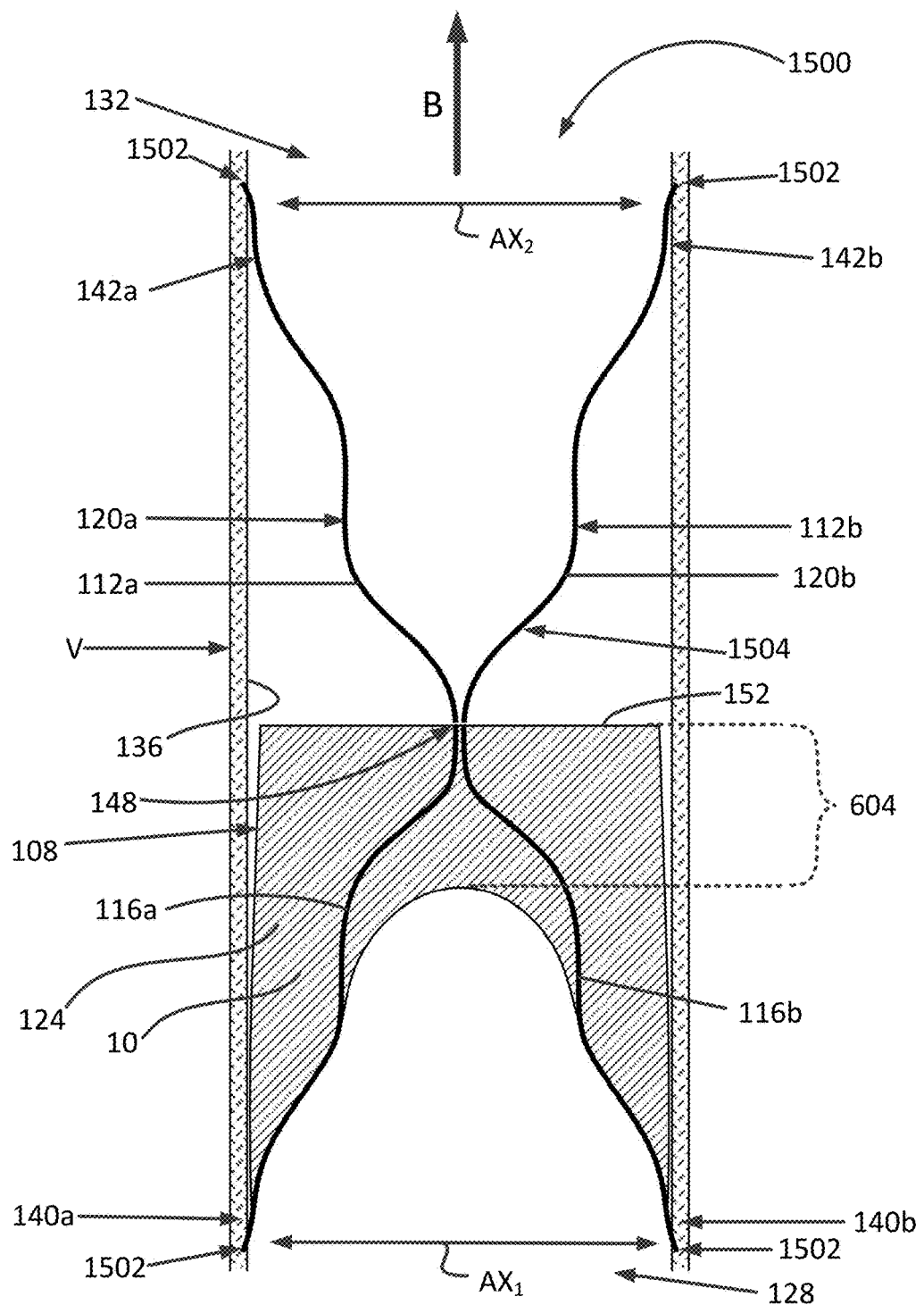
FIG. 16 is a side elevation view of the device shown in FIG. 15.

As described above, at least some embodiments include an eyelet 156 at either the proximal and/or distal end of at least one loop associated with a vascular prosthetic valve. Referring now to FIGS. 15 and 16, in at least some embodiments the frame may include a plurality of eyelets 156, wherein one or more of the eyelets includes a pointed tip 1502 for at least frictionally engaging the inner surface 136 of the vein V, and/or for serving as means for penetrating the inner surface 136 of the vein V and/or the wall of the vein V to anchor the prosthetic vascular valve within the vein V. Accordingly, the frame itself may include a portion that is shaped to form a barb, such as by possessing an eyelet with one or more pointed tips 1502. As shown in FIG. 15, the frame 1504 is similar to frame 104 as shown in FIG. 1, but includes eyelets 1556 with pointed tips 1502 at both the proximal end 128 and the distal end 132. Alternatively, the frame may include eyelets with at least one pointed tip, or alternatively two pointed tips, at only the distal end 132, thereby providing a means for anchoring the prosthetic vascular valve to the vein V. The outward curving of the tips is advantageous for securement of the implant position as may be an issue in some cases as in larger, more dilated veins, because accommodating such veins can be a special application of a prosthetic vascular valve. Also, vein valves often have small cusps that make the vein at that location effectively larger than the body of the vein below it, so placing a replacement valve at that location (as may be advantageous to the emulation of the normal flow patterns) may require better securement.

In yet another alternative, the frame may include a barb that is attached to the frame. That is, in at least one embodiment, the frame does not include an eyelet with a pointed tip, but does otherwise include at least one barb for assisting with anchoring the prosthetic vascular valve to a vein V upon deployment of the prosthetic vascular valve. In yet another alternative embodiment, the prosthetic vascular valve may include an eyelet 156 that is not shaped with a pointed tip, but wherein the frame does include a barb attached to the frame, such as a barb that is attached to an eyelet.

Figure 17:
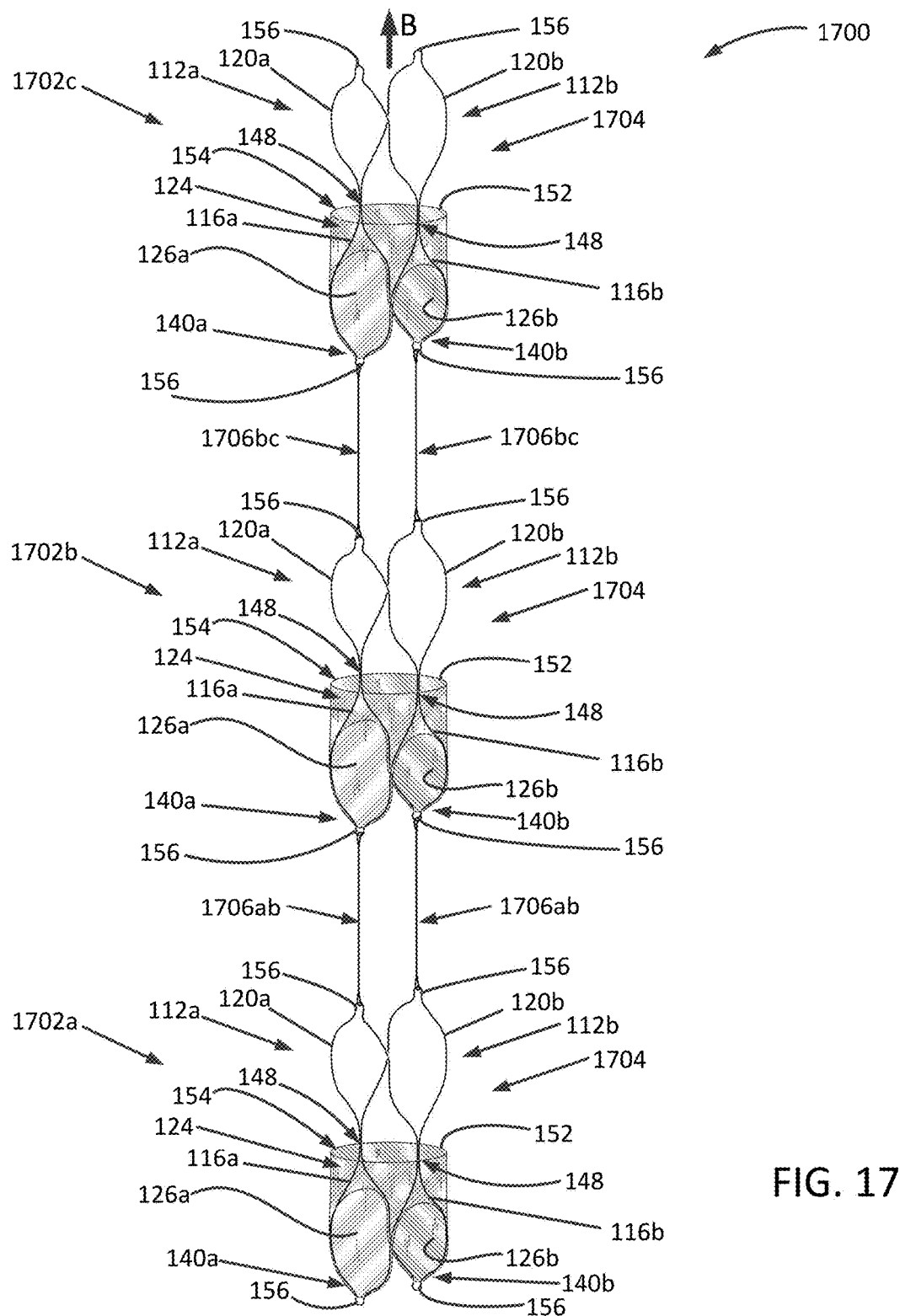
FIG. 17 is another embodiment of a prosthetic vascular valve that includes a plurality of membrane valves linked together.

Referring now to FIG. 17, and in accordance with yet another embodiment, a multiple-valve prosthetic vascular valve device 1700 is shown that includes a plurality of frame segments 1702 that each include a frame 1704. A membrane 124 may be associated with each frame 1704, wherein the membrane is configured to open to allow the passage of blood, and to close to mitigate or prevent the regurgitation of blood. As can be seen in FIG. 17, three frame segments 1702*a*, 1702*b* and 1702*c* are shown, with each frame segment 1702*a*, 1702*b* and 1702*c* including a membrane valve.

Referring still to FIG. 17, the first frame segment 1702*a* is linked to the second frame segment 1702*b* by first frame linkage 1706*ab*. In addition, a second frame linkage 1706*bc* links the second frame segment 1702*b* to the third frame segment 1702*c*. With regard to the first and second frame linkages 1706*ab* and 1706*bc*, although FIG. 17 illustrates the frame linkages 1706*ab* and 1706*bc* as single lengths of wire connected to loops of each frame segment, the frame linkages 1706*ab* and 1706*bc* could be a different shape. By way of example, one or more frame linkages can comprise a structure that engages the interior wall of the vasculature of the patient, such as a frame described herein that is biased radially outward, but wherein such frame does not include membrane valve. Alternatively, a multiple-valve prosthetic vascular valve device could include two or more back-to-back prosthetic vascular valves. For example, a multiple-valve prosthetic vascular valve device could include a first prosthetic vascular valve 100 connected to a second prosthetic vascular valve 100, wherein such connection may include connecting a distal end 132 of the first prosthetic vascular valve 100 to a proximal end 128 of the second prosthetic vascular valve 100.

A further alternative for a multiple-valve prosthetic vascular valve device includes combining at least two structural different prosthetic vascular valves. By way of example, a first prosthetic vascular valve, such as prosthetic vascular valve 100, can be linked to a second prosthetic vascular valve, such as prosthetic vascular valve 1400.

In yet a further alternative embodiment for a multiple-valve prosthetic vascular valve device, the first and second loops 112*a*, 112*b* may be elongated longitudinally, and may be fitted with a plurality of membrane valves. By way of example, a multiple-valve prosthetic vascular valve device can include a series of two or more prosthetic vascular valves 100 that are daisy-chained together or that are formed using a continuous loop on a first side and a continuous loop on a second side, wherein multiple membrane valves are attached to the longitudinally extensive loops.

As those skilled in the art will appreciate, a variety of different geometries could be used to form a multiple-valve prosthetic vascular device. By way of example, although a multiple-valve prosthetic vascular device 1700 is shown with three frame segments 1702*a-c*, a multiple-valve prosthetic vascular device with only two frame segments could be provided. Alternatively, multiple-valve prosthetic vascular device with 4, 5, 6, 7, 8, 9 or 10 or more frame segments could be provided. Regardless of the form of the linkages or the number of frame segments, as those skilled in the art will appreciate, the linkage material should be sufficiently stiff to facilitate deployment of the multiple-valve prosthetic vascular valve device.

Although not shown, in at least one embodiment an opening feature, such as described above and shown in FIG. 9 may be combined with other embodiments described herein, including the frames shown in FIGS. 8, 10, 14 and 15. In addition, for such embodiments the membrane 124 may be woven over the frame 804, 1004, 1404 and 1504 to thereby attach the membrane 124 to the frames.

For one or more embodiments described herein, substantially no membrane for performing the function of limiting fluid flow is connected to the second longitudinal portions 120*a*, 120*b* of the first and second loops 112*a*, 112*b*. Although not preferred, in some embodiments, at least some membrane 124 may be attached to the second longitudinal portions 120*a*, 120*b* of the frame 104, such as for assisting with connecting the membrane to the frame.

The frames 104, 804, 904, 1004, 1404 and 1504 are preferably made of a shape memory alloy, such as nitinol. Advantageously, nitinol offers that a specific size of a frame can be produced and implanted under temperatures that allow the material to be easily placed, while then providing the desired shape upon warming to body temperature. Nitinol wire used to form the frames for prosthetic vascular valves may have a diameter of equal to or greater than about 0.013 inches and equal to or less than about 0.015 inches; for a large vein, the diameter may be equal to or greater than about 1 to 2 mm. As presented further in this disclosure, frames can also be made of tubing that is cut to form at least one loop of the frames associated with the various vascular valves described herein. Alternatively, tubing may be cut to form a single-piece frame that includes a plurality of loops. By way of example, frames 2204 depicted in FIGS. 22 and 23, frame 2404 depicted in FIG. 24, frame 2504 depicted in FIG. 25, frame 2604 depicted in FIGS. 26 and 27, and frame 2804 depicted in FIGS. 28 and 29 may be single-piece frames that are cut from an alloy tubing, such as nitinol. Tubing of nitinol used to manufacture frames described herein may have a thickness of equal to or greater than 0.3 mm and equal to or less than 0.6 mm. Frames described herein may also be made of stainless steel or cobalt chromium alloys.

Alternatively, the frames 104, 804, 904, 1004, 1404 and 1504, as well as frames 2204, 2404, 2504, 2604 and 2804 described below, may be made of a bio-absorbable material that is slowly absorbed by the patient, thereby leaving the membrane in place and attached to the interior of the vein wall to function in the absence of the previously present bio-absorbable frame material.

For all embodiments of a prosthetic vascular valve described herein, the membrane may be a synthetic material (e.g., polyurethane) or a treated natural material that is impervious or substantially impervious to liquid flow, and is suitable to act as a check valve under the loading conditions and pressures anticipated for the valve operating conditions and anatomical implant site, as well as possessing characteristics suitable to withstand manufacturing/handling conditions and demands associated with crimping, loading and deployment. More preferably, for the embodiments described herein, the membrane may be a treated tissue, such as fixed pericardial tissue from an animal. More preferably yet, for the embodiments described herein, the membrane is a portion of tissue that is treated and formed into a cylindrical shape for attachment to the frame. Still more preferably yet, for the embodiments described herein, the membrane may be a harvested portion of vascular tissue from a source, such as a portion of a vein that already possesses a cylindrical shape, wherein the vascular tissue is treated and attached to the frame to form the prosthetic vascular valve.

Referring now to FIG. 18, an embodiment of a device for loading a prosthetic vascular valve 100 (as well as other prosthetic vascular valves described herein) into a delivery device is illustrated. More particularly, prosthetic vascular valve loading device 1800 includes a loading funnel 1804, shown in longitudinal cross section, with sloped sidewalls 1808 that lead from an opening 1812 to a transition neck 1816. The transition neck 1816 further leads to a narrowed opening 1820 that includes a shoulder 1824 and radially interior ring 1826 for placing against a delivery device 1828 to facilitate loading the prosthetic vascular valve, shown in side elevation view, into the delivery device 1828. The prosthetic valve 100 may also be loaded with the opposite end inserted first into the loading funnel 1804, depending on the most advantageous procedural approach to accessing the vein or other blood vessel.

Still referring to FIG. 18, to assist in loading the prosthetic vascular valve into the delivery device 1828, one or more tensioning lines 1832 may be used to apply a tensile force to the frame 104 of the prosthetic vascular valve 100. More particularly, tensioning lines 1832 may form a loop 1836 through eyelets 156 (as shown in the enlarged detail bubble of FIG. 18), and used to pull the prosthetic vascular valve 100 within the loading funnel 1804 such that the frame 104 contacts the sloped sidewalls 1808 of the loading funnel 1804 to cause the frame 104 to narrow per arrows 1840.

Referring now to FIGS. 19 and 20, an embodiment of a delivery system 1900 is shown. The delivery system 1900 includes a delivery device 1828, such as a needle or delivery catheter, that is sized for placement of a prosthetic vascular valve 100, 800, 900, 1000, 1400, 1500, 1700, 2600 and 2800 within a vessel, such as a vein V. As shown in FIG. 19, the prosthetic valve, shown in side elevation view, is compressed within a cylindrical section of a delivery device 1828, shown in cross sectional view. The distal end 1904 of the delivery device 1828 may be relatively flat. Alternatively, as shown in FIG. 20, the distal end 2004 of the delivery device 1828 may be sloped or configured of design and material to constitute a hypodermic needle and used to puncture the skin of the patient and thereafter inserted into the vein V for placement of a prosthetic vascular valve within the confines of the vein V. As shown in FIGS. 19 and 20, while residing within the delivery device 1828, the frame and membrane connected to the frame are in a crimped configuration. Upon placement within the vein V, such as by advancing pusher member 2008 to force the prosthetic vascular valve in a distal direction and out the distal end 2004 of the delivery device 1828, the prosthetic vascular valve expands to contact the vessel wall, thereby anchoring the prosthetic vascular valve within the vein V.

Alternatively, insertion can be achieved through an introducer sheath initially placed by an operator through the skin of the patent and into a vein. More particularly, access to central veins through standard catheterization techniques can be performed. The insertion with a sheath introducer would allow for the advancement of standard catheters to the target implant site through which the compressed prosthetic vascular valve could be advanced by pusher catheter to achieve deployment by the advancement from the end of the indwelling catheter.

Figure 21:
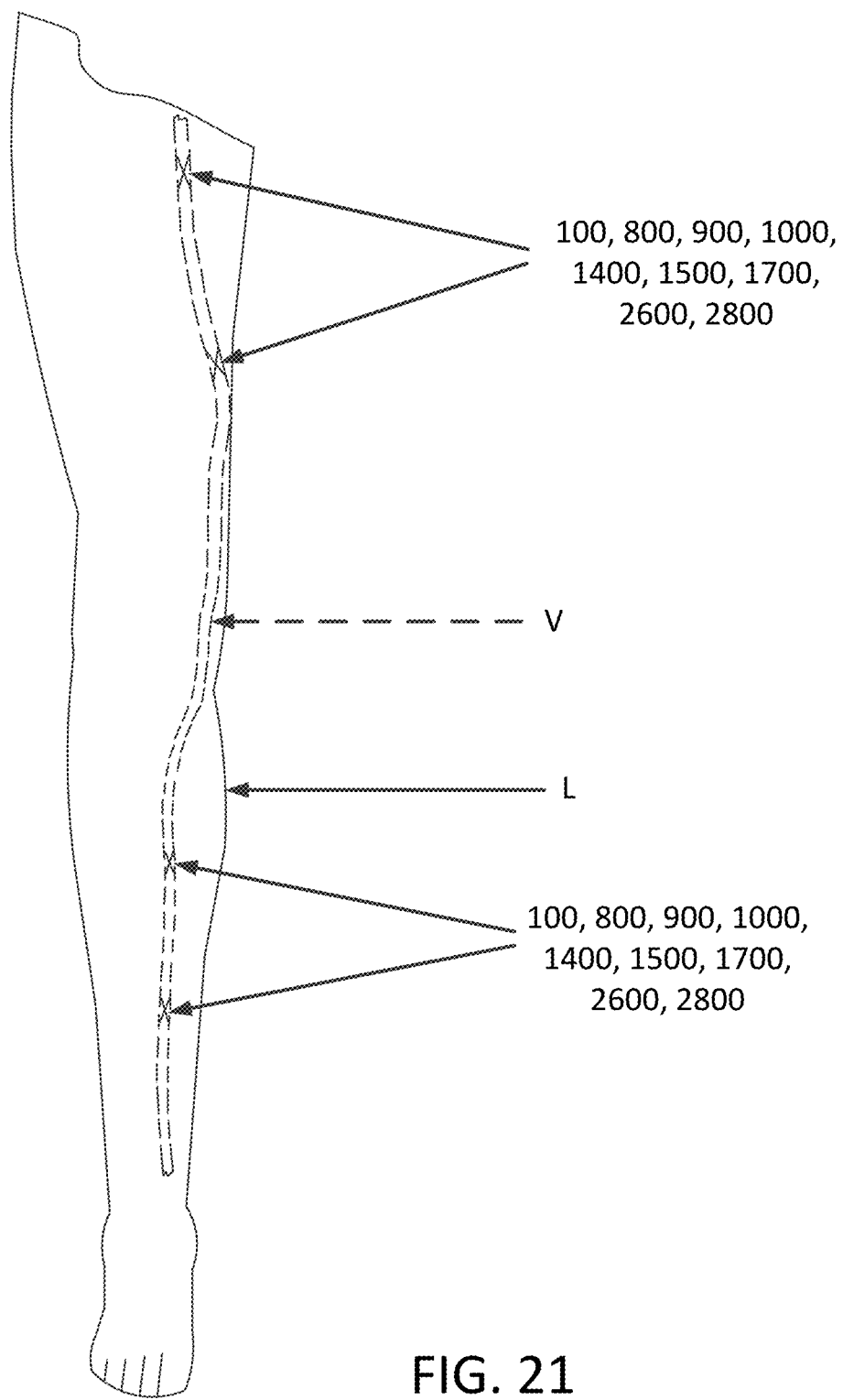
FIG. 21 is an illustration of a patient's leg, wherein the patient's leg has received multiple prosthetic vascular valves.

Referring now to FIG. 21, an illustration of a patient's leg is shown, wherein the multiple valves have been implanted within a vein V of the patient's leg L. As those skilled in the art will appreciate, different size prosthetic vascular valves may be necessary to accommodate the particular needs of a given patient depending upon the size of the vessel to be treated.

Frames for the various prosthetic vascular valves described herein may be constituted of alloy, including shape memory alloy that is cut from an alloy tube in a single piece or in multiple pieces. In at least some embodiments, the frames of the prosthetic vascular valves include multiple loops, wherein each loop of the frame is formed of a single strand of wire, such as nitinol wire. By way of further example, each loop of the multiple loops can be formed by cutting each loop from a tube of material. By way of further example yet, a first loop can be cut from a first tube of material and a second loop can also be cut from the first tube of material. Alternatively, a first loop can be cut from a first tube of material and a second loop can be cut from a second tube of material.

In at least some embodiments, the frame may be made of nitinol. In at least one embodiment, the nitinol forming frame includes at least one weld. In at least one embodiment, the nitinol forming frame does not include a weld. As noted above, frame members for one or more embodiments may be made by cutting a tube of material, thereby providing a continuous loop of material. Accordingly, frame members for one or more embodiments may be made by cutting a tube of nitinol to form the frame members.

Figure 22:
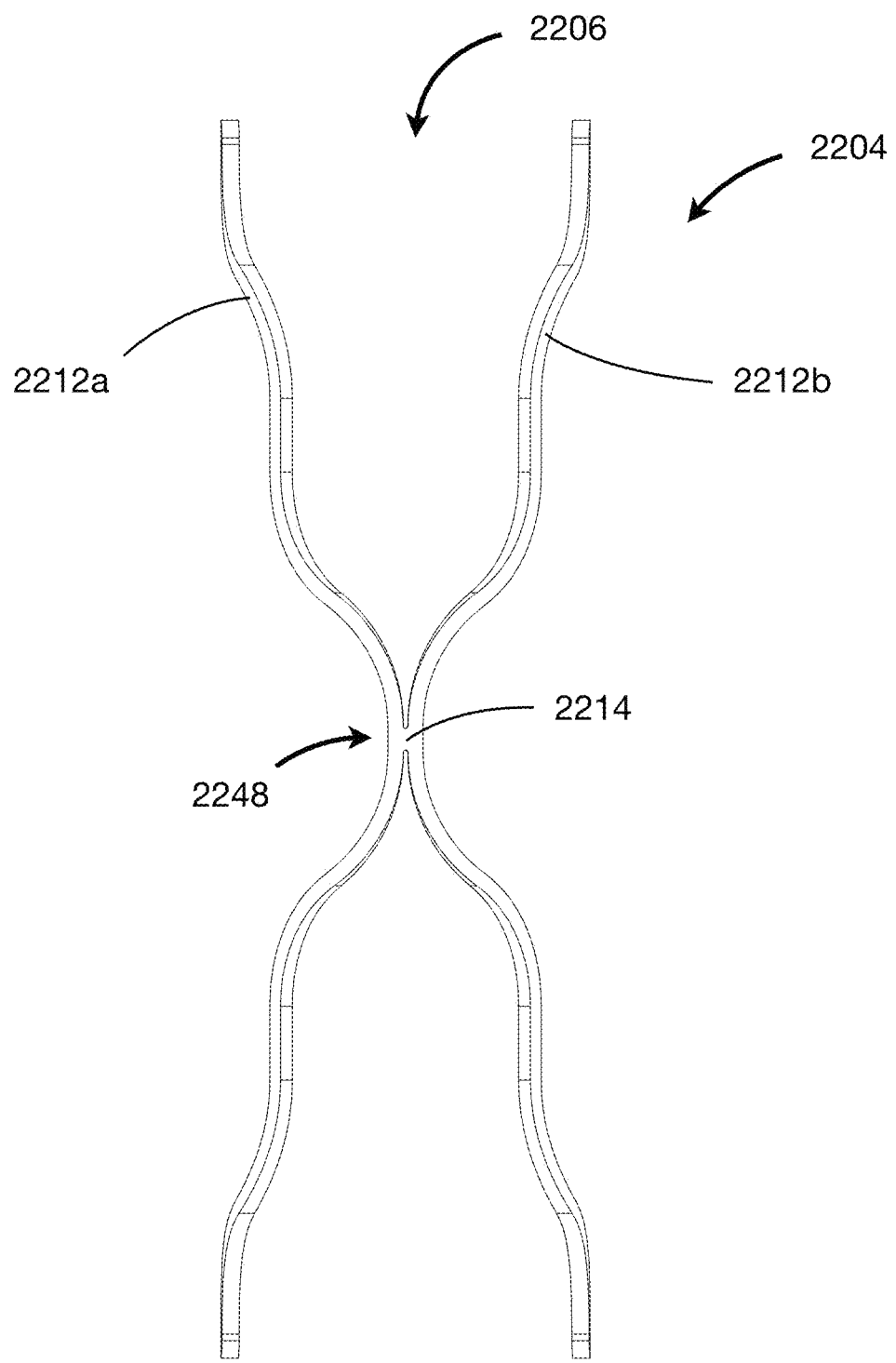
FIG. 22 is a longitudinal side elevation view of an embodiment of a single-piece two-loop frame cut from a tube of material, the single-piece frame generally substitutable for the frame shown in FIG. 1.
Figure 23:
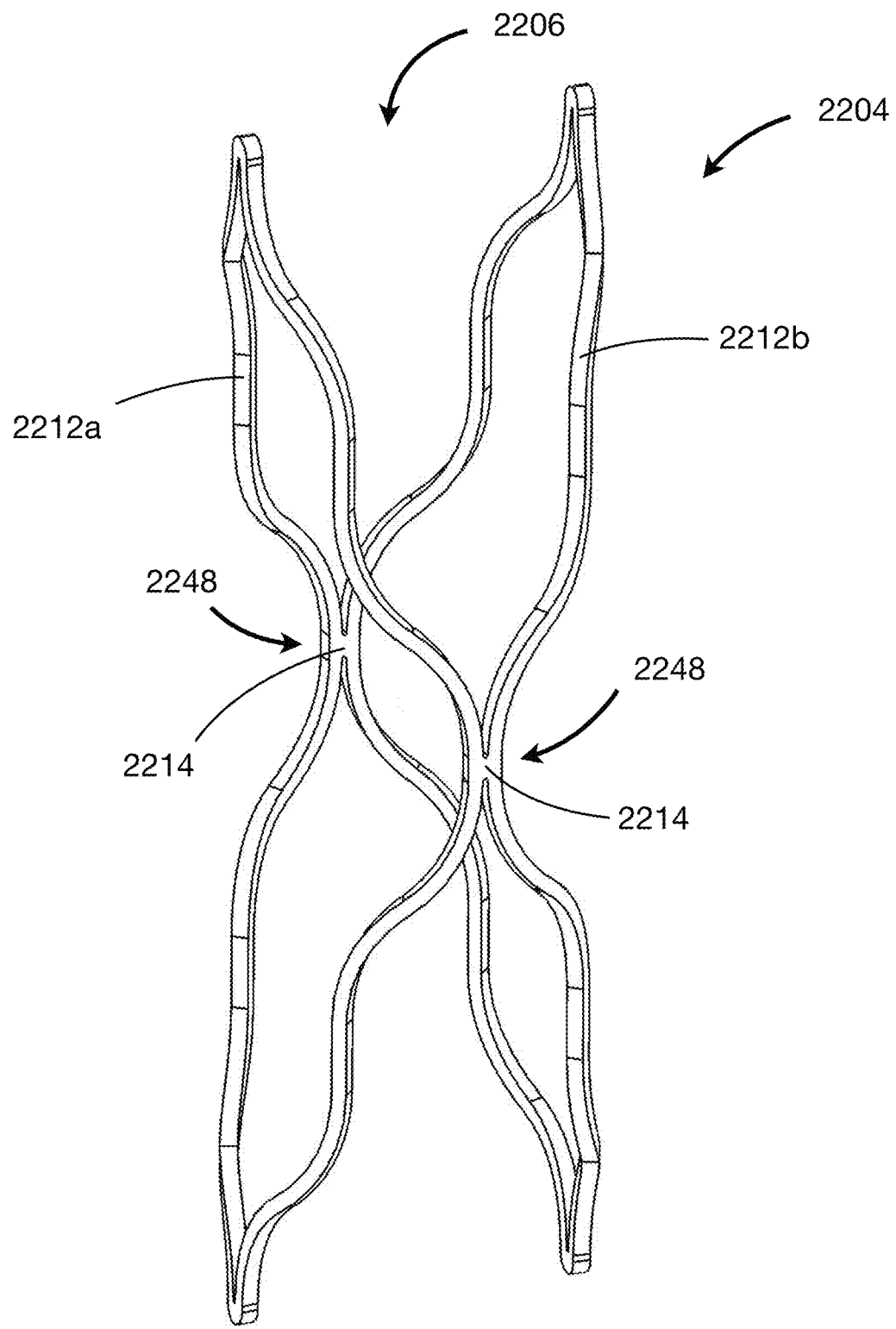
FIG. 23 is a side perspective view of the frame shown in FIG. 22.

Referring now to FIGS. 22 and 23, an embodiment of a frame 2204 is shown that has been cut from a cylindrical alloy tube, thus providing a shape with an outer surface to reside against a cylindrical-shaped vessel. That is, because the frame is cut from a cylinder, the resulting loops generated from cutting the cylinder are going to have an outer surface that contacts a cylinder. More particularly, as noted above, one method of making a frame for one or more of the prosthetic vascular valves described and/or shown in this disclosure is to obtain a tube of material, such as a metal alloy, for example nitinol, and thereafter cut the frame from the tube, such as by using a laser. By way of example, the tube may have a wall thickness of between about 0.3 to 0.6 mm. Upon cutting the tube of material, the resulting structure is the frame that can be used to receive a membrane, and thereby form a prosthetic vascular valve. As shown in FIGS. 22 and 23, the frame 2204 includes a double-loop structure 2206 including a first loop 2212a and a second loop 2212b. It should be appreciated that the shape of the loops 2212a and 2212b are designed as a curvilinear course along a cylinder such that by virtue of geometry, the frame 2204 maintains wall contact within a generally cylindrical vessel, such as a vein, along the full length of the prosthetic vascular valve.

In at least one embodiment, the entire frame 2204 is a single piece of material. Accordingly, in at least one embodiment, the first loop 2212a is interconnected to the second loop 2212b by at least one loop joining area 2214. The embodiment shown in FIGS. 22 and 23 includes two loop joining areas 2214, wherein the loop joining areas 2214 are located diametrically opposite one another. In at least one embodiment, the loop joining areas 2214 may comprise a section of the frame 2204 where the first loop 2212a merges with the second loop 2212b. Alternatively, at least one loop joining area 2214 may comprise a bridging strut, wherein at least some material spans between the first loop 2212a and the second loop 2212b. Once the frame 2204 is prepared from cutting the tube of material, a membrane 124 can be attached to the frame 2204 (as shown in FIG. 1), such as by suturing the membrane 124 to the frame, wherein the free edge 152 of the membrane (shown in FIG. 1) is generally aligned with the longitudinally oriented strand convergence areas 2248 and the loop joining areas 2214 as depicted in FIGS. 22 and 23. Accordingly, a frame with two longitudinally oriented loops would possess a membrane with two leaflets. Referring generally to the shape of loops 2212, throughout all the portions of the loops, curved or otherwise, the radially outer surfaces of the loops are configured to lie on a common cylinder so as to advantageously contact the inner surface of the vessel at all surface points of the loops when the valve device is deployed in a blood vessel. Further, loops 2212 are similarly configured for contacting the blood vessel when three, four or another number of loops comprise the frame.

Figure 10:
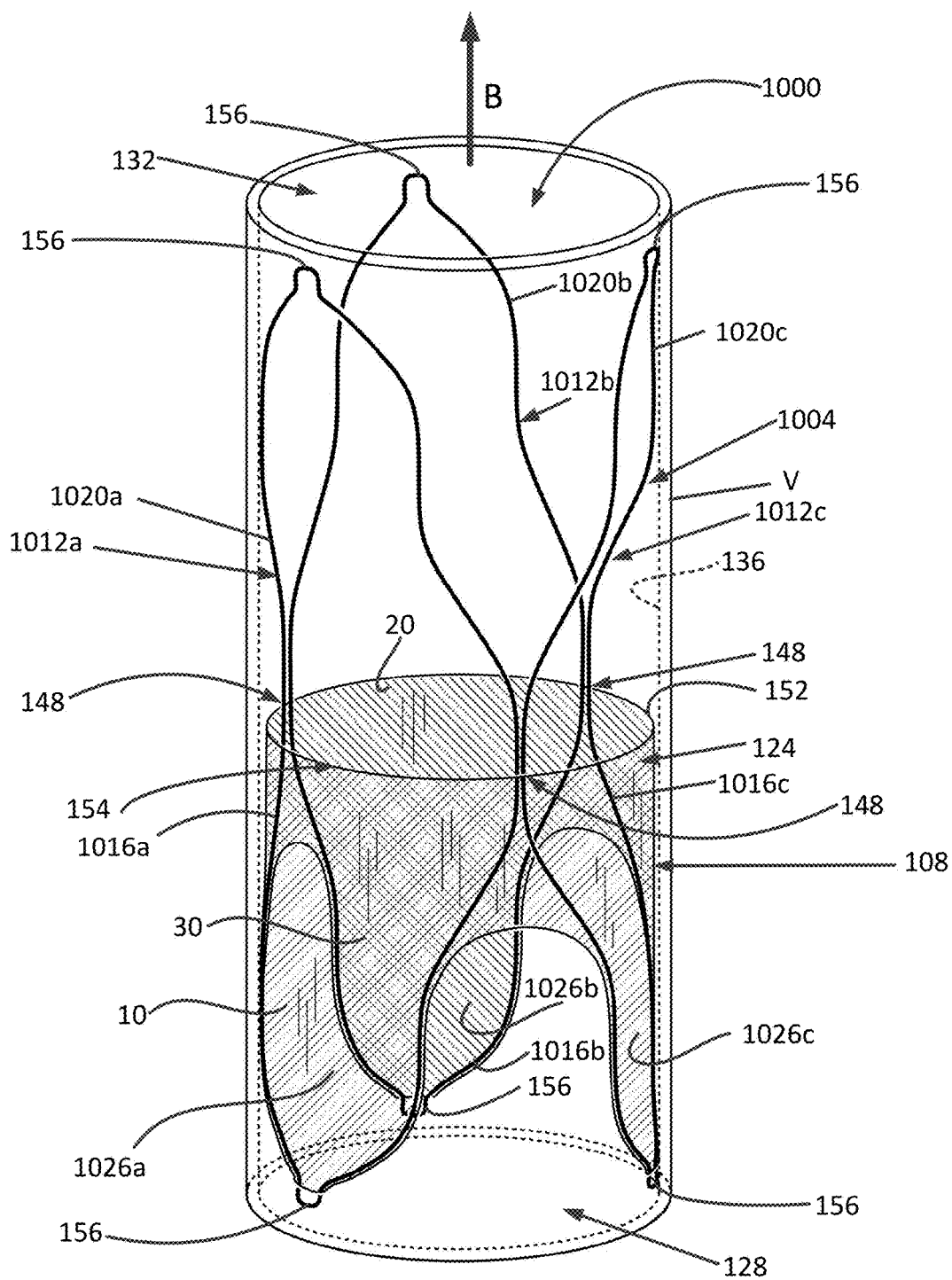
FIG. 10 is another embodiment of a prosthetic vascular valve, wherein the prosthetic vascular valve is shown situated within a section of a vein.
Figure 24A:
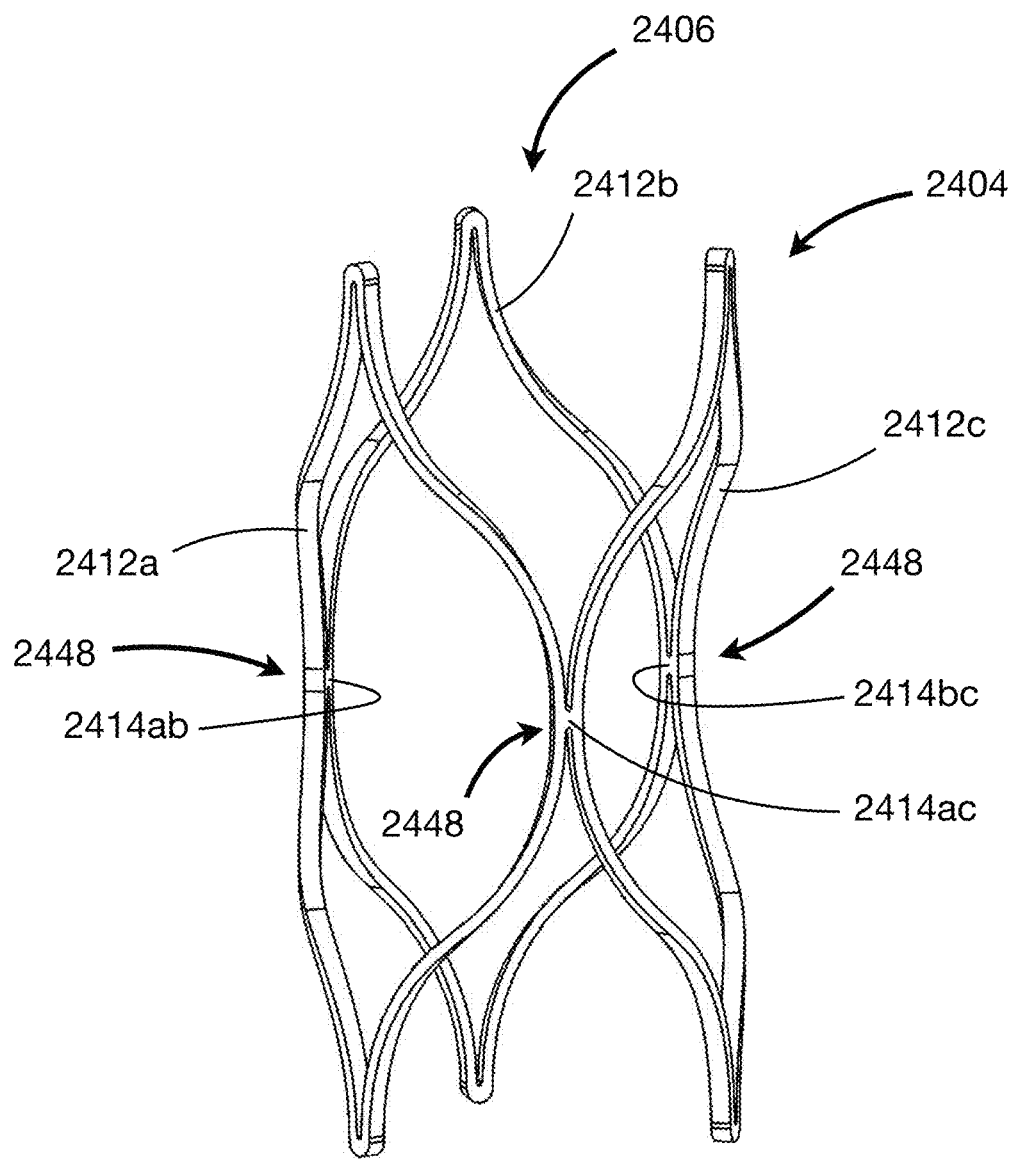
FIG. 24A is a side perspective view of an embodiment of a single-piece three-loop frame cut from a tube of material, the single-piece frame generally substitutable for the frame shown in FIG. 10.

Referring now to FIG. 24A, another embodiment of a frame 2404 is shown that has been cut from a cylindrical alloy tube, thus providing a shape with an outer surface to reside against a cylindrical-shaped vessel. More particularly, the frame 2404 includes a three-loop structure 2406 including a first loop 2412a, a second loop 2412b, and a third loop 2412c. It should be appreciated that the shape of the loops 2412a, 2412b and 2412c are designed as a curvilinear course along a cylinder such that by virtue of geometry, the frame 2404 maintains wall contact within a generally cylindrical vessel, such as a vein, along the full length of the prosthetic vascular valve. In at least one embodiment, the entire frame 2404 is a single piece of material. Accordingly, in at least one embodiment, the first loop 2412a is interconnected to the second loop 2412b by a first loop joining area 2414ab, the second loop 2412b is interconnected to the third loop 2412c by a second loop joining area 2414bc, and the third loop 2412c is interconnected to the first loop 2412a by a third loop joining area 2414ac. Therefore, the embodiment of the frame 2404 shown in FIG. 24 includes three loop joining areas 2414ab, 2414bc and 2414ac, wherein the three loop joining areas 2414ab, 2414bc and 2414ac are located approximately 120 degrees circumferentially from one another. As with frame 2204, the loop joining areas 2414ab, 2414bc and 2414ac of frame 2404 may comprise a section of the frame 2404 where the first loop 2412a merges with the second loop 2412b, where the first loop 2412a merges with the third loop 2412c, and where the second loop 2412b merges with the third loop 2412c. Alternatively, one to three of the loop joining areas 2414ab, 2414bc and 2414ac may comprise a bridging strut, wherein at least some material spans between two of the loops, such as between the first loop 2412a and the second loop 2412b, between the second loop 2412a and the third loop 2412c, and between the first loop 2412a and the third loop 2412c. To form a prosthetic vascular valve, a membrane 124 can be attached to the frame 2404 (as shown in FIGS. 10, 12 and 13), such as by suturing the membrane 124 to the frame, wherein the free edges 152 of the membrane (shown in FIG. 10) are generally aligned with portions of the longitudinally oriented strand convergence areas 2448 and the loop joining areas 2414ab, 2414bc and 2414ac as depicted in FIG. 24A. Accordingly, a frame with three longitudinally oriented loops may possess a membrane with three leaflets.

Figure 24B:
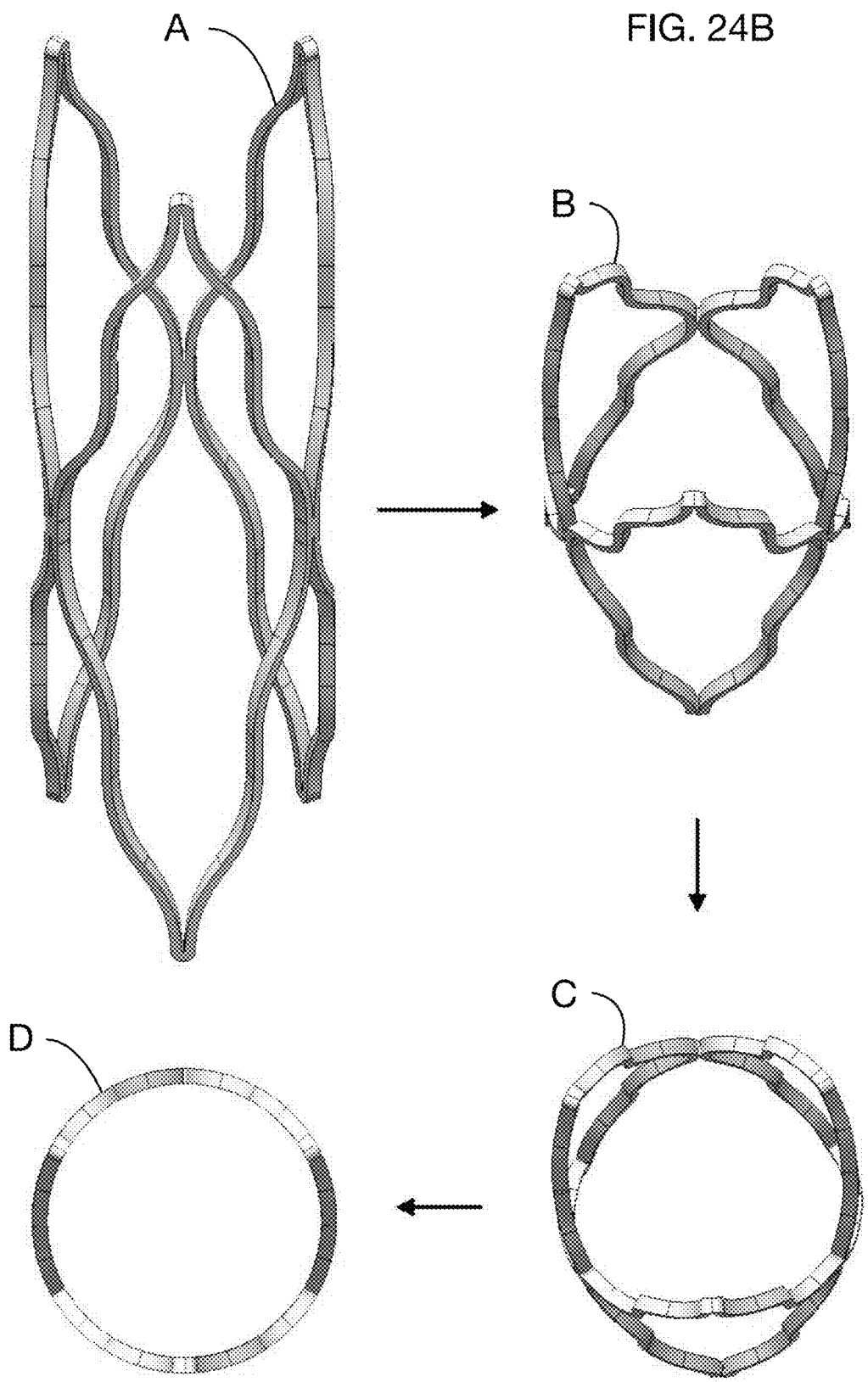
FIG. 24B is a series of four rotating views (that is, from a perspective view to an end view) of the frame shown in FIG. 24A.

Referring now to FIG. 24B, four different views of the loops of the frame of FIG. 24A are shown with the angle of view shifting between the views "A" to "D". More particularly, view "A" in the upper left is a perspective view. View "B" in the upper right illustrates the appearance of the loops with some rotation of the loops toward an end view relative to view "A". Moving further clockwise, view "C" in the lower right is further rotated toward and end view, and view "D" in the lower left of FIG. 24B is an end view of the loops. As can be seen in the progression of views "A" to "D", the portions of the loops, curved or otherwise, provide that the radially outer surfaces of the loops are configured to lie on a common cylinder so as to advantageously contact the inner surface of a blood vessel when the valve device is deployed therein.

Figure 25:
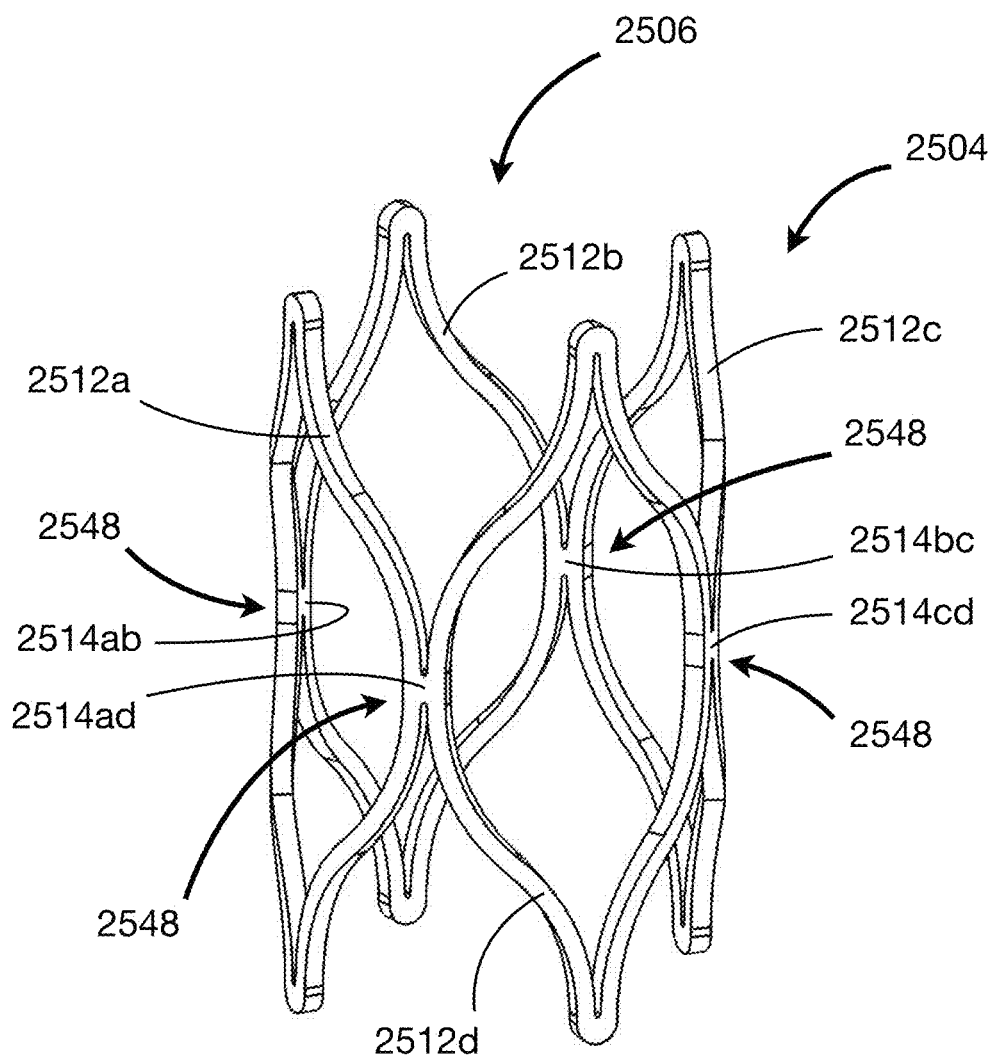
FIG. 25 is a side perspective view of an embodiment of a single-piece four-loop frame cut from a tube of material.

Referring now to FIG. 25, another embodiment of a frame 2504 is shown that has been cut from a cylindrical alloy tube, thus providing a shape with an outer surface to reside against a cylindrical-shaped vessel. More particularly, the frame 2504 includes a four-loop structure 2506 including a first loop 2512a, a second loop 2512b, a third loop 2512c, and a fourth loop 2512d. It should be appreciated that the shape of the loops 2512a, 2512b, 2512c and 2512d are designed as a curvilinear course along a cylinder such that by virtue of geometry, the frame 2504 maintains wall contact within a generally cylindrical vessel, such as a vein, along the full length of the prosthetic vascular valve. In at least one embodiment, the entire frame 2504 is a single piece of material. Accordingly, in at least one embodiment, the first loop 2512a is interconnected to the second loop 2512b by a first loop joining area 2514ab, the second loop 2512b is interconnected to the third loop 2512c by a second loop joining area 2514bc, the third loop 2512c is interconnected to a fourth loop 2512d by a third loop joining area 2514cd, and the fourth loop is connected to the first loop 2512a by a fourth loop joining area 2514ad. Therefore, the embodiment of the frame 2504 shown in FIG. 25 includes four loop joining areas 2514ab, 2514bc, 2514cd, and 2514ad, wherein the four loop joining areas 2514ab, 2514bc, 2514cd, and 2514ad are located approximately 90 degrees circumferentially from one another. As with frames 2204 and 2404, the loop joining areas 2514ab, 2514bc, 2513cd and 2514ad of frame 2504 may comprise a section of the frame 2504 where the first loop 2512a merges with the second loop 2512b, where the first loop 2512a merges with the fourth loop 2512d, where the second loop 2512b merges with the third loop 2512c, and where the third loop 2512c merges with the fourth loop 2512d. Alternatively, one to four of the loop joining areas 2514ab, 2514bc, 2514cd and 2514ad may comprise a bridging strut, wherein at least some material spans between two of the loops, such as between the first loop 2512a and the second loop 2512b, between the second loop 2512a and the third loop 2512c, between the third loop 2512c and the fourth loop 2512d, and between the first loop 2512a and the fourth loop 2512d. To form a prosthetic vascular valve, a membrane 124 can be attached to the frame 2504, such as by suturing the membrane 124 to the frame, wherein the free edges 152 of the membrane is generally aligned with portions of the longitudinally oriented strand convergence areas 2548 and the loop joining areas 2514ab, 2514bc, 2514cd and 2514adC as depicted in FIG. 25. Accordingly, a frame with four longitudinally oriented loops would possess a membrane with four leaflets. More generally, a frame with multiple loops may also possess a membrane with an independent or lesser number of leaflets when the membrane is attached to the inner surface of the frame.

As those skilled in the art will appreciate, prosthetic vascular valves with five or six loops are also possible. More particularly, a tube of alloy material may be cut to form a single piece of material that has five loops or six loops. Such five or six loops frames would be similar to the constructs depicted in FIGS. 24 and 25, but with additional loops. Accordingly, a frame with five or six longitudinally oriented loops would possess membranes with five or six leaflets, respectively. However, a frame may be configured for radial strength with multiple loops, but may also possess a membrane attached to the inner surface of the frame that may have an independent or lesser number of leaflets. The prosthetic vascular valves with a greater number of loops and corresponding number of leaflets may have particular application to treatment of deep central veins.

Figure 26:
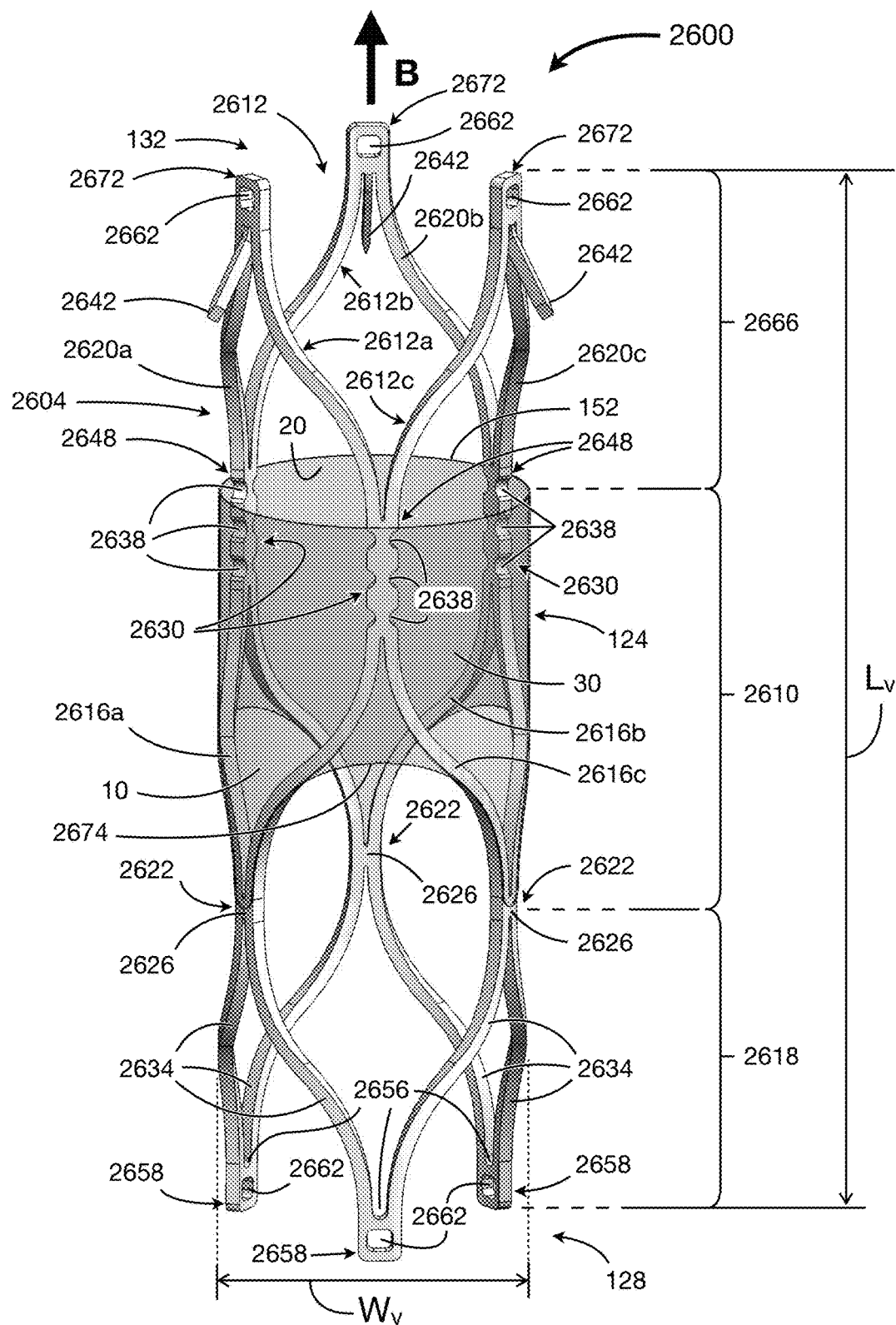
FIG. 26 is a side perspective view of another embodiment of a prosthetic vascular valve, the prosthetic vascular valve including a single-piece three-loop frame and a membrane attached to a longitudinally intermediate portion of frame.
Figure 27:
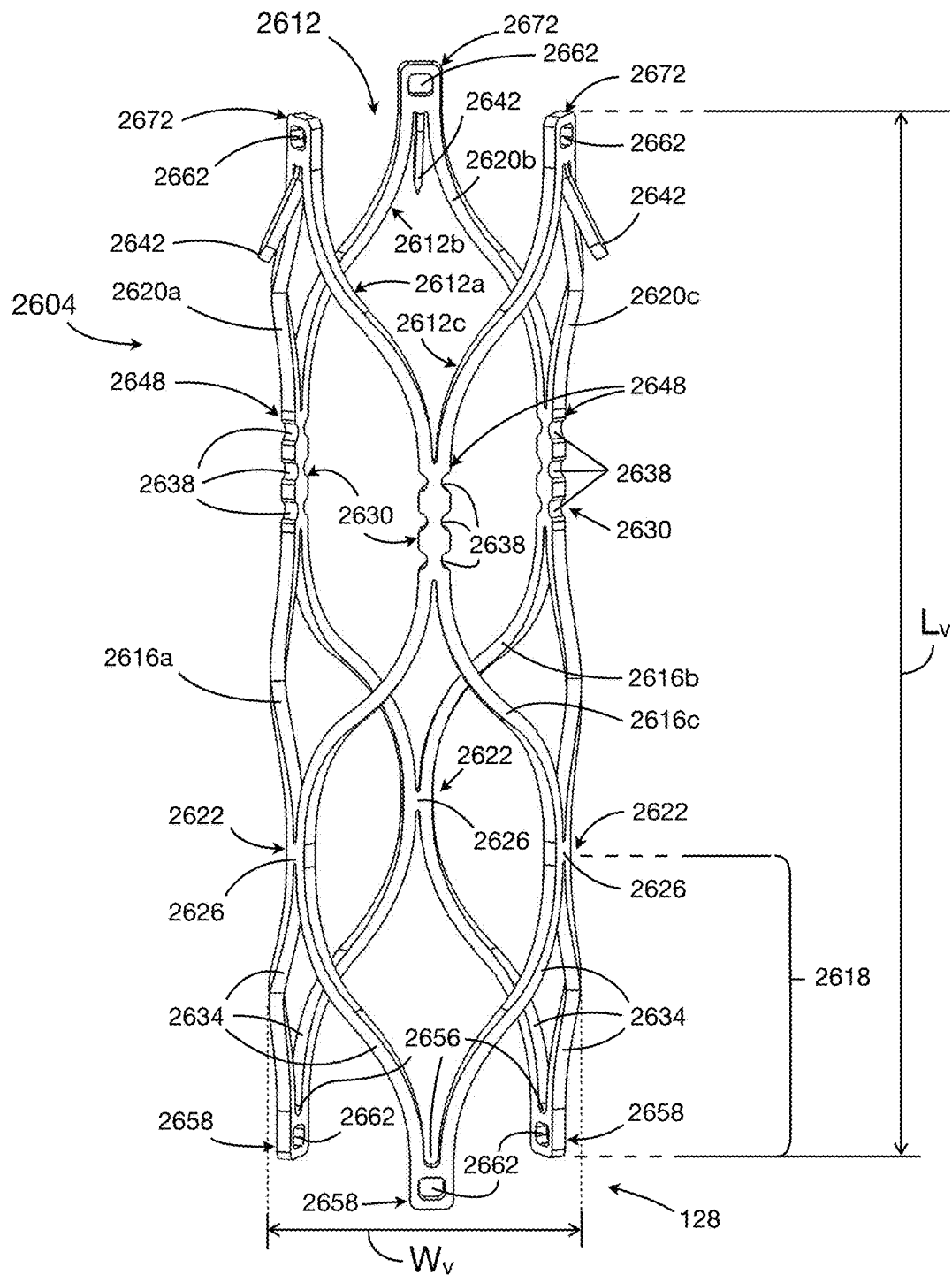
FIG. 27 is a side perspective view of the frame shown in FIG. 26.

Referring now to FIGS. 26 and 27, yet another embodiment of a prosthetic vascular valve 2600 is shown, wherein FIG. 26 depicts valve 2600 that includes frame 2604 and membrane 124, and FIG. 27 depicts the frame 2604 without membrane 124. In at least one embodiment, the entire frame 2604 is a single piece of material. Throughout all the portions of the loops, curved or otherwise, and with the exception of the barbs 2642 that are heat set to project outward after the frame is cut from a cylindrical-shaped alloy tube, the radially outer surfaces of the loops of the frame 2604 are configured to lie on a common cylinder so as to advantageously contact the inner surface of the vessel at all surface points of the loops when the valve device is deployed in a blood vessel.

For FIG. 26, the direction of blood flow B is shown at the top of the page. Prosthetic vascular valve 2600 includes a membrane 124 that is positioned within a longitudinally intermediate portion 2610 of the length Lv of the frame 2604, the frame 2604 having a plurality of loops 2612. In the example embodiment shown in FIGS. 26 and 27, the frame 2604 includes a first loop 2612a, a second loop 2612b, and a third loop 2612c; however, it is to be understood that a prosthetic vascular valve may include a different number of loops other than three, such as two loops, four loops, five loops or six loops, wherein, as noted above, the greater number of loops may have particular application to treatment of deep central veins, such as a popliteal vein. Similar to the three-loop configuration shown in FIGS. 10 and 12, the first loop 2612a includes a first longitudinal portion 2616a and a second longitudinal portion 2620a. The second loop 2612b includes a first longitudinal portion 2616b and a second longitudinal portion 2620b. The third loop 2612c includes a first longitudinal portion 2616c and a second longitudinal portion 2620c. Per the example embodiment shown in FIG. 26, the membrane 124 is attached to the first longitudinal portions 2616a, 2616b and 2616c, wherein the first longitudinal portions are generally situated within a longitudinally intermediate portion 2610 of the frame 2604.

For the example three-loop configuration illustrated in FIGS. 26 and 27, the frame 2604 further includes a frame extension 2618 located proximally of the proximal ends 2622 of the first loop 2612a, second loop 2612b and third loop 2612c. In at least one embodiment, joints 2626 are located proximal to the first loop 2612a, second loop 2612b and third loop 2612c, and advantageously, the joints 2626 structurally interconnect extension struts 2634 distally. In addition, extension struts 2634 are interconnected proximally at eyelets 2656. It at least one embodiment, the eyelets 2656 are positioned adjacent and distal to closed proximal apertures 2658, which are optional, wherein the closed proximal apertures 2658 include a framed aperture 2662 that may be used to receive a line for applying tension to the frame 2604, such as when loading the prosthetic vascular valve 2600 into a delivery device. Alternatively or in addition thereto, a radio opaque material may be permanently installed to fill all or a portion of the framed aperture 2662, thus providing a way to facilitate viewing during deployment procedures. In addition to the foregoing, the eyelets 2656 may also be used to receive a line for applying tension to the frame 2604, such as when loading the prosthetic vascular valve 2600 into a delivery device.

The joints 2626 are circumferentially offset from the commissure posts 2630, wherein the commissure posts 2630 are positioned near the distal extent of the membrane 124. For the prosthetic vascular valve 2600, the membrane 124 includes a free edge 152 that allows the membrane to open and close. More particularly, as illustrated in FIG. 26, a membrane 124 is shown in its attachment location to the frame 2604 (wherein sutures and/or other membrane securing fasteners are omitted for clarity). As shown in FIGS. 26 and 27, the commissure posts 2630 may include one or more suture notches 2638 for receiving sutures (not shown) to secure the membrane 124 to the frame 2604. For commissure posts 2630 illustrated in the embodiment shown in FIGS. 26 and 27, three longitudinally spaced-apart suture notches 2638 are located at each commissure post 2630. However, it is to be understood that the commissure posts 2630 may utilize more or less suture notches than are shown in FIGS. 26 and 27, to include one, two, four, five or six suture notches along the longitudinal length of the commissure posts 2630. The commissure posts 2630 correspond to the strand convergence areas 2648 and loop joining areas. For the example embodiment illustrated in FIGS. 26 and 27, the adjacent members of the first loop 2612a, second loop 2612b and third loop 2612c are merged at the convergence areas 2648, such that the commissure posts 2630 provide a shared structural element between the adjacent loops. That is, between the first loop 2612a and the second loop 2612b, between the second loop 2612b and the third loop 2612c, and between first loop 2612a and the third loop 2612c.

For the embodiment shown in FIGS. 26 and 27, the distal end 132 of the frame 2604 may optionally include one or more barbs 2642 that extend radially beyond the valve width Wv and provide a structure for anchoring the prosthetic vascular valve 2600 within the vein or other vasculature within which the prosthetic vascular valve 2600 is implanted. However, it should be appreciated that the shape of the loops 2612 and the frame extension 2618 are designed as a curvilinear course along a cylinder such that by virtue of geometry, the frame 2604 maintains wall contact within a generally cylindrical vessel, such as a vein, along the full length or substantially the full length of the prosthetic vascular valve 2600.

The distal end 132 of the plurality of loops 2612 may include eyelets or may include closed distal apertures 2672 as shown in FIGS. 26 and 27. The closed distal apertures 2672 include a framed aperture 2662 that may be used to receive a line for applying tension to the frame 2604, such as when loading the prosthetic vascular valve 2600. Alternatively or in addition thereto, a radio opaque material may be permanently installed to fill all or a portion of the framed aperture 2662, thus providing a way to facilitate viewing during deployment procedure.

In at least one embodiment, the membrane 124 includes an arcuate-shaped proximal edge 2674 located proximal to each commissure post 2630. More particularly, in order to prevent or limit retrograde flow back through a prosthetic vascular valve, the membrane material preferably extends along some longitudinal length of the prosthetic vascular valve. Thus, while the membrane material could be terminated just proximally to the commissure post 2630, it is preferable to extend the membrane at least some distance proximally relative to the commissure post 2630. However, if the membrane material is extended to the proximal end 128 of the frame 2604, then free edges will extend between the proximal ends of the frame, such as between the closed proximal apertures 2858 that are approximately 120 degrees apart for the example three-loop prosthetic vascular valve 2600 shown in FIG. 26. Accordingly, use of an arcuate-shaped proximal edge 2674 located proximal to the commissure post 2630 and distal to the proximal ends 2622 of the first loop 2612a, second loop 2612b and third loop 2612c, limits the amount of proximal free edge of the membrane that is exposed to prevent normal blood flow, while also providing a reasonable amount of membrane material to prevent or limit leakage in a retrograde direction.

For the example prosthetic vascular valve 2600 shown in FIGS. 26 and 27, distal longitudinal portion 2666 does not include any membrane; however, membrane material could be attached that is not part of the membrane 124 at the longitudinally intermediate portion 2610 that forms leaflets for opening and closing, such as the closed leaflet configuration shown in FIG. 12.

Figure 28:
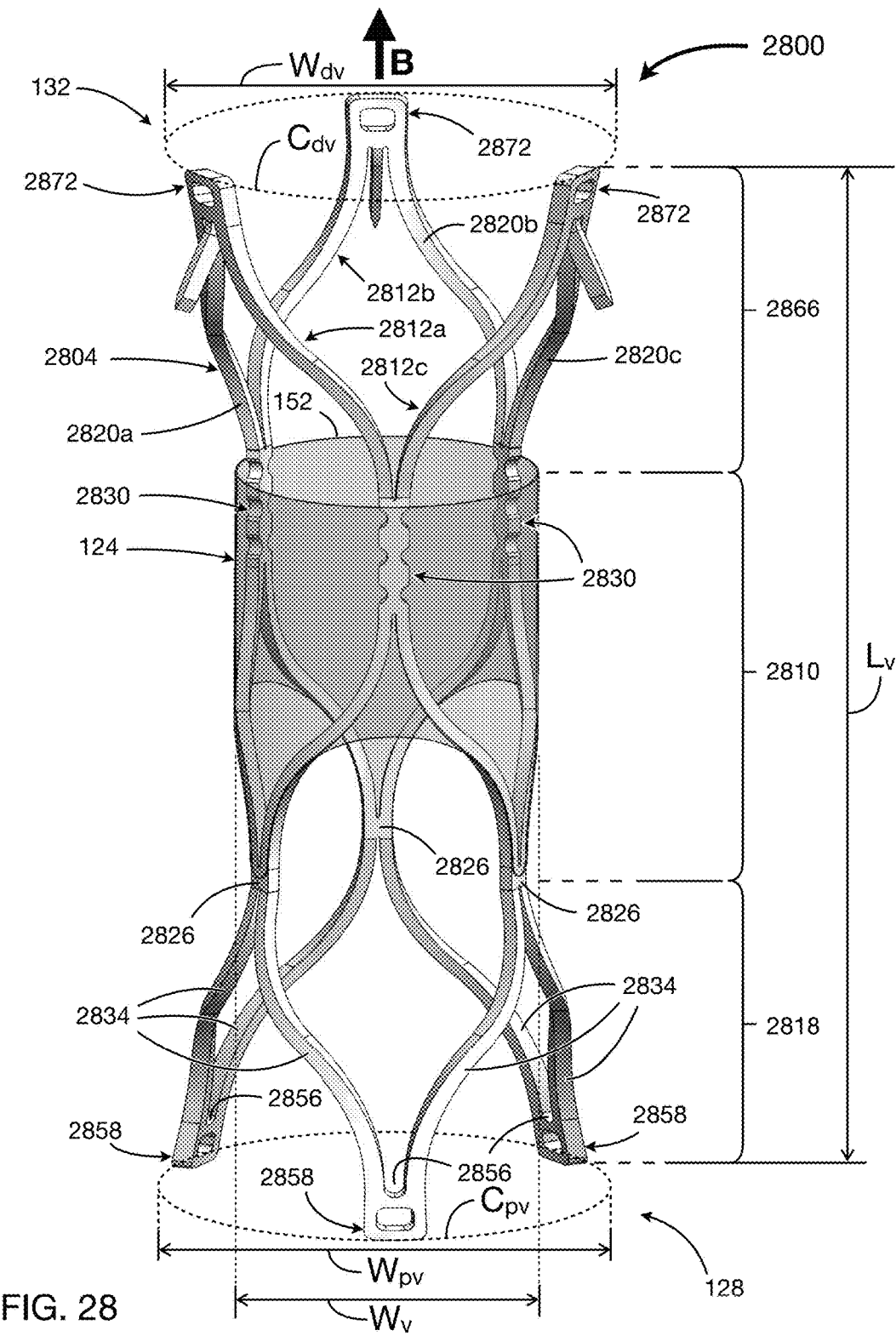
FIG. 28 is a side perspective view of yet another embodiment of a prosthetic vascular valve, the prosthetic vascular valve including a single-piece three-loop frame with flared frame portions on the proximal and distal sides of the membrane.
Figure 29:
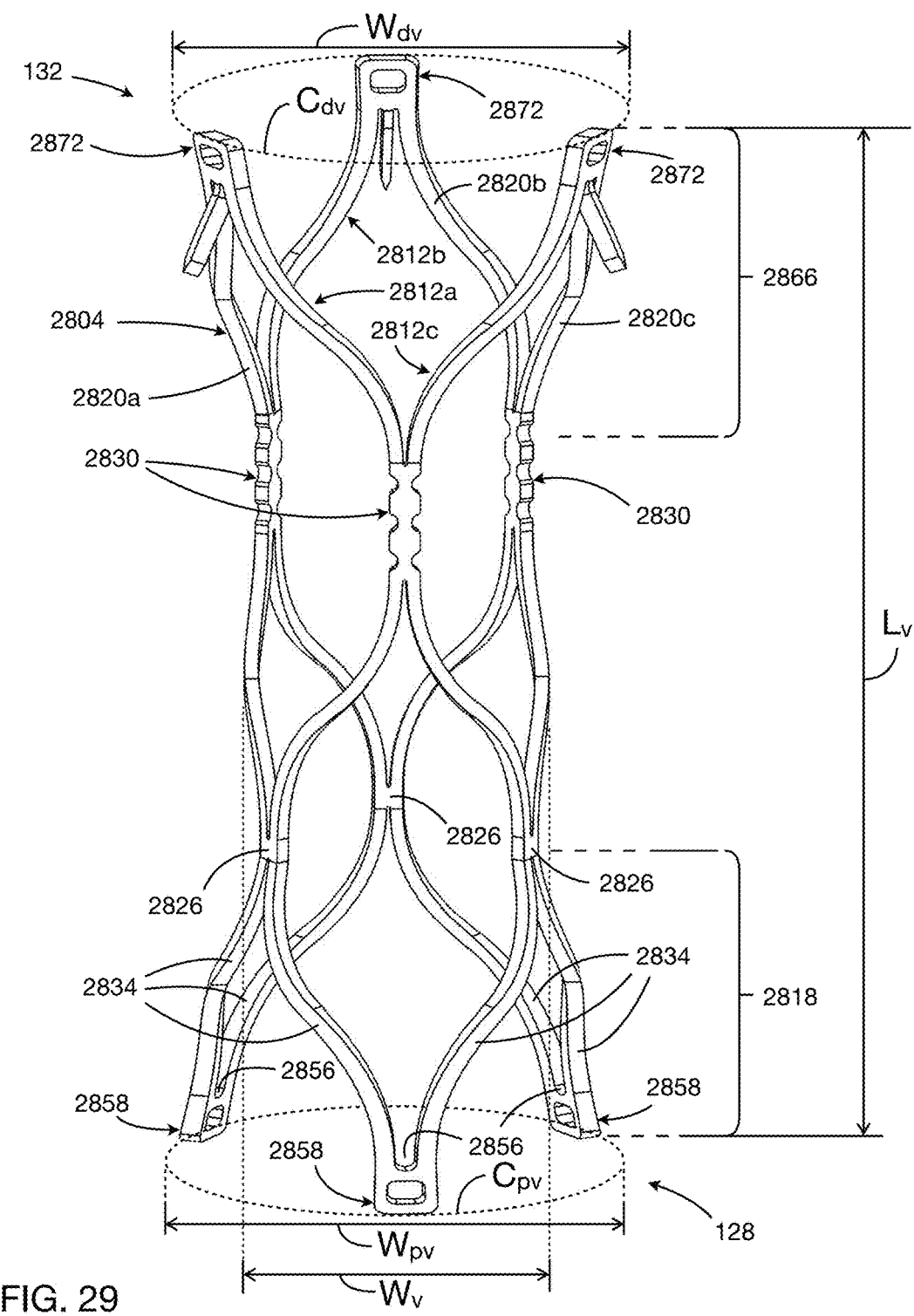
FIG. 29 is a side perspective view of the frame shown in FIG. 28.

Referring now to FIGS. 28 and 29, yet another embodiment of a prosthetic vascular valve 2800 is shown, wherein FIG. 28 depicts valve 2800 that includes frame 2804 and membrane 124, and FIG. 29 depicts the frame 2804 without membrane 124. In at least one embodiment, the entire frame 2804 is a single piece of material. For FIG. 28, the direction of blood flow B is shown at the top of the page. The prosthetic vascular valve 2800 possesses a number of similarities to the prosthetic vascular valve 2600 shown in FIG. 26, and therefore, most of the similar structure is not repeated here. However, the frame 2804 of prosthetic vascular valve 2800 includes flared portions both proximally and distally of the longitudinally intermediate portion 2810 that includes the membrane 124. That is, the longitudinally intermediate portion 2810 is the loop section of the frame that contains a plurality of loops, and wherein a loop section length of the loop section of the frame is about two to eight times greater than a width of the loop section when no incident radially directed force is acting on the frame. The frame extension 2818 proximal to the membrane 124 includes flared extension struts 2834, wherein the flared extension struts 2834 are tapered and flare outward. In one embodiment, the flared extension struts 2834 flare radially outward in a proximal direction. In one embodiment, the flared extension struts 2834 flare increasingly radially outward in a proximal direction from the joints 2826 to eyelets 2856, and may continue to flare to the proximal end of the closed proximal apertures 2858, which are optional. At the proximal end 128 of the prosthetic vascular valve 2800, a proximal valve width Wpv is greater than a diameter or valve width at the longitudinally intermediate portion 2810, which matches the valve width Wv shown in FIGS. 26 and 27, and which is included at the bottom of FIG. 29. To assist with understanding the difference between the valve width Wv and the proximal valve width Wpv, a dashed line for the proximal valve circumference Cpv is provided. The proximal valve width Wpv is then tied to the diameter of the proximal valve circumference Cpv.

Referring still to FIGS. 28 and 29, the prosthetic vascular valve 2800 further includes a distal flared portion 2866. In one embodiment, the distal flared portion 2866 corresponds to the second longitudinal portions 2820a, 2820b and 2820c of loops 2812a, 2812b and 2812c, respectively, wherein the second longitudinal portions 2820a, 2820b and 2820c are located distally of the free edge 152 of membrane 124. It is to be understood that a prosthetic vascular valve may include a different number of loops other than three, such as two loops, four loops, five loops or six loops. In one embodiment, the second longitudinal portions 2820a, 2820b and 2820c flare radially outward in a distal direction. In one embodiment, second longitudinal portions 2820a, 2820b and 2820c flare radially outward in a distal direction from the top of the commissure posts 2830 to the distal end 132 of the prosthetic vascular valve 2800, such as to the closed distal apertures 2872. At the distal end 132 of the prosthetic vascular valve 2800, a distal valve width Wdv is greater than a diameter or valve width at the longitudinally intermediate portion 2810, which matches the valve width Wv shown in FIGS. 26 and 27, and which is shown at the bottom of FIG. 29. To assist with understanding the difference between the valve width Wv and the distal valve width Wdv, a dashed line for the distal valve circumference Cdv is provided. The distal valve width Wdv is then tied to the diameter of the distal valve circumference Cdv.

The flared portions of the frame 2804 may be formed by heat setting the desired flare shape to a shape memory material, such as nitinol. In addition, the barbs depicted on the distal end of the frame 2804 may also be formed by heat setting the desired barb angles.

For the longitudinally intermediate portion 2810, the radially outer surfaces of the loops within this portion of the frame are configured to lie on a common cylinder so as to advantageously contact the inner surface of the vessel at all surface points of the loops along the longitudinally intermediate portion 2810 when the valve device is deployed in a blood vessel.

It at least one embodiment, the proximal valve width Wpv is equal or substantially equal to the distal valve width Wdv, and both the proximal valve width Wpv and the distal valve width Wdv are greater than a diameter or valve width Wv at the longitudinally intermediate portion 2810. In at least one embodiment, the proximal valve width Wpv is not equal to the distal valve width Wdv, and both the proximal valve width Wpv and the distal valve width Wdv are greater than a diameter or valve width Wv at the longitudinally intermediate portion 2810. In at least one embodiment, the proximal valve width Wpv is greater than the distal valve width Wdv, and both the proximal valve width Wpv and the distal valve width Wdv are greater than a diameter or valve width Wv at the longitudinally intermediate portion 2810. In at least one embodiment, the proximal valve width Wpv is less than the distal valve width Wdv, and both the proximal valve width Wpv and the distal valve width Wdv are greater than a diameter or valve width Wv at the longitudinally intermediate portion 2810.

Prosthetic vascular valves with flared portions are anticipated to be preferred for larger veins. More particularly, adding one or more flared portions to the frames of a prosthetic vascular valve is anticipated to allow the prosthetic vascular valve to accommodate larger distending displacements associated with the target vein within which the prosthetic vascular valve with flared portions is implanted.

Multiple frame segments for a multiple prosthetic vascular valve construct may be formed by cutting tubing to generate the frames for such multiple frame segments, wherein the framing is a material such as nitinol tubing. For example, tubing can be cut to include two or more end-to-end prosthetic vascular valves, such as prosthetic vascular valves 2600 and/or 2800. Such multiple segments of prosthetic vascular valves may be formed by cutting end-to-end connected frames in a single piece, for example any of the frames described herein, including frames 2204, 2404, 2504, 2604 and/or 2804 Alternatively or additionally, multiple frames, such as two or more of any of the frames shown or described herein, including frames 2204, 2404, 2504, 2604 and/or 2804, can be joined, such as by joining the distal end of a first frame to a proximal end of a second frame, wherein such joining is done by linking the frames, such as by suturing, using a ring of material, using a portion of frame material, or welding the frames together. In at least one embodiment, linking members may be sized to accommodate forces associated with pushing the linked multiple prosthetic vascular valves during deployment.

As described herein, a tube of alloy material may be cut to form a frame for a prosthetic vascular valve, wherein the frame includes between two to six loops, and wherein the frame is a single piece of material. However, individual loops may also be cut from tube material and then interconnected, such as by utilizing a ring or a suture at the longitudinally oriented strand convergence areas. Moreover, one or more loops cut from a tube of alloy material could also include an opening, such that the one or more of the loops are not continuous. Such loops that are not continuous may be used with a membrane material that is woven over the loops in a manner similar to that described above and illustrated in FIG. 9.

For a prosthetic vascular valve with two loops, the commissures of the membrane material are preferably located approximately 180 degrees apart around the circumference of the frame. For a prosthetic vascular valve with three loops, the commissures of the membrane material are preferably located approximately 120 degrees apart around the circumference of the frame. For a prosthetic vascular valve with four loops, the commissures of the membrane material are preferably located approximately 90 degrees apart around the circumference of the frame. For a prosthetic vascular valve with five loops, the commissures of the membrane material are preferably located approximately 72 degrees apart around the circumference of the frame. For a prosthetic vascular valve with six loops, the commissures of the membrane material are preferably located approximately 60 degrees apart around the circumference of the frame.

Figure 30:
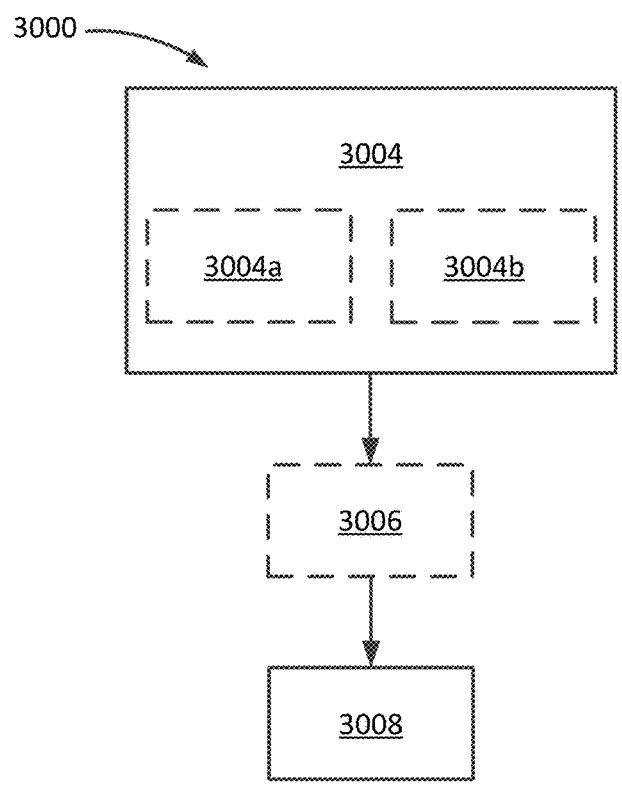
FIG. 30 is a flow diagram of a method of making a prosthetic vascular valve.
Figure 31:
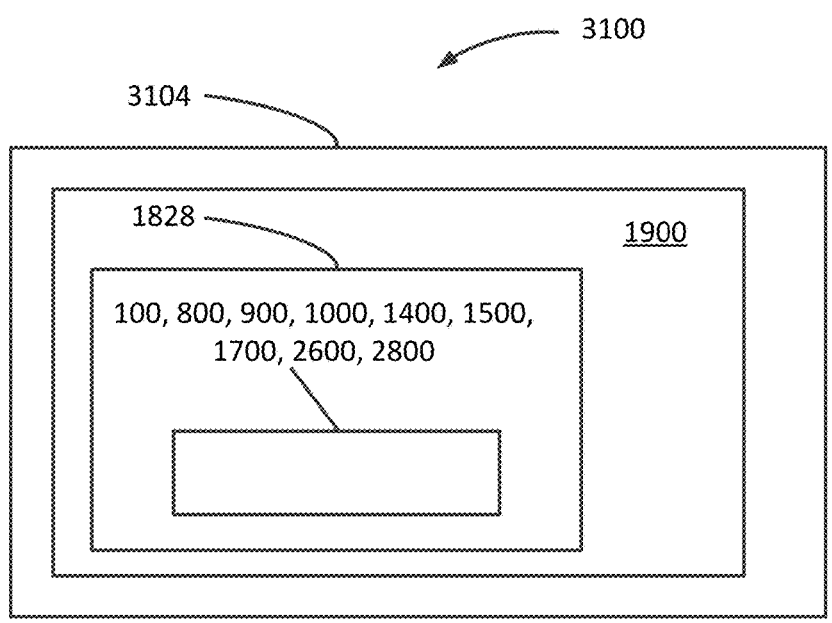
FIG. 31 is a schematic of an assembly, including a sterile package with a delivery system and a prosthetic vascular valve loaded in a delivery device forming part of the delivery system.

Methods of making a prosthetic vascular valve are also contemplated. More particularly, FIG. 30 shows a flow diagram of an exemplary method of making 3000 a prosthetic vascular valve. The method 3000 includes manufacturing 3004 a frame. In accordance with the method 3000, the frame is collapsible and expandable. The frame has a length that is about two to eight times greater than a width of the frame when no incident radially directed force is acting on the frame. The method 3000 of making a prosthetic vascular valve further includes attaching 3008 a membrane (such as membrane 124) to the frame. Upon attaching the membrane to the frame, the membrane includes a free edge that is configured to be moveable from an open position to a closed position.

The step of manufacturing 3004 may include the step of cutting 3004*a* the frame (such as frames 2204, 2404, 2504, 2604 and 2804 as described herein) from a tube of material. Alternatively, the step of manufacturing 3004 may include the step of forming 3004*b* the frame (such as frames 104, 804, 904, 1004, 1404 and 1504 as described herein) from one or more pieces of wire. For the case of using nitinol or another shape memory alloy material to manufacture the frame by cutting or forming the frame, the method may further include the additional step of heat setting 3006 the frame in between the steps of manufacturing 3004 the frame and attaching 3008 the membrane to the frame. For the method of making 3000 a prosthetic vascular valve, the frame includes two loops, wherein each of the two loops includes a first longitudinal portion and a second longitudinal portion, and wherein the attaching 3008 step of the method 3000 further includes the step of attaching the membrane to the first longitudinal portions for the two loops.

In one or more embodiments, a method of making a frame for use in manufacturing a prosthetic vascular valve is provided, the method including:
preparing a frame by one of:
(a) cutting the frame from a tube of material; or
(b) forming the frame from one or more pieces of wire;
wherein the frame has a length that is about two to eight times greater than a width of the frame, and wherein the frame includes two to six loops, each loop including a first longitudinal portion and a second longitudinal portion, wherein the frame is configured to receive a membrane that includes leaflets radially moveable from an open position to a closed position. Here, the method of making the frame does not include attachment of the membrane to the frame.

A method of making a prosthetic vascular valve includes: (a) obtaining a frame, wherein the frame includes a plurality of loops that extend in an axial direction of the frame, and wherein an outer surface of the plurality of loops is configured to lie on a common cylinder; and (b) attaching a membrane to the frame to form a valve.

For the prosthetic vascular valves described herein, one or more valves can be packaged in a suitable container for shipping to a hospital or other facility for implantation in a patient. More preferably, the prosthetic vascular valves can be crimped and back-loaded into a sheath, such as shaft of a needle or a delivery catheter, and thereafter packaged for delivery. By way of example, the package may contain one or more prosthetic vascular valves, one or more preloaded needles or delivery catheters, as well as any associated tools and instructions. After the package is loaded and sealed, the package may thereafter be sterilized, such as by exposure of the interior of the package to a sterilant, for example, by the addition of ethylene oxide gas into the interior of the package. For the embodiments described herein that include tissue, the membrane may be treated pericardial tissue or vascular tissue that is dried sufficiently to facilitate handling and is then sutured or otherwise attached to the frame, such as by stapling, bonding and/or weaving the tissue onto the frame (as described herein), and thereafter crimped and packaged in a dried state, without necessarily hydrating the tissue during the crimping process, although hydrating during the crimping processes is optional.

Accordingly, in at least one embodiment, a kit or an assembly 3100 is provided that includes a sterile package 3104 with one or more prosthetic vascular valves 100, 800, 900, 1000, 1400, 1500, 1700, 2600, and/or 2800, contained in the package 3104. More particularly, a prosthetic vascular valve including a frame and a membrane attached to the frame is provided within the sterile package 3104, wherein the contents within the sterile package 3104 are sterile and are ready for use at a medical facility. As described herein, the membrane includes a free edge that is configured to be moveable from an open position to a closed position. The frame includes a loop section with a plurality of loops, wherein the membrane is attached to the loop section. The plurality of loops extend in an axial direction of the frame, and an outer surface of the plurality of loops is configured to lie on a common cylinder. The sterile package 3104 includes a delivery system 1900, such as a delivery device 1828 with a plunger and may further include other items, such as any associated tools and instructions. The delivery device is sized to hold the prosthetic vascular valve or valves. Indeed, multiple delivery devices with different types of prosthetic vascular valves may be provided as part of the delivery system. Per the various embodiments of the prosthetic vascular valves described in this disclosure, the frame may include between two to six loops of material, such as nitinol wire or nitinol material cut from a tube. As also described in this disclosure, at least two of the two to six loops of material may include continuous loops of material. Advantageously, the prosthetic vascular valve may be preloaded into the delivery device. In this configuration, the sterile package can opened at the medical facility, the delivery system removed from the sterile package and used without having to load the prosthetic vascular valve into the delivery device. Within the sterile package, the membrane of the prosthetic vascular valve may reside within a liquid, such as saline. For packaging with the prosthetic vascular valve preloaded into the delivery device, the portion of the delivery device holding the prosthetic vascular valve may reside within a liquid, such as saline. Alternatively, the prosthetic vascular valve may not reside within a liquid, and in such cases, the membrane does not exhibit any detectable glutaraldehyde or other fixative.

Those skilled in the art will appreciate that the prosthetic vascular valves discussed herein also have applicability to uses other than within the veins of a patient. More particularly, and without intending to be limited, the prosthetic vascular valves could be used as shunts within other fluid conveyance portions of the human anatomy. Moreover, the prosthetic vascular valves also have application to veterinary medicine.

The one or more present inventions may be embodied in other specific forms without departing from its spirit or essential characteristics. The described embodiments are to be considered in all respects only as illustrative and not restrictive. The scope of the one or more present inventions is, therefore, indicated by the appended claims rather than by the foregoing description. All changes which come within the meaning and range of equivalency of the claims are to be embraced within their scope.

Moreover, though the description of the one or more present inventions has included description of one or more embodiments and certain variations and modifications, other variations and modifications are within the scope of the one or more present inventions (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A prosthetic vascular valve for use in a blood vessel or vascular conduit, the prosthetic vascular valve comprising:
   a frame including a loop section having a first loop and a second loop, wherein the first loop is situated diametrically opposite the second loop, wherein a length of the loop section of the frame is about two to eight times greater than a width of the loop section; and
   a membrane attached to the first loop and the second loop, the membrane including mobile portions that are configured to move radially inward and radially outward corresponding to closed and open positions of a distal free edge of the membrane, respectively, wherein the mobile portions of the membrane reside between convergence areas of the first loop and the second loop, wherein the membrane includes a proximal edge that is spaced apart longitudinally from the convergence areas in a proximal direction.

2. The prosthetic vascular valve of claim 1, wherein an outer surface of the first loop and the second loop is configured to lie on a common cylinder.

3. The prosthetic vascular valve of claim 1, wherein the frame is made of a single piece of cut tubular material.

4. The prosthetic vascular valve of claim 1, wherein the frame is made of two wire pieces.

5. The prosthetic vascular valve of claim 1, wherein the membrane comprises a cross-linked mammalian tissue.

6. The prosthetic vascular valve of claim 1, wherein the membrane is a single piece of material that does not include any seams and is made from a cylindrical piece of donor tissue that has been treated, shaped and attached to the frame.

7. The prosthetic vascular valve of claim 1, wherein the proximal edge of the membrane includes an arcuate shape.

* * * * *